US012187744B2

(12) United States Patent
Leong et al.

(10) Patent No.: US 12,187,744 B2
(45) Date of Patent: Jan. 7, 2025

(54) IRAK4 DEGRADERS AND SYNTHESIS THEREOF

(71) Applicant: Kymera Therapeutics, Inc., Watertown, MA (US)

(72) Inventors: William Leong, Watertown, MA (US); Dharyl Charles Wilson, Heftfordshire (GB)

(73) Assignee: Kymera Therapeutics, Inc., Watertown, MA (US)

( * ) Notice: Subject to any disclaimer, the term of this patent is extended or adjusted under 35 U.S.C. 154(b) by 0 days.

(21) Appl. No.: 18/050,883

(22) Filed: Oct. 28, 2022

(65) Prior Publication Data

US 2023/0257399 A1 Aug. 17, 2023

Related U.S. Application Data

(60) Provisional application No. 63/263,274, filed on Oct. 29, 2021.

(51) Int. Cl.
*C07D 519/00* (2006.01)
*C07D 487/04* (2006.01)

(52) U.S. Cl.
CPC ......... *C07D 519/00* (2013.01); *C07D 487/04* (2013.01); *C07B 2200/07* (2013.01)

(58) Field of Classification Search
CPC ............................ C07D 487/04; C07D 519/00
See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,217,866 A | 6/1993 | Summerton et al. |
| 5,360,811 A | 11/1994 | Tegeler et al. |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 5,721,246 A | 2/1998 | Yoshino et al. |
| 6,306,663 B1 | 10/2001 | Kenten et al. |
| 6,552,065 B2 | 4/2003 | Remiszewski et al. |
| 6,559,280 B2 | 5/2003 | Kenten et al. |
| 6,627,754 B2 | 9/2003 | Blumenkopf et al. |
| 6,949,537 B2 | 9/2005 | Garlich et al. |
| 7,041,298 B2 | 5/2006 | Deshaies et al. |
| 7,071,189 B2 | 7/2006 | Kawashima et al. |
| 7,074,620 B2 | 7/2006 | Kenten et al. |
| 7,173,015 B2 | 2/2007 | Schreiber et al. |
| 7,208,157 B2 | 4/2007 | Dashaies et al. |
| 7,273,920 B2 | 9/2007 | Kenten et al. |
| 7,307,077 B2 | 12/2007 | Kawashima et al. |
| 7,390,799 B2 | 6/2008 | Bruncko et al. |
| 7,402,325 B2 | 7/2008 | Addington |
| 7,449,458 B2 | 11/2008 | Bhamidipati et al. |
| 7,501,496 B1 | 3/2009 | Endl et al. |
| 7,514,444 B2 | 4/2009 | Honigberg et al. |
| 7,528,143 B2 | 5/2009 | Noronha et al. |
| 7,557,210 B2 | 7/2009 | Singh et al. |
| 7,598,257 B2 | 10/2009 | Rodgers et al. |
| 7,622,496 B2 | 11/2009 | Larsen et al. |
| 7,667,039 B2 | 2/2010 | Garcia-Echeverria et al. |
| 7,713,943 B2 | 5/2010 | Klippel-Giese et al. |
| 7,781,433 B2 | 8/2010 | Chuckowree et al. |
| 7,932,260 B2 | 4/2011 | Fowler et al. |
| 7,989,622 B2 | 8/2011 | Bajjalieh et al. |
| 8,138,347 B2 | 3/2012 | Knight et al. |
| 8,185,616 B2 | 5/2012 | Nagata et al. |
| 8,217,035 B2 | 7/2012 | Burger et al. |
| 8,338,439 B2 | 12/2012 | Singh et al. |
| 8,486,941 B2 | 7/2013 | Burns et al. |
| 8,906,682 B2 | 12/2014 | June et al. |
| 9,334,320 B2 | 5/2016 | Okun et al. |
| 9,500,653 B2 | 11/2016 | Crews et al. |
| 9,632,089 B2 | 4/2017 | Crews et al. |
| 9,694,084 B2 | 7/2017 | Bradner et al. |
| 9,750,816 B2 | 9/2017 | Bradner et al. |
| 9,770,512 B2 | 9/2017 | Bradner et al. |
| 9,821,068 B2 | 11/2017 | Bradner et al. |
| 9,969,710 B2 | 5/2018 | Jorand-Lebrun et al. |
| 10,125,114 B2 | 11/2018 | Bradner et al. |
| 10,336,744 B2 | 7/2019 | Harling et al. |
| 10,874,743 B2 | 12/2020 | Mainolfi et al. |
| 11,065,231 B2 | 7/2021 | Crew et al. |
| 11,117,889 B1 | 9/2021 | Mainolfi et al. |
| 11,352,350 B2 | 6/2022 | Mainolfi et al. |
| 11,685,750 B2 | 6/2023 | Zheng et al. |
| 11,707,457 B2 | 7/2023 | Weiss |
| 11,773,103 B2 | 10/2023 | Rong et al. |
| 2001/0053782 A1 | 12/2001 | Blumenkopf et al. |
| 2002/0042427 A1 | 4/2002 | Tang et al. |
| 2002/0068063 A1 | 6/2002 | Deshaies et al. |
| 2002/0183360 A1 | 12/2002 | Muller et al. |
| 2004/0029902 A1 | 2/2004 | Singh et al. |
| 2004/0048859 A1 | 3/2004 | Germann et al. |
| 2004/0106569 A1 | 6/2004 | Klippel-Giese et al. |
| 2004/0116421 A1 | 6/2004 | Kawashima et al. |
| 2004/0242631 A1 | 12/2004 | Garlich et al. |
| 2005/0014802 A1 | 1/2005 | Attardo et al. |

(Continued)

FOREIGN PATENT DOCUMENTS

| | | |
|---|---|---|
| CN | 105085620 B | 5/2018 |
| WO | WO-1996007655 A1 | 3/1996 |

(Continued)

OTHER PUBLICATIONS

Blake et al., "Studies with deuterated drugs," J Pharm Sci. 1975;64(3):367-391.

(Continued)

*Primary Examiner* — Laura L Stockton

(74) *Attorney, Agent, or Firm* — Andrea L. C. Reid; John P. Rearick; Todd K. Macklin

(57) ABSTRACT

The present invention provides compounds, compositions thereof, and processes for preparing same.

18 Claims, No Drawings

(56) References Cited

U.S. PATENT DOCUMENTS

| | | |
|---|---|---|
| 2005/0075306 A1 | 4/2005 | Schreiber et al. |
| 2006/0211657 A1 | 9/2006 | Singh et al. |
| 2007/0098719 A1 | 5/2007 | Smith et al. |
| 2007/0135461 A1 | 6/2007 | Rodgers et al. |
| 2007/0191405 A1 | 8/2007 | Noronha et al. |
| 2008/0076768 A1 | 3/2008 | Chuckowree et al. |
| 2008/0108636 A1 | 5/2008 | Honigberg et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0136494 A1 | 5/2009 | Ponath et al. |
| 2009/0233903 A1 | 9/2009 | Rodgers et al. |
| 2010/0087440 A1 | 4/2010 | Bajalieh et al. |
| 2010/0150892 A1 | 6/2010 | Han |
| 2010/0197671 A1 | 8/2010 | Burns et al. |
| 2010/0197686 A1 | 8/2010 | Xing et al. |
| 2010/0203056 A1 | 8/2010 | Irving et al. |
| 2010/0233183 A1 | 9/2010 | Triebel et al. |
| 2010/0247554 A1 | 9/2010 | Lemke et al. |
| 2010/0249092 A1 | 9/2010 | Singh et al. |
| 2010/0249126 A1 | 9/2010 | Burger et al. |
| 2010/0279316 A1 | 11/2010 | Gorelik et al. |
| 2011/0008331 A1 | 1/2011 | Triebel |
| 2011/0053941 A1 | 3/2011 | Mautino et al. |
| 2011/0136796 A1 | 6/2011 | Mautino et al. |
| 2011/0165156 A1 | 7/2011 | Dimoudis et al. |
| 2011/0196150 A1 | 8/2011 | Man et al. |
| 2011/0223611 A1 | 9/2011 | Salamone et al. |
| 2011/0274683 A1 | 11/2011 | Wong et al. |
| 2012/0015962 A1 | 1/2012 | Arora et al. |
| 2012/0189639 A1 | 7/2012 | Schebye et al. |
| 2012/0277217 A1 | 11/2012 | Mautino et al. |
| 2012/0283238 A1 | 11/2012 | Romero et al. |
| 2012/0329997 A1 | 12/2012 | Fertig et al. |
| 2013/0005949 A1 | 1/2013 | Fertig et al. |
| 2013/0149236 A1 | 6/2013 | Johnson et al. |
| 2013/0190340 A1 | 7/2013 | Hedstrom et al. |
| 2013/0231328 A1 | 9/2013 | Harriman et al. |
| 2013/0274241 A1 | 10/2013 | Jorand-Lebrun et al. |
| 2014/0018343 A1 | 1/2014 | Romero et al. |
| 2014/0018357 A1 | 1/2014 | Harriman et al. |
| 2014/0018361 A1 | 1/2014 | Harriman et al. |
| 2014/0066625 A1 | 3/2014 | Mautino et al. |
| 2014/0079699 A1 | 3/2014 | Wong et al. |
| 2014/0079706 A1 | 3/2014 | Cannarile et al. |
| 2014/0093511 A1 | 4/2014 | Lonberg et al. |
| 2014/0155379 A1 | 6/2014 | Ho et al. |
| 2014/0194404 A1 | 7/2014 | McElroy et al. |
| 2014/0302523 A1 | 10/2014 | Crews et al. |
| 2014/0329799 A1 | 11/2014 | Seganish et al. |
| 2014/0336363 A1 | 11/2014 | Fertig et al. |
| 2014/0341917 A1 | 11/2014 | Nastri et al. |
| 2014/0356322 A1 | 12/2014 | Crews et al. |
| 2015/0011532 A1 | 1/2015 | Paidi et al. |
| 2015/0018344 A1 | 1/2015 | Paidi et al. |
| 2015/0025093 A1 | 1/2015 | Romero et al. |
| 2015/0045347 A1 | 2/2015 | Dodd et al. |
| 2015/0094305 A1 | 4/2015 | Romero et al. |
| 2015/0133451 A1 | 5/2015 | Yoshida et al. |
| 2015/0141396 A1 | 5/2015 | Crosignani et al. |
| 2015/0191464 A1 | 7/2015 | Santella et al. |
| 2015/0225410 A1 | 8/2015 | Castro et al. |
| 2015/0225449 A1 | 8/2015 | Donnell et al. |
| 2015/0274708 A1 | 10/2015 | Seganish et al. |
| 2015/0274738 A1 | 10/2015 | Gray et al. |
| 2015/0284382 A1 | 10/2015 | Bhide et al. |
| 2015/0284405 A1 | 10/2015 | Trzupek et al. |
| 2015/0291562 A1 | 10/2015 | Crew et al. |
| 2015/0299224 A1 | 10/2015 | Seganish et al. |
| 2015/0329498 A1 | 11/2015 | Romero et al. |
| 2015/0374678 A1 | 12/2015 | Chamberlain et al. |
| 2015/0376167 A1 | 12/2015 | Jorand-Lebrun et al. |
| 2015/0376206 A1 | 12/2015 | Jorand-Lebrun et al. |
| 2016/0002265 A1 | 1/2016 | Jenkins et al. |
| 2016/0022642 A1 | 1/2016 | Crews et al. |
| 2016/0045607 A1 | 2/2016 | Crew et al. |
| 2016/0058872 A1 | 3/2016 | Crew et al. |
| 2016/0145252 A1 | 5/2016 | Jorand-Lebrun et al. |
| 2016/0176916 A1 | 6/2016 | Bradner et al. |
| 2016/0214972 A1 | 7/2016 | Jin et al. |
| 2016/0235730 A1 | 8/2016 | Bradner et al. |
| 2016/0235731 A1 | 8/2016 | Bradner et al. |
| 2016/0243247 A1 | 8/2016 | Bradner et al. |
| 2016/0256468 A1 | 9/2016 | Schafer et al. |
| 2016/0272596 A1 | 9/2016 | Chen et al. |
| 2016/0272639 A1 | 9/2016 | Crew et al. |
| 2016/0311833 A1 | 10/2016 | Bothe et al. |
| 2016/0311839 A1 | 10/2016 | Kelley et al. |
| 2016/0326151 A1 | 11/2016 | Gummadi et al. |
| 2016/0340366 A1 | 11/2016 | Gummadi et al. |
| 2017/0001990 A1 | 1/2017 | Chen et al. |
| 2017/0008896 A1 | 1/2017 | Dahmann et al. |
| 2017/0008904 A1 | 1/2017 | Crew et al. |
| 2017/0022189 A1 | 1/2017 | Zhang |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0152263 A1 | 6/2017 | Gummadi et al. |
| 2017/0152273 A1 | 6/2017 | Merchant et al. |
| 2017/0204093 A1 | 7/2017 | Chan et al. |
| 2017/0247388 A1 | 8/2017 | Altman et al. |
| 2017/0281784 A1 | 10/2017 | Wang et al. |
| 2017/0327469 A1 | 11/2017 | Crew et al. |
| 2017/0369476 A1 | 12/2017 | Chen et al. |
| 2018/0009779 A1 | 1/2018 | Bradner et al. |
| 2018/0015087 A1 | 1/2018 | Liu et al. |
| 2018/0051027 A1 | 2/2018 | Lim et al. |
| 2018/0051028 A1 | 2/2018 | Lim et al. |
| 2018/0051029 A1 | 2/2018 | Lim et al. |
| 2018/0051030 A1 | 2/2018 | Lim et al. |
| 2018/0051035 A1 | 2/2018 | Lim et al. |
| 2018/0085465 A1 | 3/2018 | Bradner et al. |
| 2018/0118733 A1 | 5/2018 | Harling et al. |
| 2018/0127432 A1 | 5/2018 | Trzupek et al. |
| 2018/0134684 A1 | 5/2018 | Bradner et al. |
| 2018/0147202 A1 | 5/2018 | Crew et al. |
| 2018/0169097 A1 | 6/2018 | Hammerman et al. |
| 2018/0186799 A1 | 7/2018 | Gardner et al. |
| 2018/0194724 A1 | 7/2018 | Kemp et al. |
| 2018/0201609 A1 | 7/2018 | Gummadi et al. |
| 2018/0208605 A1 | 7/2018 | Gummadi et al. |
| 2018/0228907 A1 | 8/2018 | Crew et al. |
| 2018/0230157 A1 | 8/2018 | Bacon et al. |
| 2018/0298015 A1 | 10/2018 | Bryan et al. |
| 2018/0327419 A1 | 11/2018 | Bradner et al. |
| 2019/0071415 A1 | 3/2019 | Bradner et al. |
| 2019/0076539 A1 | 3/2019 | Phillips et al. |
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0151295 A1 | 5/2019 | Crew et al. |
| 2019/0151457 A1 | 5/2019 | Bradner et al. |
| 2019/0192532 A1 | 6/2019 | Bradner et al. |
| 2019/0192668 A1 | 6/2019 | Mainolfi et al. |
| 2019/0276474 A1 | 9/2019 | Chan et al. |
| 2019/0374528 A1 | 12/2019 | Gray et al. |
| 2020/0010468 A1 | 1/2020 | Ji et al. |
| 2020/0103418 A1 | 4/2020 | Hackney et al. |
| 2020/0347045 A1 | 11/2020 | Mainolfi et al. |
| 2020/0377469 A1 | 12/2020 | Mainolfi et al. |
| 2021/0002296 A1 | 1/2021 | Mainolfi et al. |
| 2021/0147382 A1 | 5/2021 | Bellenie et al. |
| 2021/0228562 A1 | 7/2021 | Weiss |
| 2021/0323952 A1 | 10/2021 | Mainolfi et al. |
| 2021/0395273 A1 | 12/2021 | Zheng et al. |
| 2022/0273668 A1 | 9/2022 | Gollob et al. |
| 2022/0274993 A1 | 9/2022 | Rong et al. |
| 2023/0122219 A1 | 4/2023 | Weiss et al. |
| 2023/0250110 A1 | 8/2023 | Zheng |
| 2023/0365562 A1 | 11/2023 | Mainolfi et al. |

(56) References Cited

U.S. PATENT DOCUMENTS

2023/0405012 A1 12/2023 Rong et al.
2023/0406866 A1 12/2023 Zheng et al.

FOREIGN PATENT DOCUMENTS

| | | |
|---|---|---|
| WO | WO-2001042246 A2 | 6/2001 |
| WO | WO-2002020740 A2 | 3/2002 |
| WO | WO-2002088112 A1 | 11/2002 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |
| WO | WO-2005113554 A2 | 12/2005 |
| WO | WO-2006029879 A2 | 3/2006 |
| WO | WO-2006078846 A1 | 7/2006 |
| WO | WO-2006105021 A2 | 10/2006 |
| WO | WO-2006122806 A2 | 11/2006 |
| WO | WO-2007005874 A2 | 1/2007 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008039218 A2 | 4/2008 |
| WO | WO-2008109943 A1 | 9/2008 |
| WO | WO-2008118802 A1 | 10/2008 |
| WO | WO-2008132601 A1 | 11/2008 |
| WO | WO-2009009116 A2 | 1/2009 |
| WO | WO-2009044273 A2 | 4/2009 |
| WO | WO-2009073620 A2 | 6/2009 |
| WO | WO-2009114512 A1 | 9/2009 |
| WO | WO-2009132238 A3 | 10/2009 |
| WO | WO-2010019570 A2 | 2/2010 |
| WO | WO-2010077634 A1 | 7/2010 |
| WO | WO-2011028683 A1 | 3/2011 |
| WO | WO-2011043371 A1 | 4/2011 |
| WO | WO-2011056652 A1 | 5/2011 |
| WO | WO-2011070024 A1 | 6/2011 |
| WO | WO-2011090760 A1 | 7/2011 |
| WO | WO-2011107553 A1 | 9/2011 |
| WO | WO-2011109400 A2 | 9/2011 |
| WO | WO-2011131407 A1 | 10/2011 |
| WO | WO-2011140249 A2 | 11/2011 |
| WO | WO-2012003281 A3 | 1/2012 |
| WO | WO-2012007375 A1 | 1/2012 |
| WO | WO-2012032433 A1 | 3/2012 |
| WO | WO-2012068546 A1 | 5/2012 |
| WO | WO-2012078559 A2 | 6/2012 |
| WO | WO-2012084704 A1 | 6/2012 |
| WO | WO-2012097013 A1 | 7/2012 |
| WO | WO-2012129258 | 9/2012 |
| WO | WO-2012142237 A1 | 10/2012 |
| WO | WO-2012145493 A1 | 10/2012 |
| WO | WO-2013042137 A1 | 3/2013 |
| WO | WO-2013066729 A1 | 5/2013 |
| WO | WO-2013079174 A1 | 6/2013 |
| WO | WO-2013087699 A1 | 6/2013 |
| WO | WO-2013106535 A1 | 7/2013 |
| WO | WO-2013106612 A1 | 7/2013 |
| WO | WO-2013106614 A1 | 7/2013 |
| WO | WO-2013106641 A1 | 7/2013 |
| WO | WO-2013106643 A2 | 7/2013 |
| WO | WO-2013106646 A2 | 7/2013 |
| WO | WO-2013119716 A1 | 8/2013 |
| WO | WO-2013132044 A1 | 9/2013 |
| WO | WO-2013169264 A1 | 11/2013 |
| WO | WO-2014008218 A1 | 1/2014 |
| WO | WO-2014008992 A1 | 1/2014 |
| WO | WO-2014011902 A1 | 1/2014 |
| WO | WO-2014011906 A2 | 1/2014 |
| WO | WO-2014011911 A2 | 1/2014 |
| WO | WO-2014036357 A1 | 3/2014 |
| WO | WO-2014044622 A1 | 3/2014 |
| WO | WO-2014058685 A1 | 4/2014 |
| WO | WO-2014058691 A1 | 4/2014 |
| WO | WO-2014063061 A1 | 4/2014 |
| WO | WO-2014074660 A1 | 5/2014 |
| WO | WO-2014074675 A1 | 5/2014 |
| WO | WO-2014108452 A1 | 7/2014 |
| WO | WO-2014121931 A1 | 8/2014 |
| WO | WO-2014121942 A1 | 8/2014 |
| WO | WO-2014142237 A1 | 9/2014 |
| WO | WO-2014143672 A1 | 9/2014 |
| WO | WO-2015048281 A1 | 4/2015 |
| WO | WO-2015068856 A1 | 5/2015 |
| WO | WO-2015071393 A1 | 5/2015 |
| WO | WO-2015091426 A1 | 6/2015 |
| WO | WO-2015103453 A1 | 7/2015 |
| WO | WO-2015104662 A1 | 7/2015 |
| WO | WO-2015104688 A1 | 7/2015 |
| WO | WO-2015150995 A1 | 10/2015 |
| WO | WO-2015160845 A3 | 10/2015 |
| WO | WO-2015164374 A1 | 10/2015 |
| WO | WO-2015193846 A1 | 12/2015 |
| WO | WO-2016011390 A1 | 1/2016 |
| WO | WO-2016053769 A1 | 4/2016 |
| WO | WO-2016053770 A1 | 4/2016 |
| WO | WO-2016053771 A1 | 4/2016 |
| WO | WO-2016053772 A1 | 4/2016 |
| WO | WO-2016081679 A1 | 5/2016 |
| WO | WO-2016105518 A1 | 6/2016 |
| WO | WO-2016118666 A1 | 7/2016 |
| WO | WO-2016144844 A1 | 9/2016 |
| WO | WO-2016144846 A1 | 9/2016 |
| WO | WO-2016144847 A1 | 9/2016 |
| WO | WO-2016144848 A1 | 9/2016 |
| WO | WO-2016144849 A1 | 9/2016 |
| WO | WO-2016149668 A1 | 9/2016 |
| WO | WO-2016169989 A1 | 10/2016 |
| WO | WO-2016172560 A1 | 10/2016 |
| WO | WO-2016174183 A1 | 11/2016 |
| WO | WO-2016197032 A1 | 12/2016 |
| WO | WO-2016197114 A1 | 12/2016 |
| WO | WO-2016210034 A1 | 12/2016 |
| WO | WO-2017004133 A1 | 1/2017 |
| WO | WO-2017004134 | 1/2017 |
| WO | WO-2017007612 A1 | 1/2017 |
| WO | WO-2017009798 A1 | 1/2017 |
| WO | WO-2017009806 A1 | 1/2017 |
| WO | WO-2017011371 A1 | 1/2017 |
| WO | WO-2017011590 A1 | 1/2017 |
| WO | WO-2017030814 A1 | 2/2017 |
| WO | WO-2017033093 A1 | 3/2017 |
| WO | WO-2017049068 A1 | 3/2017 |
| WO | WO-2017059280 A1 | 4/2017 |
| WO | WO-2017079267 A1 | 5/2017 |
| WO | WO-2017108723 A2 | 6/2017 |
| WO | WO-2017117473 A1 | 7/2017 |
| WO | WO-2017117474 A1 | 7/2017 |
| WO | WO-2017127430 A1 | 7/2017 |
| WO | WO-2017161119 A1 | 9/2017 |
| WO | WO-2017176708 A1 | 10/2017 |
| WO | WO-2017176957 A1 | 10/2017 |
| WO | WO-2017176958 A1 | 10/2017 |
| WO | WO-2017197036 A1 | 11/2017 |
| WO | WO-2017197046 A1 | 11/2017 |
| WO | WO-2017197051 A1 | 11/2017 |
| WO | WO-2017197055 A1 | 11/2017 |
| WO | WO-2017197056 A1 | 11/2017 |
| WO | WO-2017201449 A1 | 11/2017 |
| WO | WO-2017205762 A1 | 11/2017 |
| WO | WO-2017205766 A1 | 11/2017 |
| WO | WO-2017207385 A1 | 12/2017 |
| WO | WO-2017211924 A1 | 12/2017 |
| WO | WO-2018052058 A1 | 3/2018 |
| WO | 2018071606 | 4/2018 |
| WO | WO-2018089736 A1 | 5/2018 |
| WO | WO-2018098367 A1 | 5/2018 |
| WO | WO-2018119441 A1 | 6/2018 |
| WO | WO-2018144649 A1 | 8/2018 |
| WO | WO-2018209012 A1 | 11/2018 |
| WO | WO-2018237026 A1 | 12/2018 |

(56) References Cited

FOREIGN PATENT DOCUMENTS

| | | |
|---|---|---|
| WO | WO-2019043214 A1 | 3/2019 |
| WO | WO-2019060693 A1 | 3/2019 |
| WO | WO-2019060742 A1 | 3/2019 |
| WO | 2019094772 A1 | 5/2019 |
| WO | WO-2019084026 A1 | 5/2019 |
| WO | WO-2019084030 A1 | 5/2019 |
| WO | WO-2019099868 A1 | 5/2019 |
| WO | WO-2019099926 A1 | 5/2019 |
| WO | 2019111218 A1 | 6/2019 |
| WO | WO-2019133531 A1 | 7/2019 |
| WO | WO-2019140380 A1 | 7/2019 |
| WO | WO-2019140387 A1 | 7/2019 |
| WO | WO-2019160915 A1 | 8/2019 |
| WO | WO-2019165229 A1 | 8/2019 |
| WO | WO-2019236483 | 12/2019 |
| WO | WO-2020010177 A1 | 1/2020 |
| WO | WO-2020010210 A1 | 1/2020 |
| WO | WO-2020010227 A1 | 1/2020 |
| WO | WO-2020018788 A1 | 1/2020 |
| WO | 2020038415 A1 | 2/2020 |
| WO | 2020041331 A1 | 2/2020 |
| WO | 2020092907 A1 | 5/2020 |
| WO | 2020113233 A1 | 6/2020 |
| WO | WO-2020251969 A1 | 12/2020 |
| WO | WO-2020251971 A1 | 12/2020 |
| WO | WO-2020251972 A1 | 12/2020 |
| WO | WO-2020251974 A1 | 12/2020 |
| WO | WO-2020264490 A1 | 12/2020 |
| WO | WO-2020264499 A1 | 12/2020 |
| WO | WO-2021011631 A1 | 1/2021 |
| WO | WO-2021011634 A1 | 1/2021 |
| WO | WO-2021011868 A1 | 1/2021 |
| WO | WO-2021011871 A1 | 1/2021 |
| WO | WO-2021053555 A1 | 3/2021 |
| WO | WO-2021119159 A1 | 6/2021 |
| WO | WO-2021127190 A1 | 6/2021 |
| WO | WO-2021127278 A1 | 6/2021 |
| WO | WO-2021127283 A2 | 6/2021 |
| WO | 2021158634 A1 | 8/2021 |
| WO | 2021247899 A1 | 12/2021 |
| WO | 20210247897 A1 | 12/2021 |
| WO | 20210257914 A1 | 12/2021 |
| WO | 20220174268 A1 | 8/2022 |
| WO | 20220174269 A1 | 8/2022 |
| WO | 2023076556 A1 | 5/2023 |
| WO | 20230147594 A2 | 8/2023 |

OTHER PUBLICATIONS

Chou and Talalay, "Quantitative analysis of dose-effect relationships: the combined effects of multiple drugs or enzyme inhibitors," Adv Enzyme Regul., 1984, 22:27-55.

Cushing et al., "Interleukin 1/Toll-like receptor-induced autophosphorylation activates interleukin 1 receptor-associated kinase 4 and controls cytokine induction in a cell type-specific manner," J Biol Chem., 2014, 289(15):10865-10875.

De Nardo et al. "Interleukin-1 receptor-associated kinase 4 (IRAK4) plays a dual role in myddosome formation and Toll-like receptor signaling," J Biol Chem., 2018, 293(39):15195-15207.

Fisher et al., "The complexities inherent in attempts to decrease drug clearance by blocking sites of CYP-mediated metabolism," Curr Opin Drug Discov Devel., 2006, 9(1):101-109.

Foster, "Deuterium isotope effects in the metabolism of drugs and xenobiotics: implications for drug design," Advances in Drug Research, 1985, 14:1-40.

Fukuto et al., "Determination of the mechanism of demethylenation of (methylenedioxy)phenyl compounds by cytochrome P450 using deuterium isotope effects," J Med Chem., 1991, 34(9):2871-2876.

Huang et al., "A Chemoproteomic Approach to Query the Degradable Kinome Using a Multi-kinase Degrader", Cell Chem Biol., 2018, 25(1):88-99.

Kushner et al., "Pharmacological uses and perspectives of heavy water and deuterated compounds," Can J Physiol Pharmacol. 1999, 77(2):79-88.

Patra and Choi, "Recent Progress in the Molecular Recognition and Therapeutic Importance of Interleukin-1 Receptor-Associated Kinase 4," Molecules, 2016, 21(11):1529.

Slavin et al., "Identification of highly potent and selective Interlukin-1 receptor associated kinase 4 (IRAK4) degraders for the treatment suppurativa", Feb. 2020, 1 page. Retrived from https://www.kymeratx.com/wp-content/uploads/2020/07/EHSF_Kymera_2020_Final.pdf.

Stieger et al., "Recrystallization of Active Pharmaceutical Ingredients", Crystallization—Science and Technology, 2012, pp. 183-201.

PCT International Search Report and Written Opinion from PCT/US2023/060645, dated Mar. 31, 2023, 25 pages.

PCT International Search Report and Written Opinion from PCT/US2021/035745, dated Sep. 27, 2021, 13 pages.

PCT International Search Report and Written Opinion from PCT/US2021/035747, dated Sep. 27, 2021, 24 pages.

PCT International Search Report and Written Opinion from PCT/US2022/070662, dated Apr. 18, 2022, 10 pages.

PCT International Search Report and Written Opinion from PCT/US2022/070664, dated May 3, 2022, 14 pages.

PCT International Search Report received from PCT/US2023/061673, dated Jul. 25, 2023, 4 pages.

PCT International Preliminary Report on Patentability from PCT/US2021/035745, dated Dec. 15, 2022, 6 pages.

PCT International Preliminary Report on Patentability from PCT/US2021/035747, dated Dec. 15, 2022, 6 pages.

PCT International Preliminary Report on Patentability from PCT/US2020/065752, dated Jun. 30, 2022, 7 pages.

PCT International Preliminary Report on Patentability received from PCT/US2020/065628, dated Jun. 30, 2022, 9 pages.

PCT International Preliminary Report on Patentability from PCT/US2021/037952, dated Dec. 29, 2022, 9 pages.

PCT International Search Report and Written Opinion from PCT/US2021/037952, dated Sep. 29, 2021, 11 pages.

PCT International Preliminary Report on Patentability from PCT/US2021/071048, dated Feb. 9, 2023, 7 pages.

PCT International Search Report and Written Opinion from PCT/US2021/071048, dated Nov. 5, 2021, 9 pages.

PCT International Preliminary Report on Patentability from PCT/US2022/070662, dated Aug. 24, 2023, 7 pages.

PCT International Preliminary Report on Patentability from PCT/US2022/070664, dated Aug. 24, 2023, 7 pages.

Adams et al., "Big opportunities for small molecules in immuno-oncology," Nat Rev Drug Discov. 2015;14(9):603-22.

Aruri et al., "Metal-free Cross-Dehydrogenative Coupling of HN-azoles with a-C(sp3)-H Amides via C—H Activation and Its Mechanistic and Application Studies," J Org Chem. 2017;82(2):1000-1012.

Balasubramanian et al., "Abstract 3646: Novel IRAK-4 inhibitors exhibit highly potent anti-proliferative activity in DLBCL cell lines with activating MYD88 L265P mutation," AACR 106th Annual Meeting 2015; Apr. 18-22, 2015; Philadelphia, PA.

Berge et al., "Pharmaceutical salts," J Pharm Sci. 1977;66(1):1-19.

Berndsen et al., "New insights into ubiquitin E3 ligase mechanism," Nat Struct Mol Biol. 2014;21(4):301-7.

Boichenko et al., "A FRET-Based Assay for the Identification and Characterization of Cereblon Ligands," J Med Chem. 2016;59(2):770-4.

Buckley et al., "IRAK-4 inhibitors. Part 1: a series of amides," Bioorg Med Chem Lett. 2008;18(11):3211-4.

Buckley et al., "IRAK-4 inhibitors. Part II: a structure-based assessment of imidazo[1,2-a]pyridine binding," Bioorg Med Chem Lett. 2008;18(11):3291-5.

Buckley et al., "IRAK-4 inhibitors. Part III: A series of imidazo[1,2-a]pyridines," Bioorg Med Chem Lett. 2008;18(12):3656-60.

Cameron et al., "Loss of Interleukin Receptor-Associated Kinase 4 Signaling Suppresses Amyloid Pathology and Alters Microglial Phenotype in a Mouse Model of Alzheimer's Disease," J Neurosci. 2012;32(43):15112-23.

Cario, "Therapeutic Impact of Toll-like Receptors on Inflammatory Bowel Diseases: A Multiple-edged Sword," Inflamm Bowel Dis. 2008; 14(3):411-21.

(56) References Cited

OTHER PUBLICATIONS

CAS STN Abstract, RN 1787975-60-3 (Pub. Jun. 24, 2015).
CAS STN Abstract, RN 1795294-81-3 (Pub. Jul. 6, 2015).
CAS STN Abstract, RN 1795451-20-5 (Pub. Jul. 6, 2015).
CAS STN Abstract, RN 1795527-49-9 (Pub. Jul. 6, 2015).
CAS STN Abstract, RN 1871221-08-7 (Pub. Feb. 21, 2016).
CAS STN Abstract, RN 1878956-45-6 (Pub. Mar. 3, 2016).
CAS STN Abstract, RN 1878983-55-1 (Pub. Mar. 3, 2016).
CAS STN Abstract, RN 742039-47-0 (Pub. Sep. 10, 2004).
CAS STN Abstract, RN 779303-42-3 (Pub. Nov. 12, 2004).
Chang et al., "What is the functional role of the thalidomide binding protein cereblon?" Int J Biochem Mol Biol. 2011;2(3):287-94.
Charrier et al., "Desulfonylative Radical Ring Closure onto Aromatics. A Modular Route to Benzazepin-2-ones and 5-Arylpiperidin-2-ones," Org. Lett. 2012, 14(8): 2018-2021.
Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders," J Med Chem. 2015;58(1):96-110.
Chiang et al., "Immune Complex-Mediated Cell Activation from Systemic Lupus Erythematosus and Rheumatoid Arthritis Patients Elaborate Different Requirements for IRAK1/4 Kinase Activity across human Cell Types," J Immunol. 2011;186(2):1279-88.
Cohen, "Targeting protein kinases for the development of anti-inflammatory drugs," Curr Opin Cell Biol. 2009;21(2):17-24.
Connolly et al., "Complexities of TGF-beta Targeted Cancer Therapy," Int J Biol Sci. 2012;8(7):964-978.
Contino-Pepin et al., "Preliminary biological evaluations of new thalidomide analogues for multiple sclerosis application," Bioorg Med Chem Lett. 2009;19(3):878-81.
Crews, "Targeting the Undruggable Proteome: The Small Molecules of My Dreams," Chem Biol. 2010;17(6):551-5.
Cushing et al., "IRAK4 kinase controls Toll-like receptor induced inflammation through the transcription factor IRF5 in primary human monocytes," J Biol Chem. 2017;292(45):18689-18698.
Dalbeth et al., "Hyperuricaemia and gout: state of the art and future perspectives," Ann Rheum Dis. 2014;73(9):1598-600.
Degorce et al.,"Optimization of permeability in a series of pyrrolotriazine inhibitors of IRAK4," Bioorg Med Chem. 2018;26(4):913-924.
Deshaies and Joazeiro, "RING domain E3 ubiquitin ligases," Annu Rev Biochem. 2009;78:399-434.
Devi et al., "Medicinal Attributes of Imidazo[1,2-a]pyridine Derivatives: An Update," Curr Top Med Chem, 2016, 16(26):2963-2994.
Dinarello, "IL-1: Discoveries, controversies and future directions," Eur J Immunol. 2010:40(3):599-606.
Dinarello, "Interleukin 1 and interleukin 18 as mediators of inflammation and the aging process," Am J Clin Nutr. 2006; 83(suppl):447S-55S.
Dinarello, "Interleukin-18 and the Pathogenesis of Inflammatory Diseases," Semin Nephrol. 2007;27(1):98-114.
Dudhgaonkar et al., "Selective IRAK4 Inhibition Attenuates Disease in Murine Lupus Models and Demonstrates Steroid Sparing Activity," J Immunol. 2017; 198(3):1308-1319.
Dunne et al., "IRAK1 and IRAK4 Promote Phosphorylation, Ubiquitation, and Degradation of MyD88 Adaptor-like (Mal)," J Biol Chem. 2010;285(24):18276-82.
El-Gamal et al., "Recent Advances of Colony-Stimulating Factor-1 Receptor (CSF-1R) Kinase and Its Inhibitors," J Med Chem. 2018;61(13):5450-5466.
Fischer et al., "Structure of the DDB1-CRBN E3 ubiquitin ligase in complex with thalidomide," Nature. 2014;512(7512):49-53.
Flannery et al., "The interleukin-1 receptor-associated kinases: Critical regulators of innate immune signaling," Biochem Pharmacol. 2010;80(12):1981-91.
Gearing, "Targeting toll-like receptors for drug development: a summary of commercial approaches," Immunol Cell Biol. 2007;85(6):490-4.

Geyer and Müller-Ladner, "Actual status of antiinterleukin-1 therapies in rheumatic diseases," Curr Opin Rheumatol. 2010;22(3):246-51.
Gottipati et al., "IRAK1: A critical signaling mediator of innate immunity," Cell Signal. 2008;20(2):269-76.
Hagner et al., "CC-122, a pleiotropic pathway modifier, mimics an interferon response and has antitumor activity in DLBCL," Blood. 2015;126(6):779-89.
Heightman et al., "Structure-Activity and Structure-Conformation Relationships of Aryl Propionic Acid Inhibitors of the Kelch-like ECH-Associated Protein 1/Nuclear Factor Erythroid 2-Related Factor 2 (KEAP1/NRF2) Protein-Protein Interaction," J. Med. Chem., 2019, 62(9): 4683-4702.
Hennessy et al., "Targeting Toll-like receptors: emerging therapeutics?" Nat Rev Drug Discov. 2010;9(4):293-307.
Hines et al., "MDM2-Recruiting PROTAC Offers Superior, Synergistic Antiproliferative Activity via Simultaneous Degradation of BRD4 and Stabilization of p53," Cancer Res. 2019;79(1):251-262.
Hoffman et al., "Efficacy and Safety of Rilonacept (Interleukin-1 Trap) in Patients with Cryopyrin-Associated Periodic Syndromes," Arthritis Rheum. 2008;58(8):2443-5.
Iannello et al., "Role of Interleukin-18 in the Development and Pathogenesis of AIDS," AIDS Rev. 2009;11(3):115-25.
Iconomou and Saunders, "Systematic approaches to identify E3 ligase substrates," Biochem J. 2016;473(22):4083-4101.
Iriyama et al., "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011.
Ito et al., "Identification of a primary target of thalidomide teratogenicity," Science. 2010;327(5971):1345-50.
Kargbo, "Protac Degradation of IRAK4 for the Treatment of Cancer," ACS Med. Chem. Lett., 2019, 10(10):1370-1371.
Kelly et al., "Selective interleukin-1 receptor-associated kinase 4 inhibitors for the treatment of autoimmune disorders and lymphoid malignancy," J Exp Med. 2015;212(13):2189-201.
Kester et al., "Optimization of Benzodiazepinones as Selective Inhibitors of the X-Linked Inhibitor of Apoptosis Protein (XIAP) Second Baculovirus IAP Repeat (BIR2) Domain," J Med Chem. 2013;56(20):7788-803.
Kim et al., "A critical role for IRAK4 kinase activity in Toll-like receptor-mediated innate immunity," J Exp Med. 2007;204(5):1025-36.
Kondo et al., "Renoprotective effects of novel interleukin-1 receptor-associated kinase 4 inhibitor AS2444697 through anti-inflammatory action in 5/6 nephrectomized rats," Naunyn Schmiedebergs Arch Pharmacol. 2014;387(10):909-19.
Kou et al., "Effects of RuPeng15 Powder (RPP15) on Monosodium Urate Crystal-Induced Gouty Arthritis in Rats," Evid Based Complement Alternat Med. 2015;2015:527019.
Koziczak-Holbro et al., "IRAK-4 Kinase Activity Is Required for Interleukin-1 (IL-1) Receptor- and Toll-like Receptor 7-mediated Signaling and Gene Expression," J Biol Chem. 2007;282(18):13552-60.
Krönke et al., "Lenalidomide causes selective degradation of IKZF1 and IKZF3 in multiple myeloma cells" Science. 2014;343(6168):301-305.
Ku et al., "Selective predisposition to bacterial infections in IRAK-4-deficient children: IRAK-4-dependent TLRs are otherwise redundant in protective immunity," J Exp Med. 2007;204(10):2407-2422.
Kubo-Murai et al., "IRAK-4-dependent Degradation of IRAK-1 is a Negative Feedback Signal for TLR-mediated NF-κB Activation," J Biochem. 2008; 143(3):295-302.
Kuppers, "IRAK inhibition to shut down TLR signaling in autoimmunity and MyD88-dependent lymphomas," J Exp Med. 2015;212(13):2184.
Lebakken et al., "A Fluorescence Lifetime Based Binding Assay to Characterize Kinase Inhibitors," J Biomol Screen. 2007;12(6):828-41.
Lee et al., "Discovery of Clinical Candidate 1-{[2S,3S,4S)-3-ethyl-4-fluoro-5-oxopyrrolidin-2-yl]methoxy}-7-methoxyisoquinoine-6-carboxamide (PF-06650833), a Potent, Selective Inhibitor of

(56) References Cited

OTHER PUBLICATIONS

Interleukin-1 Receptor Associated Kinase 4 9IRAK4), by Fragment-Based Drug Design," J Med Chem. 2017;60(13):5521-5542.
Li et al., "Genome-wide and functional annotation of human E3 ubiquitin ligases identifies MULAN, a mitochondrial E3 that regulates the organelle's dynamics and signaling," PLoS One. 2008;3(1):e1487.
Li et al., "IRAK-4: A novel member of the IRAK family with the properties of an IRAK-kinase," Proc Natl Acad Sci USA. 2002;99(8):5567-72.
Li et al., "Targeting interleukin-1 receptor-associated kinase for human hepatocellular carcinoma," J Exp Clin Cancer Res. 2016;35(1):140.
Li, "IRAK4 in TLR/IL-1R signaling: Possible clinical applications," Eur J Immunol. 2008;38(3):614-8.
Lim et al., "Discovery of 5-Amino-N-(1H-pyrazol-4-yl)pyrazolo[1,5-a]pyrimidine-3-carboxamide Inhibitors of IRAK4," ACS Med Chem Lett. 2015;6(6):683-688.
Lin et al., "Helical assembly in the MyD88-IRAK4-IRAK2 complex in TLR /IL-1R signalling," Nature. 2010:465(7300):885-90.
Lu et al., "Discovery of a Keap1-dependent peptide PROTAC to knockdown Tau by ubiquitination-proteasome degradation pathway," Euro J Med Chem. 2018;46:251-9.
Lu et al., "Hijacking the E3 Ubiquitin Ligase Cereblon to Efficiently Target BRD4," Chem Biol. 2015;2(6):755-63.
Lu et al., "The myeloma drug lenalidomide promotes the cereblon-dependent destruction of Ikaros proteins," Science. 2014;343(6168):305-309.
Lust et al., "Induction of a Chronic Disease State in patients With Smoldering of Indolent Multiple Myeloma by Targeting Interleukin 1β-Induced Interleukin 6 Production and the Myeloma Proliferative Component," Mayo Clin Proc. 2009;84(2):114-22.
Martinon et al., "Gout-associated uric acid crystals activate the NALP3 inflammasome," Nature. 2006;440(7081):237-41.
Maschera et al., "Overexpression of an enzymatically inactive interleukin-1-receptor-associated kinase activates nuclear factor-kB," Biochem J. 1999;339(Pt2):227-31.
Matyskiela et al., "A Cereblon Modulator (CC-220) with Improved Degradation of Ikaros and Aiolos," J Med Chem. 2018;61(2):535-542.
McElroy et al., "Discovery and hit-to-lead optimization of 2,6-diaminopyrimidine Inhibitors of interleukin-1 receptor-associated kinase 4," Bioorg Med Chem Lett. 2015;25(9):1836-41.
Mcelroy et al., "Potent and Selective Amidopyrazole Inhibitors of IRAK4 That Are Efficacious in a Rodent Model of Inflammation," ACS Med Chem Lett. 2015;6(6):677-682.
Moynagh, "The Pellino Family: Irak E3 ligases with emerging roles in innate immune signalling," Trends Immunol. 2009, 30(1): 33-42.
Muller et al., "Amino-Substituted Thalidomide Analogs: Potent Inhibitors of TNF -? Production," Bioorg Med Chem Lett. 1999;9(11):1625-30.
Ngo et al., "Oncogenically active MYD88 mutations in human lymphoma," Nature. 2011;470(7332):115-9.
Nunes et al., "Targeting IRAK4 for Degradation with PROTACTSs," ACS Med Chem Lett. 2019;10(7):1081-1085.
Ohoka et al., "In Vivo Knockdown of Pathogenic Proteins via Specific and Nongenetic Inhibitor of Apoptosis Protein (IAP)-dependent Protein Erasers (SNIPERs)," J Bio Chem. 2017;292(11):4556-4570.
Ohoka et al., "Development of Small Molecule Chimeras That Recruit AhR E3 Ligase to Target Proteins,"ACS Chem. Biol. 2019, 14(12):2822-2832.
Okazaki et al., "A rheostat for immune responses: the unique properties of PD-1 and their advantages for clinical application," Nat. Immunol. 2013; 14(12): 1212-1218.
PCT International Preliminary Report on Patentability from PCT/US2018/067304, dated Jun. 30, 2020.
PCT International Preliminary Report on Patentability from PCT/US2019/040462, dated Jan. 21, 2021.
PCT International Search Report and Written Opinion from PCT/US2018/052181, dated Feb. 26, 2019.
PCT International Search Report and Written Opinion from PCT/US2018/052242, dated Jan. 30, 2019.
PCT International Search Report and Written Opinion from PCT/US2018/067304, dated Apr. 30, 2019.
PCT International Search Report and Written Opinion from PCT/US2019/013481, dated Mar. 15, 2019.
PCT International Search Report and Written Opinion from PCT/US2019/013491, dated Mar. 18, 2019.
PCT International Search Report and Written Opinion from PCT/US2019/040462, dated Sep. 20, 2019.
PCT International Search Report and Written Opinion from PCT/US2019/040520, dated Nov. 13, 2019.
PCT International Search Report and Written Opinion from PCT/US2019/040545, dated Oct. 21, 2019.
PCT International Search Report and Written Opinion from PCT/US2019/064070, dated Apr. 6, 2020.
PCT International Search Report and Written Opinion from PCT/US2020/026869, dated Jul. 27, 2020.
PCT International Search Report and Written Opinion from PCT/US2020/036913, dated Oct. 26, 2020.
PCT International Search Report and Written Opinion from PCT/US2020/036916, dated Oct. 26, 2020.
PCT International Search Report and Written Opinion from PCT/US2020/036918, dated Oct. 26, 2020.
PCT International Search Report and Written Opinion from PCT/US2020/036921, dated Oct. 26, 2020.
PCT International Search Report and Written Opinion from PCT/US2020/040101, dated Nov. 10, 2020.
PCT International Search Report and Written Opinion from PCT/US2020/040125, dated Nov. 13, 2020.
PCT International Search Report and Written Opinion from PCT/US2020/042105, dated Nov. 20, 2020.
PCT International Search Report and Written Opinion from PCT/US2020/042109, dated Dec. 10, 2020.
PCT International Search Report and Written Opinion from PCT/US2020/042530, dated Oct. 16, 2020.
PCT International Search Report and Written Opinion from PCT/US2020/042534, dated Oct. 26, 2020.
PCT International Search Report and Written Opinion from PCT/US2020/064061, dated Apr. 9, 2021.
PCT International Search Report and Written Opinion from PCT/US2020/065628, dated May 28, 2021.
PCT International Search Report and Written Opinion from PCT/US2020/065752, dated Mar. 25, 2021.
PCT International Search Report and Written Opinion from PCT/US2020/065757, dated May 28, 2021.
PCT International Search Report and Written Opinion from PCT/US2020/066859, dated May 4, 2021.
PCT International Search Report and Written Opinion from PCT/US2021/062640, dated Feb. 8, 2022.
PCT International Search Report and Written Opinion from PCT/US2022/048163, dated Mar. 10, 2023.
Picard et al., "Clinical features and outcome of patients with IRAK-4 and MyD88 deficiency," Medicine (Baltimore). 2010;89(6):403-425.
Picard et al., "Inherited human IRAK-4 deficiency: an update," Immunol Res. 2007;38(1-3):347-52.
Piya et al., "BRD4 Proteolysis Targeting Chimera (PROTAC) Leads to Sustained Degradation of BRD4 with Broad Activity Against Acute Leukemias and Overcomes Stroma Mediated Resistance by Modulating Surface Expression of CXCR4," Blood. 2016; 126(23): 675-676.
Powers et al., "Discovery and initial SAR of inhibitors of interleukin-1 receptor-associated kinase-4," Bioorg Med Chem Lett. 2006;16(11):2842-5.
Priyadarshini et al., "Copper catalyzed oxidative cross-coupling of aromatic amines with 2-pyrrolidinone: a facile synthesis of N-aryl-r-amino-r-lactams," Tetrahedron. 2014;70(36): 6068-6074.
Pubmed Compound Summary for CID 101524675, "(2R)-3-Fluoro-2-(2-methylpropyl)-3-phenyl-1,3-azasilinan-6-one," *U.S. National*

(56) References Cited

OTHER PUBLICATIONS

*Library of Medicine*, created Dec. 18, 2015, https://pubchem.ncbi.nlm.nih.gov/compound/101524675. Date Accessed: Sep. 5, 2019 (5 pages).
Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).
Pubmed Compound Summary for CID 110491408, 3-(5-Amino-2-oxo-3H-benzimidazol-1-piperidine-2,6-dione, U.S. Library of Medicine, created Jan. 18, 2016, https://pubchem.ncbi.nlm.nih.gov/compound/110491408. Date Accessed: Feb. 25, 2020 (7 pages).
Pubmed Compound Summary for CID 110491555, 3-(6-Amino-2-oxo-3H-benzimidazol-1-piperidine-2,6-dione, U.S. Library of Medicine, created Jan. 18, 2016, https://pubchem.ncbi.nlm.nih.gov/compound/110491555. Date Accessed: Feb. 25, 2020 (7 pages).
Pubmed Compound Summary for CID 115370667, "5-(2-Oxoimidazolidin-1-yl)piperidin-2-one." U.S. National Library of Medicine, created Oct. 22, 2012, https://pubchem.ncbi.nlm.nih.gov/compound/115370667. Date Accessed: Feb. 25, 2020 (10 pages).
Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).
Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Accessed: Feb. 25, 2020 (6 pages).
Pubmed Compound Summary for CID 5426, "Thalidomide," created Mar. 25, 2005.
Pubmed Compound Summary for CID 63661260, "5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).
Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).
Pubmed Compound Summary for CID 65967733, "3-(2,5-Dioxo-3-phenylpyrrolidin-1-yl)piperidine-2,6-dione," U.S. National Library of Medicine, created Dec. 24, 2015, https://pubchem.ncbi.nlm.nih.gov/compound/65967733. Date Accessed: Feb. 25, 2020 (7 pages).
Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).
Pubmed Compound Summary for CID 67258040, "[1-(9H-Fluoren-9-yl)-1-(6-oxopiperidin-3-ethyl] hydrogen carbonate," U.S. National Library of Medicine, Nov. 30, 2012, https://pubchem.ncbi.nlm.nih.gov/compound/67258040. Date Accessed: Feb. 25, 2020 (9 pages).
Pubmed Compound Summary for CID 83543479, "5(Aminomethyl)-5-(1H-indol-3-yl)piperidin-2-one," *U.S. National Library of Medicine*, created Oct. 20, 2014, https://pubchem.ncbi.nlm.nih.gov/compound/83543479. Date Accessed: Feb. 25, 2020 (6 pages).
Pubmed Compound Summary for CID 84036945, 1-Piperidin-3-yl-3H-indol-2-one, *U.S. Library of Medicine*, created Oct. 20, 2014, https://pubchem.ncbi.nlm.nih.gov/compound/84036945. Date Accessed: Feb. 25, 2020 (7 pages).
Pubmed Compound Summary for CID 86793742, 3-[(6-chloro-1H-1,3-benzodiazol-2-yl)sulfanyl]piperidine-2,6-dione, created Feb. 7, 2015, https://pubchem.ncbi.nlm.nih.gov/compound/86793742. Date Accessed: Jan. 10, 2022.
Pubmed Compound Summary for CID 91648396, 3-[(4-Fluorophenyl)sulfanyl]piperidine-2,6-dione, created Mar. 20, 2015, https://pubchem.ncbi.nlm.nih.gov/compound/91648396#section=Structures. Date Accessed: Jan. 10, 2022.
Pubmed Compound Summary for CID 99784232, (3S)-3-(4-fluorophenyl)sulfanylpiperidine-2,6- dione, created Dec. 11, 2015, https://pubchem.ncbi.nlm.nih.gov/compound/99784232. Date Accessed: Jan. 10, 2022.
Raina et al., "Chemical Inducers of Targeted Protein Degradation," J Biol Chem. 2010;285(15):11057-60.
Ramirez et al., "Defining causative factors contributing in the activation of hedgehog signaling in diffuse large B-cell lymphoma," Leuk. Res. 2012;36(10):1267-73.
Rokosz et al., "Kinase inhibitors as drugs for chronic inflammatory and immunological diseases: progress and challenges," Expert Opin Ther Targets. 2008;12(7):883-903.
Ronnebaum et al., "Synthesis of 1, 2, 3-triazole 'click' analogues of thalidomide," Tetrahedron. 2016;72(40): 6136-6141.
Ross et al., "Bispecific T cell engager (BITE®) antibody constructs can mediate bystander tumor cell killing," PLoS One. 2017; 12(8): e0183390.
Rostovtsev et al., "A Stepwise Huisgen Cycloaddition Process: Copper(I)-Catalyzed Regioselective "Ligation" of Azides and Terminal Alkynes," Angew Chem Int Ed Engl. 2002;41(14):2596-9.
Rusnac et al., "Recognition of the Diglycine C-End Degron by CRL2 KLHDC2 Ubiquitin Ligase," Mol. Cell. 2018, 72(5):813-822.e4.
Schnnekloth et al., "Chemical approaches to controlling intracellular protein degradation," Chembiochem. 2005;6(1):40-46.
Scott et al., "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphoma," J Med Chem. 2017;60(24):10071-10091.
Seganish et al., "Discovery and Structure Enabled Synthesis of 2,6-diaminopyrimidine-4-one IRAK4 Inhibitors," ACS Med Chem Lett. 2015;6(8):942-947.
Seganish et al., "Initial optimization and series evolution of diaminopyrimidine inhibitors of interleukin-1 receptor associated kinase 4," Bioorg Med Chem Lett. 2015;25(16):3203-3207.
Seitz et al., "Sulfenylation and Halogenation of Di-and Trianions Derived from Substituted Glutarimides," Synthetic Communications. 1977;7(6):367-374.
Sen et al., "Transcriptional signaling by double-stranded RNA: role of TLR3," Cytokine Growth Factor Rev. 2005;16(1):1-14.
Shanmugasundaram et al., "A modular PROTAC design for target destruction using a degradation signal based on a single amino acid," J Biol Chem. 2019;294(41):15172-15175.
Smith et al., "Identification of quinazoline based inhibitors of IRAK4 for the treatment of inflammation," Bioorg Med Chem Lett. 2017;27(12):2721-2726.
So et al., "A pilot study of IL-1 inhibition by anakinra in acute gout," Arthritis Res Ther. 2007;9(2):R28.
Song et al., "The kinase activities of interleukin-e receptor associated kinase (IRAK)-1 and 4 are redundant in the control of inflammatory cytokine expression in human cells," Mol Immunol. 2009;46(7):1458-66.
Spradin et al., "Harnessing the Anti-Cancer Natural Product Nimbolide for Targeted Protein Degradation," bioRxiv.org, https://www.biorxiv.org/content/biorxiv/early/2019/04/09/436998.full.pdf. Date Accessed, Oct. 3, 2019.
Spratt et al., "RBR E3 ubiquitin ligases: new structures, new insights, new question," Biochem J. 2014;458(3);421-37.
Stewart et al., "Efforts toward elucidating Thalidomide's molecular target: an expedient synthesis of the first Thalidomide biotin analogue," Organic & Biomolecular Chemistry. 2010;8(18): 4059-4062.
Sun et al., "Carbohydrate and protein immobilization onto solid surfaces by sequential Diels-Alder and azide-alkyne cycloadditions," Bioconjug Chem. 2006;17(1):52-7.
Suzuki et al., "IRAK-4 as the central TIR signaling mediator in innate immunity," Trends Immunol. 2002;23(10):503-6.
Suzuki et al., "Severe impairment of interleukin-1 and Toll-like receptor signalling in mice lacking IRAK-4," Nature. 2002;416(6882):750-6.
Swantek et al., "IL-1 Receptor-Associated Kinase Modulates Host Responsiveness to Endotoxin, Journal of Immunology 164: 4301-4306," J Immunol. 2000;164(8):4301-6.

(56) References Cited

OTHER PUBLICATIONS

Terkeltaub et al., "The interleukin 1 inhibitor rilonacept in treatment of chronic gouty arthritis: results of a placebo-controlled, monosequence crossover, non-randomised, single-blind pilot study," Ann Rheum Dis. 2009;68(10):1613-7.

Terkeltaub, "Update on gout: new therapeutic strategies and options," Nat Rev Rheumatol. 2010;6(1):30-8.

Tong et al., "Targeted Protein Degradation via a Covalent Reversible Degrader Based on Bardoxolone", ChemRxiv. First Posted Online: Apr. 2, 2020.

Toogood, "Small molecule immuno-oncology therapeutic agents," Bioorg. Med. Chem. Lett. 2018;28(3):319-329.

Torres et al., "Hyperalgesia, synovitis and multiple biomarkers of inflammation are suppressed by interleukin 1 inhibition in a novel animal model of gouty arthritis," Ann Rheum Dis. 2009;68(10):1602-8.

Toure and Crews, "Small-Molecule PROTACS: New Approaches to Protein Degradation," Angew Chem Int Ed Engl. 2016;55(6):1966-73.

Treon et al., "Whole genome sequencing reveals a widely expressed mutation (MYD88 L265P) with oncogenic activity in Waldenström's Macroglobulinemia" 53rd ASH Annual Meeting, San Diego, California, Dec. 10-13, 2011 [abstract].

Trøseid et al., "The role of interleukin-18 in the metabolic syndrome," Cardiovasc Diabetol. 2010;9:11.

Tumey et al., "Identification and optimization of indolo[2,3-c]quinoline inhibitors of IRAK4," Bioorg Med Chem Lett. 2014;24(9):2066-72.

Uehara et al., "Selective degradation of splicing factor CAPER? by anticancer sulfonamides," Nat Chem Biol. 2017;13(6):675-680.

Varfolomeev et al., "IAP antagonists induce autoubiquitination of c-IAPs, NF-kappaB activation, and TNFalpha-dependent apoptosis," Cell. 2007;131(4):669-81.

Vollmer et al., "The mechanism of activation of IRAK1 and IRAK1 by interleukin-1 and Toll-like receptor agonists," Biochem J. 2017;474(12):2027-2038.

Wang et al., "Crystal Structure of IRAK-4 Kinase in Complex with Inhibitors: Serine/Threonine Kinase with Tyrosine as a Gatekeeper," Structure. 2006; 14(12):1835-44.

Wang et al., "Discovery of potent, selective, and orally bioavailable inhibitors of interleukin-1 receptor-associated kinase 4," Bioorg Med Chem Lett. 2015;25(23):5546-5550.

Wang et al., "IRAK-4 Inhibitors for Inflammation," Curr Top Med Chem. 2009;9(8):724-37.

Wang et al., "Roles of F-box proteins in cancer," Nat Rev Cancer. 2014; 14(4):233-47.

Ward et al., "Covalent Ligand Screening Uncovers a RNF4 E3 Ligase Recruiter for Targeted Protein Degradation Applications," bioRxiv.org, https://www.biorxiv.org/content/biorxiv/early/2018/11/16/439125.full.pdf. Date Accessed, Oct. 3, 2019 (24 pages).

Weaver, "Epidemiology of gout," Cleve Clin J Med. 2008;75 Suppl 5:S9-12.

Winter et al., "Selective Target Protein Degradation via Phthalimide Conjugation," Science. 2015;348(6241):1376-1381.

Xia and Chen, "Iron-catalyzed N-alkylation of azoles via cleavage of an sp3 C—H bond adjacent to a nitrogen atom," J Org Chem. 2012;77(20):9366-73.

Xu et al., "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011.

Yang et al., "Disruption of MYD88 pathway signaling leads to loss of constitutive IRAK1, Nk-κb and JAK/STAT signaling and induces apoptosis of cells expressing the MYD88 L265P mutation in Waldenstrom's Macroglobulinemia" 53rd ASH Annual Meeting, San Diego, California, Dec. 10-13, 2011.

Yang et al., "Exploiting synthetic lethality for the therapy of ABC diffuse large B cell lymphoma," Cancer Cell. 2012;21(6):723-37.

Zhang et al., "Constitutive IRAK4 Activation Underlies Poor Prognosis and Chemoresistance in Pancreatic Ductal Adenocarcinoma," Clin Cancer Res. 2017;23(7):1748-1759.

Zhang et al., "Electrophilic PROTACs that degrade nuclear proteins by engaging DCAF16," bioRxiv.org, https://www.biorxiv.org/content/biorxiv/early/2018/10/15/443804.full.pdf. Date Accessed, Oct. 3, 2019.

Zhou et al., "Targets of curcumin," Curr Drug Targets. 2011;12(3):332-347.

Zinc 170596280, Date Added Aug. 8, 2015, https://zinc.docking.org/substances/ZINC000170596280/. Date Accessed: Jan. 10, 2022.

Zou et al., "PD-L1 (B7-H1) and PD-1 pathway blockage for cancer therapy: Mechanisms, response biomarkers, and combinations," Sci Transl. Med. 2016;8(328):328rv4.

Harvey, et al., "Management of organic impurities in small molecule medicinal products: Deriving safe limits for use in early development", Regulatory Toxicology and Pharmacology, Mar. 2017, 84:116-123.

McElroy, "Interleukin-1 receptor-associated kinase 4 (IRAK4) inhibitors: an updated patent review," Expert Opinion on Therapeutic Patents, 2019, 29(4): 243-259.

PCT International Search Report and Written Opinion received from PCT/US2023/083863, dated Apr. 2, 2024.

PCT International Search Report and Written Opinion received from PCT/US2024/019048, dated Jun. 14, 2024.

IRAK4 DEGRADERS AND SYNTHESIS THEREOF

CROSS REFERENCE TO RELATED APPLICATIONS

This application claims the benefit of priority to U.S. Appl. No. 63/263,274, filed Oct. 29, 2021, the entire contents of which is herein incorporated by reference.

TECHNICAL FIELD OF THE INVENTION

The present invention relates to IRAK4 degrader 5-((1R,4R)-2-oxa-5-azabicyclo[2.2.1]heptan-5-yl)-N-(3-(difluoromethyl)-1-((1 r,4R)-4-((4-((3-(1-(2,6-dioxopiperidin-3-yl)-3-methyl-2-oxo-2,3-dihydro-1H-benzo [d] imidazol-4-yl)prop-2-yn-1-yl)oxy)piperidin-1-yl)methyl)cyclohexyl)-1 H-pyrazol-4-yl)pyrazolo[1,5-a]pyrimidine-3-carboxamide, synthesis thereof, and compositions thereof.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

UPP plays a key role in the degradation of short-lived regulatory proteins important in a variety of basic cellular processes, including regulation of the cell cycle, modulation of cell surface receptors and ion channels, and antigen presentation. Interleukin-1 receptor-associated kinase-4 (IRAK4) is a key component of the myddosome, a multiprotein complex involved in innate immunity that mediates signaling through toll-like receptors (TLRs) and interleukin (IL)-1 receptors (Patra and Choi, Molecule 2016, 21(11): 1529). The IRAK4 protein is ubiquitously expressed across multiple different tissue types, including skin, lymphoid tissue, bone marrow, gastrointestinal (GI) tract and lung. The function of IRAK4 is dependent both on its kinase activity and on its scaffolding properties, which is required for the assembly of the myddosome complex following TLR or IL-1R engagement and myeloid differentiation factor 88 (MyD88) activation (De Nardo et al., J. Bio. Chem. 2018, 293(39):15195; Cushing et al., J. Bio. Chem. 2014, 289(15): 10865). The NF-kB activation is particularly dependent on the scaffolding function of IRAK4 and is a key driver of cellular proliferation and proinflammatory cytokine and chemokine production mediated by myddosome activation.

Various IRAK4 degraders, including 5-((1R,4R)-2-oxa-5-azabicyclo[2.2. 1]heptan-5-yl)-N-(3-(difluoromethyl)-1-((1 r,4R)-4-((4-((3-(1-(2,6-dioxopiperidin-3-yl)-3-methyl-2-oxo-2,3-dihydro-1H-benzo[d]imidazol-4-yl)prop-2-yn-1-yl)oxy)piperidin-1-yl)methyl)cyclohexyl)-1 H-pyrazol-4-yl)pyrazolo[1,5-a]pyrimidine-3-carboxamide, have been described previously, for example, in WO 2019/133531 and WO 2020/010227, the contents of which are incorporated herein by reference in their entireties. There remains an unmet need for improved synthesis of such compounds.

SUMMARY OF THE INVENTION

It has now been found that a composition of 5-((1R,4R)-2-oxa-5-azabicyclo[2.2.1]heptan-5-yl)-N-(3-(difluoromethyl)-1-((1 r,4R)-4-((4-((3-(1-(2,6-dioxopiperidin-3-yl)-3-methyl-2-oxo-2,3-dihydro-1H-benzo [d] imidazol-4-yl)prop-2-yn-1-yl)oxy)piperidin-1-yl)methyl)cyclohexyl)-1 H-pyrazol-4-yl)pyrazolo[1,5-a]pyrimidine-3-carboxamide (compound I-1 herein) or a pharmaceutically acceptable salt thereof may contain a number of impurities.

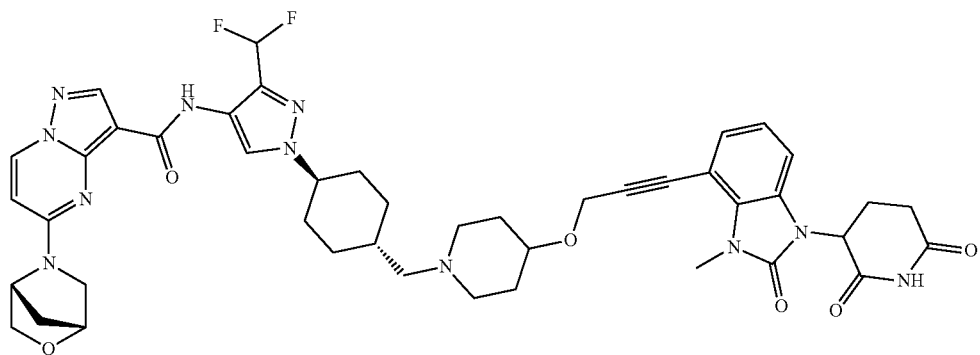

I-1

In one aspect, the present invention provides a composition comprising compound I-1 and one or more impurity compounds selected from the group consisting of:

I-2
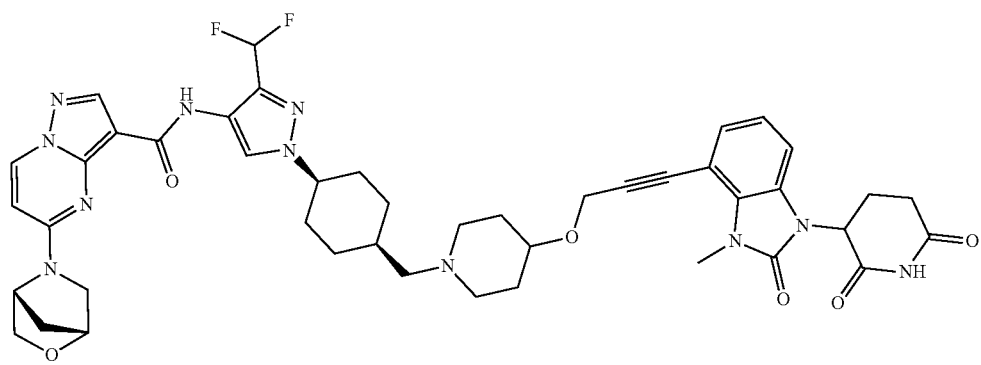
I-3
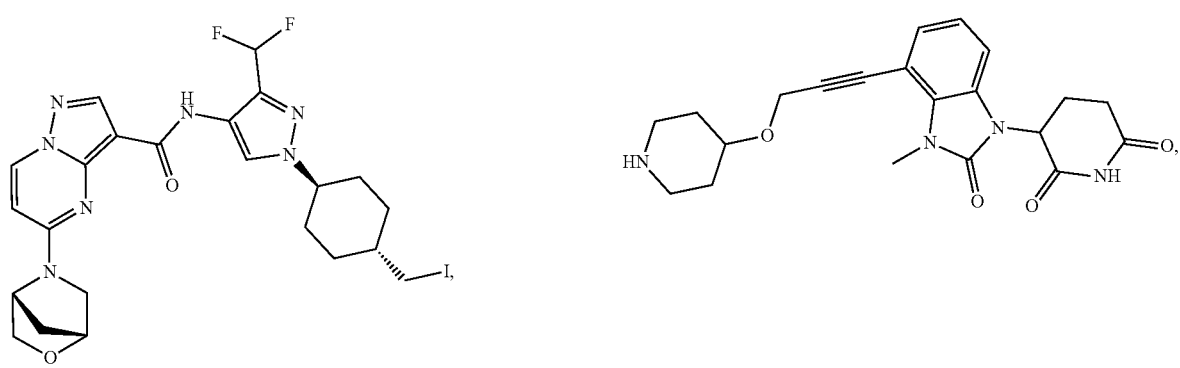
I-4
I-5
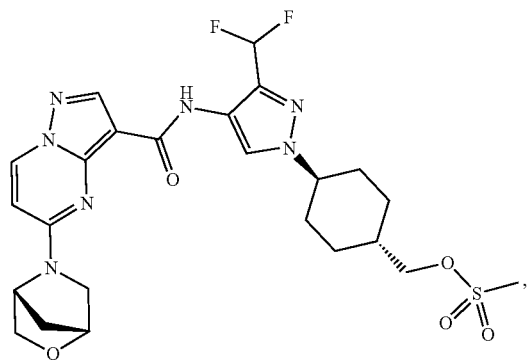
I-6
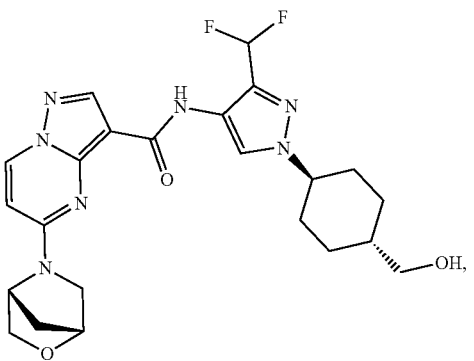
I-7
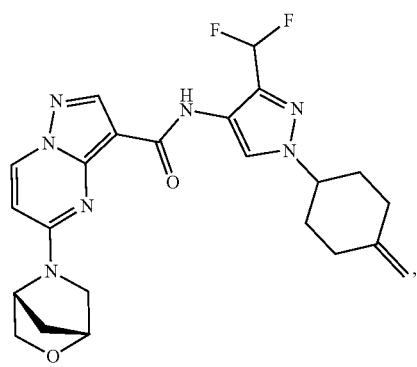

I-8

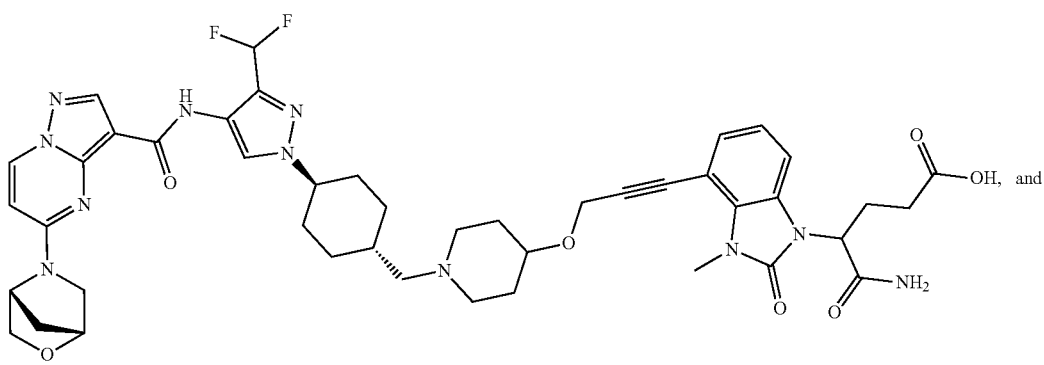

I-9

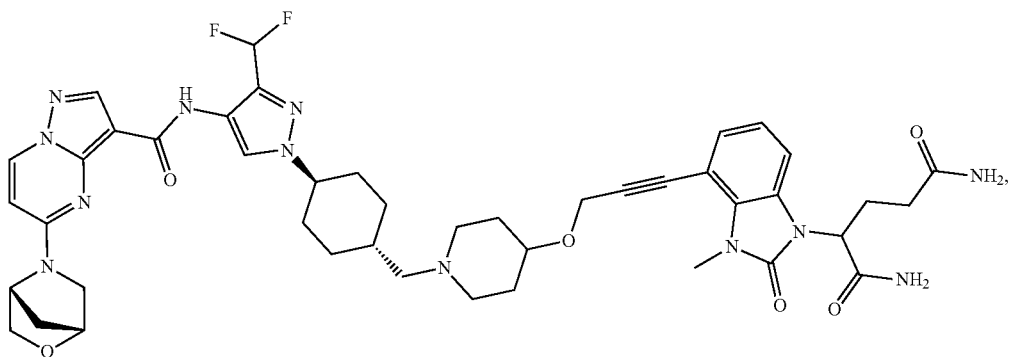

Compound I-1 or a pharmaceutically acceptable salts thereof, and pharmaceutical compositions thereof, as described in the instant application, are useful for treating an autoimmune/autoinflammatory disease. In some aspects, the autoimmune/autoinflammatory disease is a cutaneous autoimmune/autoinflammatory disease selected from atopic dermatitis (AD), rheumatoid arthritis (RA), and hidradenitis suppurativa (HS).

In another aspect, the present invention provides a method for synthesizing compound I-1, or a pharmaceutically acceptable salt thereof, and related intermediates.

These and other aspects of this disclosure will be apparent upon reference to the following detailed description. To this end, various references are set forth herein which describe in more detail certain background information and procedures and are each hereby incorporated by reference in their entirety.

DETAILED DESCRIPTION OF THE INVENTION

1. General Description of Certain Embodiments of the Invention

One of ordinary skill in the art will appreciate that impurity profile of an active pharmaceutical agent ("API" or "drug substance") is an important aspect of any pharmaceutical drug product. As such, impurities arising from synthesis or degradation are useful in that they allow for the monitoring of API purity and adherence to regulatory standards.

In certain embodiments, the present invention provides compositions comprising compound I-1:

I-1

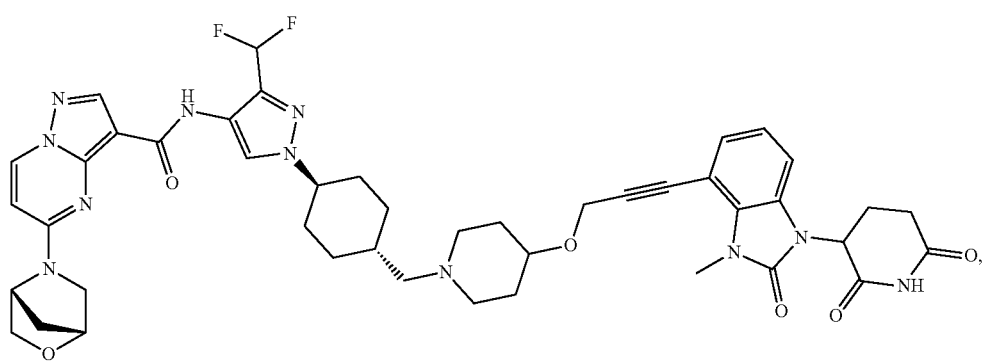

and one or more impurity compounds (i.e., impurities) therein.

Compound I-1 is a potent, highly selective, orally administered heterobifunctional small molecule therapeutic targeting IRAK4 and the E3 ligase CRBN to mediate the selective degradation of IRAK4 via the ubiquitin-proteasome system.

In some embodiments, compound I-1 is in crystalline form. In some embodiments, compound I-1 is in HCl salt form. In some embodiments, compound I-1 is in a crystalline HCl salt form. In some embodiments, the crystalline HCl salt form of compound I-1 is polymorph Form A, as described in WO 2021/247899 the content of which is incorporated herein by reference in its entirety. In some embodiments, the polymorph Form A of compound I-1 is characterized by having one or more main peaks in its X-ray powder diffraction pattern selected from those at about 14.1, about 17.0, about 17.3, about 19.0, about 21.0, about 21.2 and about 23.3 degrees 2-theta.

In certain embodiments, the present invention provides methods for treating an autoimmune/autoinflammatory disease or a hematological malignancy in a patient comprising administering to the patient a pharmaceutical composition comprising compound I-1 as described herein. In some embodiments, the composition comprises compound I-1, and one or more impurities selected from the group consisting of I-2, I-3, I-4, I-5, I-6, I-7, I-8, and I-9, or a pharmaceutically acceptable salt thereof, as described herein.

In the following disclosure, certain specific details are set forth in order to provide a thorough understanding of various embodiments. However, one skilled in the art will understand that the methods and uses described herein may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "Including, but not limited to." Further, headings provided herein are for convenience only and do not interpret the scope or meaning of the claimed invention.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. In some embodiments, a carbocyclic ring may be a 5-12 membered bicyclic, bridged bicyclic, or spirocyclic ring. A carbocyclic ring may include one or more oxo (=O) or thioxo (=S) substituent. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

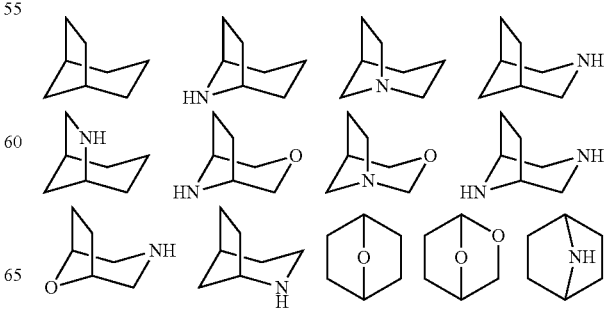

-continued

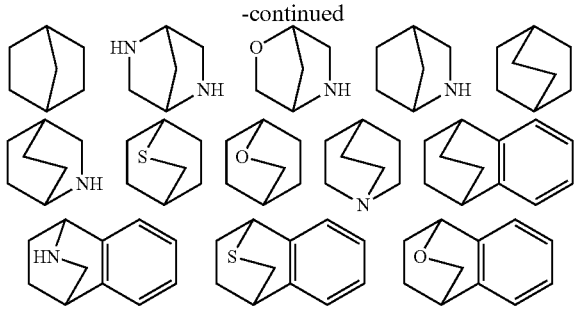

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quatemized form of any basic nitrogen or; a substitutable nitrogen of a heterocyclic ring, for example N (as in 3,4-dihydro-2H-pyrrolyl), NH (as in pyrrolidinyl) or NR (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

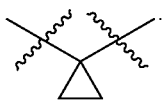 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "arylenyl" refers to bivalent aryl groups (e.g., phenylenyl).

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 a electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quatemized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic, bridged bicyclic, or spirocyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted. The term "heteroarylenyl" refers to bivalent heteroaryl groups (e.g., pyridylenyl).

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. In some embodiments, a heterocyclic ring may be a 5-12 membered bicyclic, bridged bicyclic, or spirocyclic ring. A heterocyclic ring may include one or more oxo (=O) or thioxo (=S) substituent. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the disclosure may contain "substituted" moieties. In general, the term "substituted" means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^°$; —$(CH_2)_{0-4}OR^°$; —$O(CH_2)_{0-4}R^°$, —O—$(CH_2)_{0-4}C(O)OR^°$; —$(CH_2)_{0-4}CH(OR^°)_2$; —$(CH_2)_{0-4}SR^°$; —$(CH_2)_{0-4}Ph$, which may be substituted with $R^°$; —$(CH_2)_{0-4}O(CH_2)_{0-1}Ph$ which may be substituted with $R^°$; —CH=CHPh, which may be substituted with $R^°$; —$(CH_2)_{0-4}O(CH_2)_{0-1}$— pyridyl which may be substituted with $R^°$; —$NO_2$; —CN; —$N_3$; —$(CH_2)_{0-4}N(R^°)_2$; —$(CH_2)_{0-4}N(R^°)C(O)R^°$; —$N(R^°)C(S)R^°$; —$(CH_2)_{0-4}N(R^°)C(O)NR^°_2$; $N(R^°)C(S)NR^°_2$; —$(CH_2)_{0-4}N(R^°)C(O)OR^°$; —$N(R^°)N(R^°)C(O)R^°$; —$N(R^°)N(R^°)C(O)NR^°z$; —$N(R^°)N(R^°)C(O)OK^°$; —$(CH_2)_{0-4}C(O)R^°$; —C(S)R^°; —$(CH_2)_{0-4}C(O)OR^°$; —$(CH_2)_{0-4}C(O)SR^°$; —$(CH_2)_{0-4}C(O)OSiR^°_3$; —$(CH_2)_{0-4}OC(O)R^°$; —OC(OXCH_2)_{0-4}S R^°$; —$(CH_2)_{0-4}SC(O)R^°$; —$(CH_2)_{0-4}C(O)NR^°_2$; —C(S)NR^°z; —C(S)SR^°; —SC(S)SR^°, —$(CH_2)_{0-4}OC(O)NR^°z$; —C(O)N(OR^°)R^°; —C(O)C(O)R^°; —C(O)CH_2C(O)R^°$; —C(NOR^°)R^°; —$(CH_2)_{0-4}SSR^°$; —$(CH_2)_{0-4}S(O)_2R^°$; —$(CH_2)_{0-4}S(O)_2OR^°$; —$(CH_2)_{0-4}OS(O)_2R^°$; —$S(O)_2NR^°_2$; —$(CH_2)_{0-4}S(O)R^°$; —$N(R^°)S(O)_2NR^°_2$; —$N(R^°)S(O)_2R^°$; —$N(OR^°)R^°$; —$C(NH)NR^°z$; —$P(O)_2R^°$; —$P(O)R^°_2$; —$OP(O)R^°_2$; —$OP(O)(OR^°)z$; $SiR^°_3$; —$(C_{1-4}$ straight or branched alkylene)O—$N(R^°)_2$; or —$(C_{1-4}$ straight or branched alkylene)C(O)O—$N(R^°)_2$, wherein each $R^°$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^°$ (or the ring formed by taking two independent occurrences of $R^°$ together with their intervening atoms), are independently halogen, —$(CH_2)_{0-2}R^•$, -(haloR^•), —$(CH_2)_{0-2}OH$, —$(CH_2)_{0-2}OR'$, —$(CH_2)_{0-2}CH(OR^•)_2$; —$O(haloR^•)$, —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR'$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR^•$, or —SSR wherein each $R^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^°$ include =O and =S.

Suitable divalent substituents on a saturated carbon atom of an "optionally substituted" group include the following: =O, =S, =NNR_2, =NNHC(O)R^•, =NNHC(O)OR^•, =NNHS(O)_2R^•, =NR^•, =NOR^•, —$O(C(R^•_2))_{2-3}O$—, or —$S(C(R^•_2))_{2-3}S$—, wherein each independent occurrence of R is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^•2)_{2-3}O$—, wherein each independent occurrence of $R^•$ is selected from hydrogen, $C_{1-4}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^•$ include halogen, —$R^•$, -(haloR^•), —OH, —OR^•, —$O(haloR^•)$, —CN, —C(O)OH, —C(O)OR^•, —$NH_2$, —$NHR^•$, —$NR^•_2$, or —$NO_2$, wherein each $R^•$ is unsubstituted or where preceded by "halo" is substituted only with one or more halogens, and is independently $C_1$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^t$, —$NR^t_2$, —$C(O)R^t$, —$C(O)OR^t$, —$C(O)C(O)R^t$, —$C(O)CH_2C(O)R^t$, —$S(O)_2R^t$, —$S(O)_2NR^t_2$, —$C(S)NR^t_2$, —$C(NH)NR^t_2$, or —$N(R^t)S(O)_2R^t$; wherein each $R^t$ is independently hydrogen, $C_1$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^t$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^t$ are independently halogen, —$R^•$, -(haloR^•), OH, —OR', —$O(haloR^•)$, —CN, —C(O)OH, —C(O)OR^•, —$NH_2$, —$NHR^•$, —$NR^•_2$, or —$NO_2$, wherein each $R^•$ is unsubstituted or where preceded by "halo" is substituted only with one or more halogens, and is independently $C_1$ aliphatic, —CH$_2$Ph, —O(CH$_2$)a1Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the terms "about" or "approximately" have the meaning of within 20% of a given value or range. In some embodiments, the term "about" refers to within 20%, 19%, 18%, 17%, 16%, 15%, 14%, 13%, 12%, 11%, 10%, 9%, 8%, 7%, 6%, 5%, 4%, 3%, 2%, or 1% of a given value.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

As used herein, the phrase "leaving group" refers to a functional group that is displaced from a molecule during a chemical reaction. Leaving groups include halogens, as well sulfonate groups, such as tosylate, triflate, and mesylate.

As used herein, the term "patient" or "subject" means a mammal, preferably a human.

As used herein, a "therapeutically effective amount" means an amount of a substance (e.g., a therapeutic agent, composition, and/or formulation) that elicits a desired biological response. In some embodiments, a therapeutically effective amount of a substance is an amount that is sufficient, when administered as part of a dosing regimen to a subject suffering from or susceptible to a disease, condition, or disorder, to treat, diagnose, prevent, and/or delay the onset of the disease, condition, or disorder. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, condition, or disorder is the amount that alleviates, ameliorates, relieves, inhibits, prevents, delays onset of, reduces severity of and/or reduces incidence of one or more symptoms or features of the disease, condition, or disorder. In some embodiments, a "therapeutically effective amount" is at least a minimal amount of a compound, or composition containing a compound, which is sufficient for treating one or more symptoms associated with autoimmune/autoinflammatory disease in a patient.

The terms "treat" or "treating," as used herein, refers to partially or completely alleviating, inhibiting, delaying onset of, preventing, ameliorating and/or relieving a disease or disorder, or one or more symptoms of the disease or disorder. As used herein, the terms "treatment," "treat," and "treating" refer to partially or completely alleviating, inhibiting, delaying onset of, preventing, ameliorating and/or relieving a disease or disorder, or one or more symptoms of the disease or disorder, as described herein. In some embodiments, treatment may be administered after one or more symptoms have developed. In some embodiments, the term "treating" includes preventing or halting the progression of a disease or disorder. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence. Thus, in some embodiments, the term "treating" includes preventing relapse or recurrence of a disease or disorder.

The expression "unit dosage form" as used herein refers to a physically discrete unit of therapeutic formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

As used herein, the term "area percent of the HPLC" or "area percent HPLC" refers to the area percentage of a peak in a HPLC chromatogram. The terms "area percent of the HPLC" or "area percent HPLC" are used to indicate the amount of a compound in a composition. In some embodiments, an area percent of the HPLC, or an area percentage HPLC, of compound I-1 refers to the area of the compound I-1 peak(s) relative to the total area of the compound I-1 and impurity compounds peaks in the composition in a HPLC chromatogram. In some embodiments, an area percent of the HPLC, or an area percentage HPLC, of an impurity compound refers to the area of the impurity compound peak(s) relative to the total area of the compound I-1 and impurity compounds peaks in the composition in a HPLC chromatogram. In some embodiments, an area percent of the HPLC, or an area percentage HPLC, of total impurity compounds refers to the area of all impurity compounds peak(s) relative to the total area of the compound I-1 and impurity compounds peaks in the composition in a HPLC chromatogram. In some embodiments, an area percentage is relative to the area of compound I-1 in a HPLC chromatogram. In some embodiments, a HPLC method is as described in the examples, e.g., column: Zorbax Eclipse Plus C18, 150×3.0 mm, 3.5 μm; mobile phases: 0.04% TFA in water and 0.02% TFA in acetonitrile; detection: UV at 225 nm; column temperature: 40° C.; pump program: gradient; flow rate: 0.9 mL/min; and sample preparation: 0.4 mg/mL in diluent=50:50:0:2 acetonitrile:water:TFA. In some embodiments, a HPLC method is as described in Table 7 in the examples.

The term "weight percent" or "wt %" as used herein refers to the weight percentage of a component calculated based on the non salt form. A weight percentage of compound I-1 refers to the weight percent of compound I-1 relative to the total weight of a composition. In some embodiments, a weight percentage of an impurity, or total organic impurities, refers to the weight percent of the impurity, or total organic impurities, relative to the total weight of a composition. In some embodiments, a weight percentage of an impurity, or total organic impurities, refers to the weight percent of the impurity, or total organic impurities, relative to the weight of compound I-1 in a composition.

3. Description of Exemplary Compounds

It has now been found that certain impurity compounds may be present in a composition comprising compound I-1.

According to one aspect, the present invention provides an impurity compound, which is any one of the following below in Table 1.

TABLE 1

Exemplary Compounds

TABLE 1-continued
Exemplary Compounds
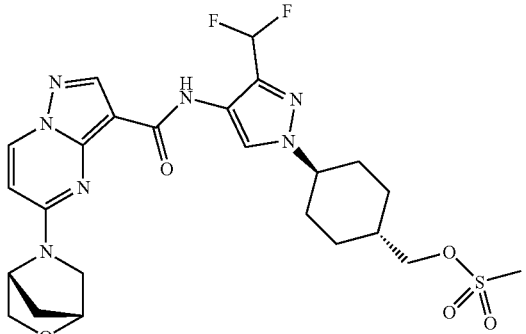
I-5
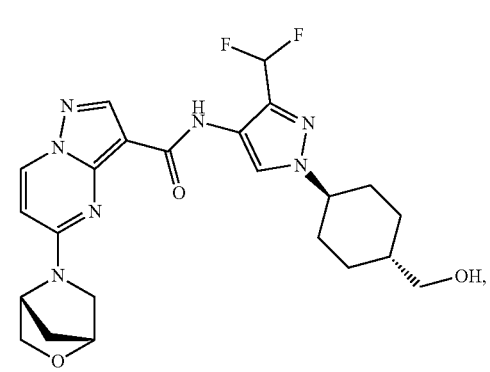 [SMILES: O=C(Nc1cn([C@H]2CC[C@H](CO)CC2)nc1C(F)F)c1cnn2ccc(N3C[C@H]4C[C@@H]3CO4)nc12]
I-6
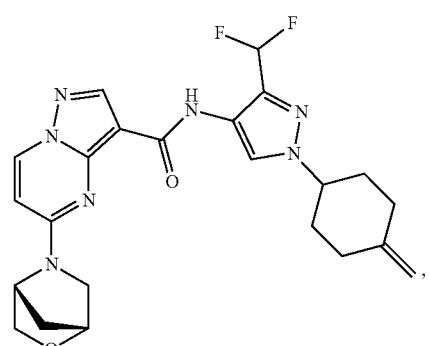
I-7
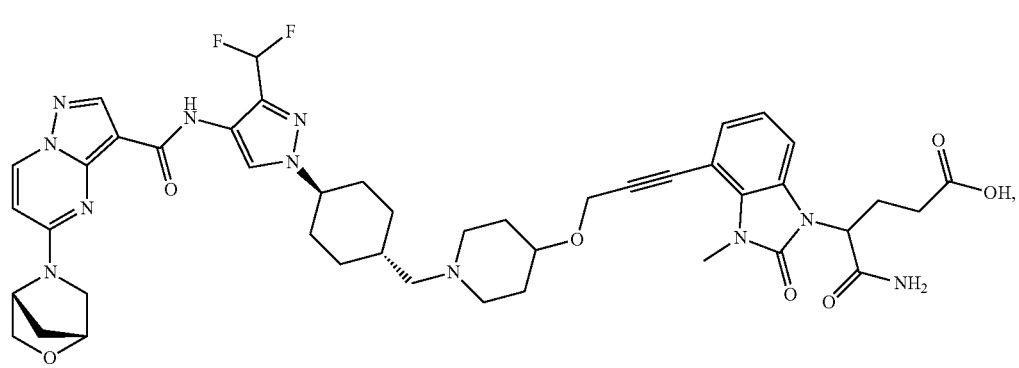 [SMILES: Cn1c(=O)n(C(CCC(=O)O)C(N)=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21]
I-8

TABLE 1-continued
Exemplary Compounds
I-9
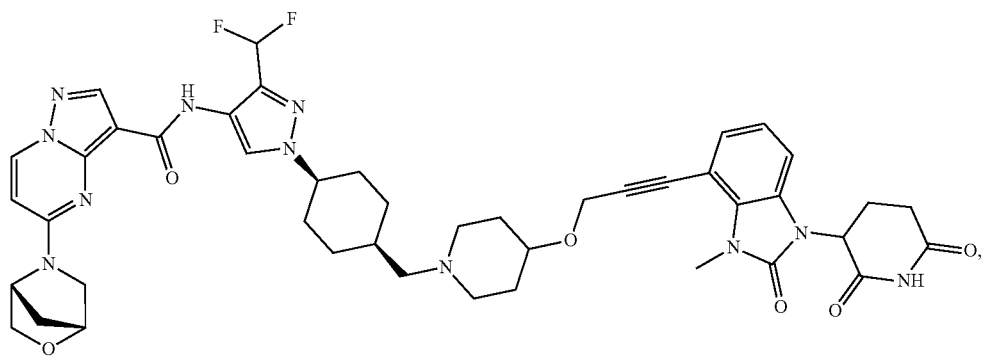 [SMILES: Cn1c(=O)n(C2CCC(=O)NC2=O)c2cccc(C#CCOC3CCN(C[C@H]4CC[C@@H](n5cc(NC(=O)c6cnn7ccc(N8C[C@H]9C[C@@H]8CO9)nc67)c(C(F)F)n5)CC4)CC3)c21]
or a pharmaceutically acceptable salt thereof.
In some embodiments, the present invention provides compound I-2:
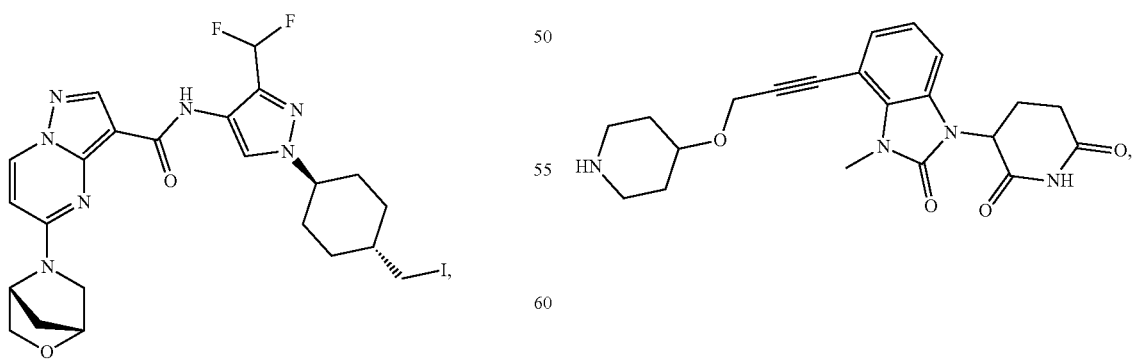
or a pharmaceutically acceptable salt thereof.
In some embodiments, the present invention provides compound I-3:

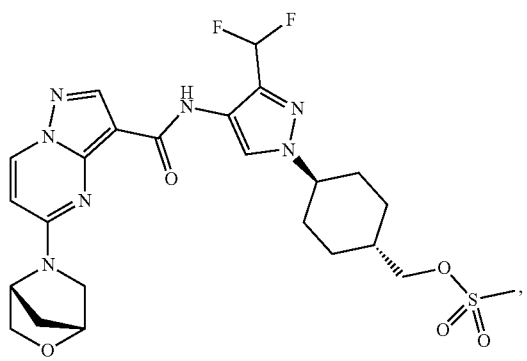 [SMILES: CS(=O)(=O)OC[C@H]1CC[C@H](n2cc(NC(=O)c3cnn4ccc(N5C[C@H]6C[C@@H]5CO6)nc34)c(C(F)F)n2)CC1]

or a pharmaceutically acceptable salt thereof.

In some embodiments, the present invention provides compound I-6:

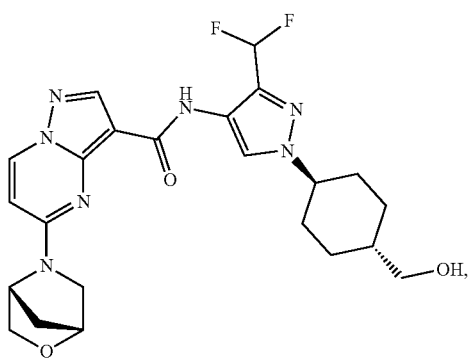 [SMILES: O=C(Nc1cn([C@H]2CC[C@H](CO)CC2)nc1C(F)F)c1cnn2ccc(N3C[C@H]4C[C@@H]3CO4)nc12]

or a pharmaceutically acceptable salt thereof.

In some embodiments, the present invention provides compound I-6:

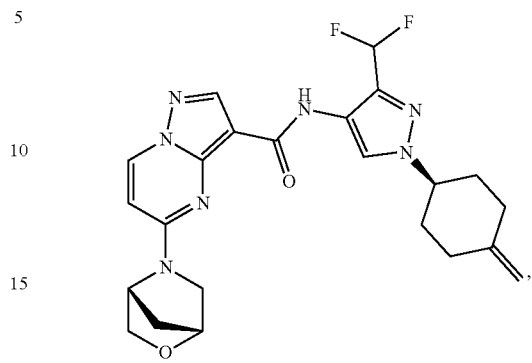

or a pharmaceutically acceptable salt thereof.

In some embodiments, the present invention provides compound I-8:

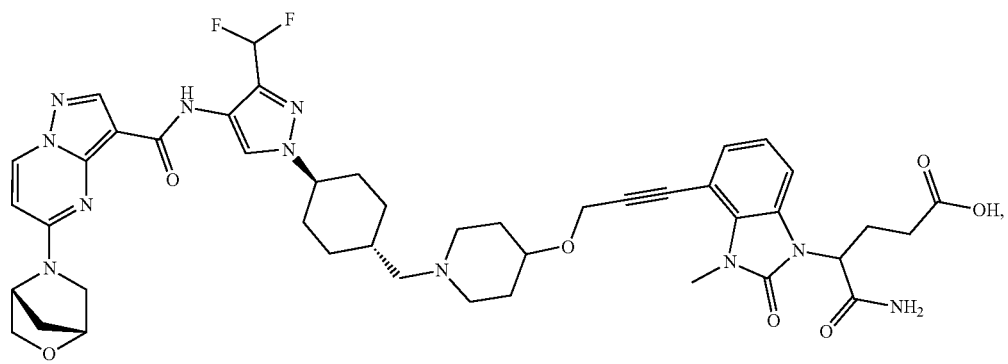 [SMILES: Cn1c(=O)n(C(CCC(=O)O)C(N)=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21]

or a pharmaceutically acceptable salt thereof.

In some embodiments, the present invention provides compound I-9:

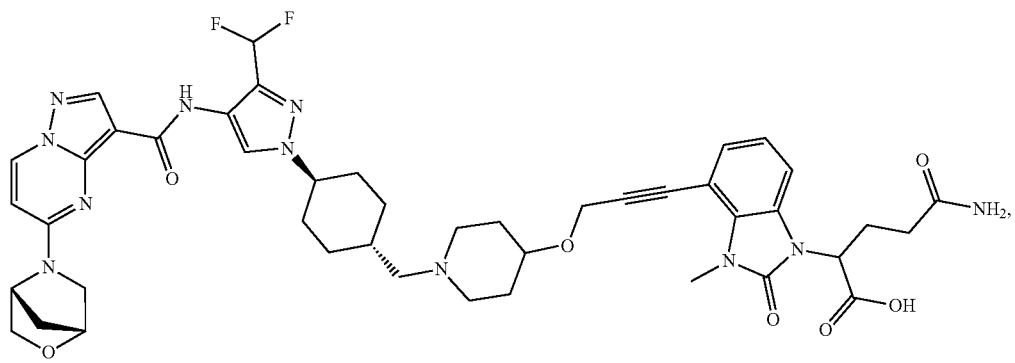 [SMILES: Cn1c(=O)n(C(CCC(N)=O)C(=O)O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21]
or a pharmaceutically acceptable salt thereof.
4. Description of Exemplary Compositions
In another aspect, the present invention provides a composition comprising compound I-1:
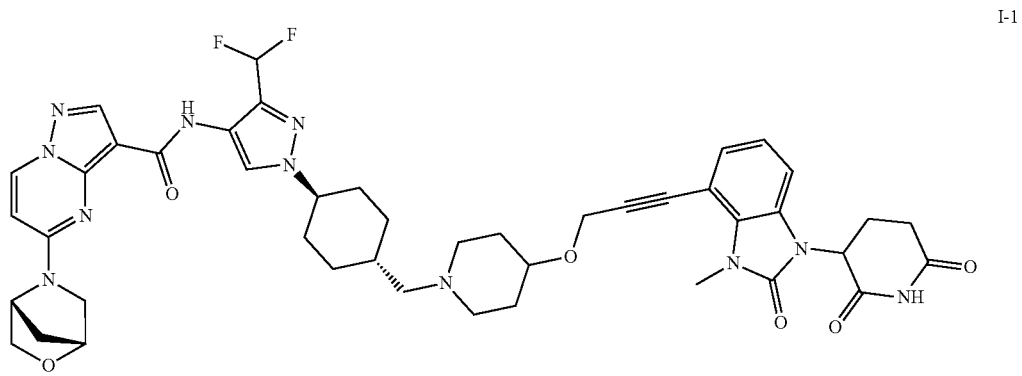 [SMILES: Cn1c(=O)n(C2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21]
I-1
or a pharmaceutically acceptable salt thereof, and one or more impurity compounds selected from the group consisting of:
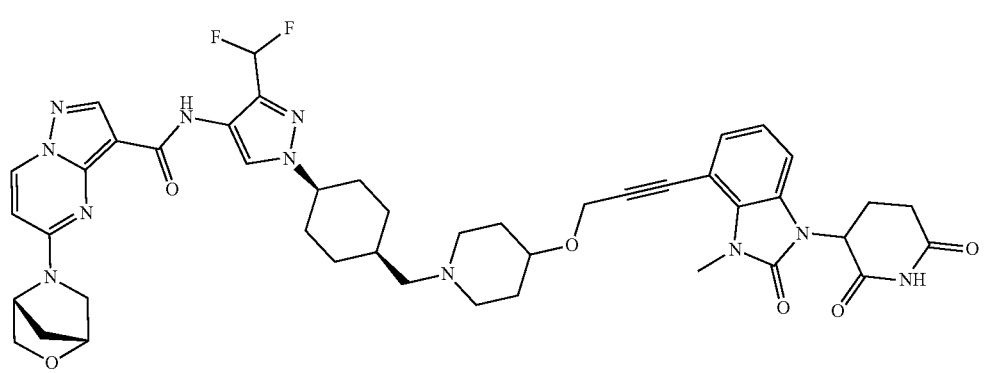
I-2

-continued
I-3
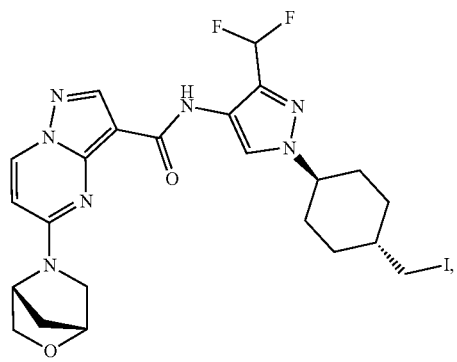
I-4
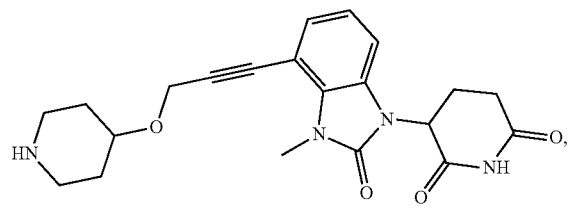
I-5
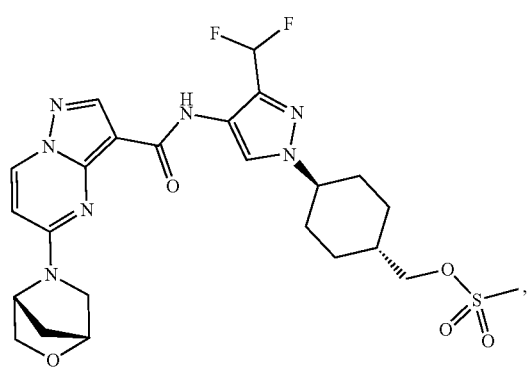
I-6
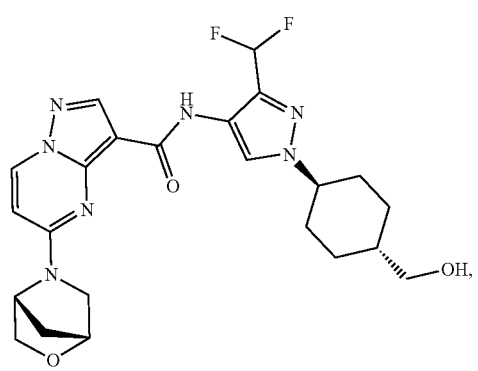
I-7
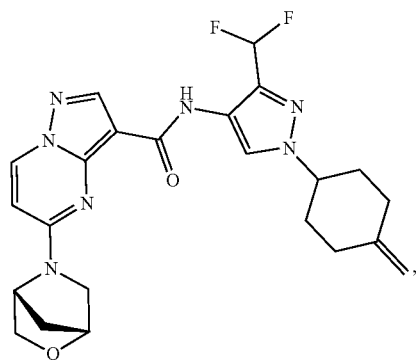
I-8
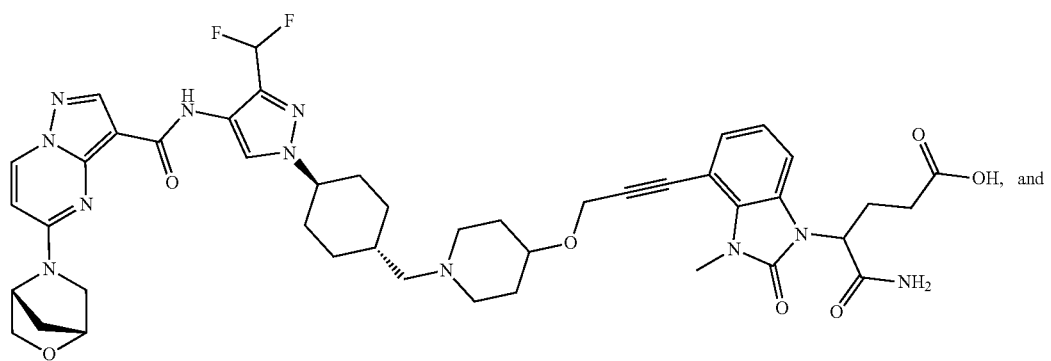

I-9

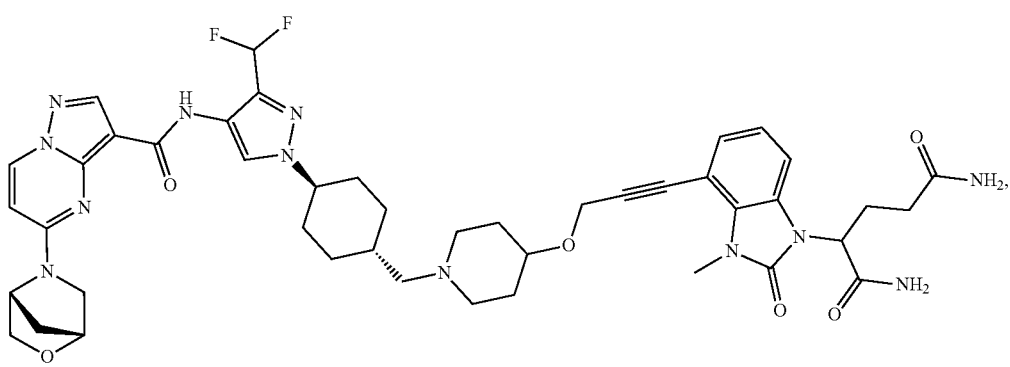

or a pharmaceutically acceptable salt thereof.

In some embodiments, the composition comprises compound I-1, or a pharmaceutically acceptable salt thereof, and one impurity compound selected from the group consisting of I-2, I-3, I-4, I-5, I-6, I-7, I-8, and I-9, or a pharmaceutically acceptable salt thereof.

In some embodiments, the composition comprises compound I-1, or a pharmaceutically acceptable salt thereof, and two impurity compounds selected from the group consisting of I-2, I-3, I-4, I 5, I-6, I-7, I-8, and I-9, or a pharmaceutically acceptable salt thereof.

In some embodiments, the composition comprises compound I-1, or a pharmaceutically acceptable salt thereof, and three impurity compounds selected from the group consisting of I-2, I-3, I-4, I-5, I-6, I-7, I-8, and I-9, or a pharmaceutically acceptable salt thereof.

In some embodiments, the composition comprises compound I-1, or a pharmaceutically acceptable salt thereof, and four impurity compounds selected from the group consisting of I-2, I-3,1-4, I-5, I-6, I-7, I-8, and I-9, or a pharmaceutically acceptable salt thereof.

In some embodiments, the composition comprises compound I-1, or a pharmaceutically acceptable salt thereof, and five impurity compounds selected from the group consisting of I-2, I-3, I-4, I 5, I-6, I-7, I-8, and I-9, or a pharmaceutically acceptable salt thereof.

In some embodiments, the composition comprises compound I-1, or a pharmaceutically acceptable salt thereof, and six impurity compounds selected from the group consisting of I-2, I-3, I-4, I 5, I-6, I-7, I-8, and I-9, or a pharmaceutically acceptable salt thereof.

In some embodiments, the composition comprises compound I-1, or a pharmaceutically acceptable salt thereof, and seven impurity compounds selected from the group consisting of I-2, I-3, I-4, I-5, I-6, I-7, I-8, and I-9, or a pharmaceutically acceptable salt thereof.

In some embodiments, the composition comprises compound I-1, or a pharmaceutically acceptable salt thereof, and each of impurity compounds I-2, I-3, I-4, I-5, I-6, I-7, I-8, and I-9, or a pharmaceutically acceptable salt thereof.

In some embodiments, the composition comprises compound I-1, or a pharmaceutically acceptable salt thereof, and one or more impurity compounds selected from the group consisting of I-2, I 3, I-4, I-5, and I-6, or a pharmaceutically acceptable salt thereof.

In some embodiments, the composition comprises compound I-1, or a pharmaceutically acceptable salt thereof, and one impurity compound selected from the group consisting of I-2, I-3, I-4, I-5, and I-6, or a pharmaceutically acceptable salt thereof.

In some embodiments, the composition comprises compound I-1, or a pharmaceutically acceptable salt thereof, and two impurity compounds selected from the group consisting of I-2, I-3, I-4, I 5, and I-6, or a pharmaceutically acceptable salt thereof.

In some embodiments, the composition comprises compound I-1, or a pharmaceutically acceptable salt thereof, and three impurity compounds selected from the group consisting of I-2, I-3, I-4, I-5, and I-6, or a pharmaceutically acceptable salt thereof.

In some embodiments, the composition comprises compound I-1, or a pharmaceutically acceptable salt thereof, and four impurity compounds selected from the group consisting of I-2, I-3, I-4, I-5, and I-6, or a pharmaceutically acceptable salt thereof.

In some embodiments, the composition comprises compound I-1, or a pharmaceutically acceptable salt thereof, and each of impurity compounds I-2, I-3, I-4, I-5, and I-6, or a pharmaceutically acceptable salt thereof.

In some embodiments, the composition comprises compound I-1, or a pharmaceutically acceptable salt thereof, and one or more impurity compounds selected from the group consisting of I-2, I 3, or I-5, or a pharmaceutically acceptable salt thereof.

In some embodiments, the composition comprises compound I-1, or a pharmaceutically acceptable salt thereof, and one impurity compound selected from the group consisting of I-2, I-3, or I-5, or a pharmaceutically acceptable salt thereof.

In some embodiments, the composition comprises compound I-1, or a pharmaceutically acceptable salt thereof, and two impurity compounds selected from the group consisting of I-2, I-3, or I-5, or a pharmaceutically acceptable salt thereof.

In some embodiments, the composition comprises compound I-1, or a pharmaceutically acceptable salt thereof, and each of impurity compounds I-2, I-3, or I-5, or a pharmaceutically acceptable salt thereof.

In some embodiments, the composition comprises compound I-1, or a pharmaceutically acceptable salt thereof, and impurity compound I-2, or a pharmaceutically acceptable salt thereof.

In some embodiments, the composition comprises compound I-1, or a pharmaceutically acceptable salt thereof, and impurity compound I-3, or a pharmaceutically acceptable salt thereof.

In some embodiments, the composition comprises compound I-1, or a pharmaceutically acceptable salt thereof, and impurity compound I-4, or a pharmaceutically acceptable salt thereof.

In some embodiments, the composition comprises compound I-1, or a pharmaceutically acceptable salt thereof, and impurity compound I-5, or a pharmaceutically acceptable salt thereof.

In some embodiments, the composition comprises compound I-1, or a pharmaceutically acceptable salt thereof, and impurity compound I-6, or a pharmaceutically acceptable salt thereof.

In some embodiments, the composition comprises compound I-1, or a pharmaceutically acceptable salt thereof, and impurity compound I-7, or a pharmaceutically acceptable salt thereof.

In some embodiments, the composition comprises compound I-1, or a pharmaceutically acceptable salt thereof, and impurity compound I-8, or a pharmaceutically acceptable salt thereof.

In some embodiments, the composition comprises compound I-1, or a pharmaceutically acceptable salt thereof, and impurity compound I-9, or a pharmaceutically acceptable salt thereof.

In some embodiments, a composition of the present invention comprises compound I-1, or a pharmaceutically acceptable salt thereof, in an amount of at least about 95, 95.5, 96, 96.5, 97, 97.5, 98, 98.5, 99.0, 99.5, 99.8, 99.9, 99.95, or 99.99 wt % of the total weight of the composition. In some embodiments, a composition comprises compound I-1, or a pharmaceutically acceptable salt thereof, in an amount of at least about 97 wt % of the total weight of the composition. In some embodiments, a composition comprises compound I-1, or a pharmaceutically acceptable salt thereof, in an amount of at least about 98 wt % of the total weight of the composition.

In some embodiments, a composition of the present invention comprises compound I-1 HCl, in an amount of at least about 95, 95.5, 96, 96.5, 97, 97.5, 98, 98.5, 99.0, 99.5, 99.8, 99.9, 99.95, or 99.99 wt % of the total weight of the composition. In some embodiments, a composition comprises compound I 1 HCl, in an amount of at least about 97 wt % of the total weight of the composition. In some embodiments, a composition comprises compound I-1 HCl, in an amount of at least about 98 wt % of the total weight of the composition.

In some embodiments, a composition of the present invention comprises compound I-1, or a pharmaceutically acceptable salt thereof, in an amount of at least about 95, 95.5, 96, 96.5, 97, 97.5, 98, 98.5, 99.0, 99.5, 99.8, 99.9, or 99.95 area percent HPLC. In some embodiments, a composition comprises compound I-1, or a pharmaceutically acceptable salt thereof, in an amount of at least about 97 area percent HPLC. In some embodiments, a composition comprises compound I-1, or a pharmaceutically acceptable salt thereof, in an amount of at least about 98 area percent HPLC. In some embodiments, a HPLC method is as described in the examples.

In some embodiments, a composition of the present invention comprises compound I-1 HCl, in an amount of at least about 95, 95.5, 96, 96.5, 97, 97.5, 98, 98.5, 99.0, 99.5, 99.8, 99.9, or 99.95 area percent HPLC. In some embodiments, a composition comprises compound I-1 HCl, in an amount of at least about 97 area percent HPLC. In some embodiments, a composition comprises compound I-1 HCl, in an amount of at least about 98 area percent HPLC. In some embodiments, a HPLC method is as described in the examples.

In some embodiments, a composition comprising compound I-1, or a pharmaceutically acceptable salt thereof, contains an amount of impurities no more than about 5.0, 4.0, 3.0, 2.0, 1.9, 1.8, 1.7, 1.6, 1.5, 1.25, 1, 0.75, 0.5, 0.25, 0.2, 0.1, 0.01, 0.005, or 0.001 wt % of the total weight of the composition. In some embodiments, the amount of total organic impurities is no more than about 3.0 wt % of the total weight of the composition. In some embodiments, the amount of total organic impurities is about 0.05-3.0, 0.05-2.9, 0.05-2.8, 0.05-2.7, 0.05-2.6, 0.05-2.5, 0.05-2.4, 0.05-2.3, 0.05-2.2, 0.05-2.1, 0.05-2.0, 0.1-3.0, 0.15-3.0, 0.2-3.0, 0.25-3.0, 0.3-3.0, 0.4-3.0, 0.5-3.0, 0.6-3.0, 0.7-3.0, 0.8-3.0, 0.9-3.0, or 1.0-3.0 wt % of the total weight of the composition. In some embodiments, the amount of total organic impurities is no more than about 2.0 wt % of the total weight of the composition. In some embodiments, the amount of total organic impurities is no more than about 1.0 wt % of the total weight of the composition.

In some embodiments, a composition comprising compound I-1, or a pharmaceutically acceptable salt thereof, the amount of total organic impurities is no more than about 5.0, 4.0, 3.0, 2.0, 1.9, 1.8, 1.7, 1.6, 1.5, 1.25, 1, 0.75, 0.5, 0.25, 0.2, 0.15, 0.1, or 0.05 area percent HPLC. In some embodiments, the amount of total organic impurities is no more than about 5.0 area percent HPLC. In some embodiments, the amount of total organic impurities is about 2.0-5.0, 2.0-4.5, 2.0-4.0, 2.0-3.8, 2.0-3.6, 2.0-3.5, 2.0-3.2, 2.0-3.0, 2.0-2.9, 2.0-2.8, 2.0-2.7, 2.0-2.6, 2.0-2.5, 2.0-2.4, 2.0-2.3, 2.0-2.2, or 2.0-2.1 area percent HPLC. In some embodiments, the amount of total organic impurities is no more than about 3.0 area percent HPLC. In some embodiments, the amount of total organic impurities is about 0.05-3.0, 0.05-2.9, 0.05-2.8, 0.05-2.7, 0.05-2.6, 0.05-2.5, 0.05-2.4, 0.05-2.3, 0.05-2.2, 0.05-2.1, 0.05-2.0, 0.1-3.0, 0.15-3.0, 0.2-3.0, 0.25-3.0, 0.3-3.0, 0.4-3.0, 0.5-3.0, 0.6-3.0, 0.7-3.0, 0.8-3.0, 0.9-3.0, or 1.0-3.0 area percent HPLC. In some embodiments, a HPLC method is as described in the examples.

In some embodiments, total organic impurities comprise one or more compounds selected from I-2, I-3, I-4, I-5, I-6, I-7, I-8, and I-9. In some embodiments, total organic impurities comprise one or more compounds selected from I-2, I-3, I-4, I-5, and I-6. In some embodiments, total organic impurities comprise one or more compounds selected from I-2, I-3, and I-5.

In some embodiments, each organic impurity is, independently, no more than about 1.0, 0.9, 0.8, 0.7, 0.6, 0.5, 0.4, 0.3, 0.2, 0.15, 0.1, or 0.05 wt % of the total weight of the composition. In some embodiments, each of organic impurities I-2, I-3, I-4, I-5, I-6, I-7, I-8, and I-9 is, independently, no more than about 0.7 wt % of the total weight of the composition. In some embodiments, each of organic impurities I-2, I-3, I-4, I-5, I-6, I-7, I-8, and I-9 is, independently, no more than about 0.5 wt % of the total weight of the composition. In some embodiments, an organic impurity selected from I-2, I-4, I-6, I-7, I-8, and I-9 is, independently, absent or about 0.2-0.7, 0.25-0.7, 0.3-0.7, 0.35-0.7, 0.4-0.7, 0.2-0.65, 0.2-0.6, 0.2-0.55, 0.2-0.5, 0.05-0.5, 0.1-0.5, 0.15-0.5, 0.2-0.5, or 0.25-0.5 wt % of the total weight of the composition.

In some embodiments, each organic impurity is, independently, no more than about 1.0, 0.9, 0.8, 0.7, 0.6, 0.5, 0.4, 0.3, 0.2, 0.15, 0.1, or 0.05 area percent HPLC. In some embodiments, each of organic impurities I-2, I-3, I-4, I-5, I-6, I-7, I-8, and I-9 is, independently, no more than about 0.7 area percent HPLC. In some embodiments, each of organic impurities I-2, I-3, I-4, I-5, I-6, I-7, I-8, and I-9 is, independently, no more than about 0.5 area percent HPLC. In some embodiments, an organic impurity selected from I-2, I-4, I-6, I-7, I-8, and I-9 is, independently, absent or about 0.2-0.7, 0.25-0.7, 0.3-0.7, 0.35-0.7, 0.4-0.7, 0.2-0.65, 0.2-0.6, 0.2-0.55, 0.2-0.5, 0.05-0.5, 0.1-0.5, 0.15-0.5, 0.2-0.5, or 0.25-0.5 area percent HPLC. In some embodiments, a HPLC method is as described in the examples.

In some embodiments, the amount of compound I-2, or a pharmaceutically acceptable salt thereof, is about 0.05-2.0, 0.1-2.0, or 0.5-2.0 wt % of the total weight of the composition. In some embodiments, the amount of compound I-2, or a pharmaceutically acceptable salt thereof, is about 0.1, 0.5, 1.0, or 1.5 wt % of the total weight of the composition. In some embodiments, the amount of compound I 2, or a pharmaceutically acceptable salt thereof, is no more than about 2.0 wt % of the total weight of the composition. In some embodiments, the amount of compound I-2, or a pharmaceutically acceptable salt thereof, is about 0.5-1.0 or 1.0-1.5 wt % of the total weight of the composition. In some embodiments, the amount of compound I-2, or a pharmaceutically acceptable salt thereof, is no more than about 0.5 wt % of the total weight of the composition. In some embodiments, the amount of compound I-2, or a pharmaceutically acceptable salt thereof, is about 0.05-2.0, 0.1-2.0, or 0.5-2.0 area percent HPLC. In some embodiments, the amount of compound I-2, or a pharmaceutically acceptable salt thereof, is about 0.1, 0.5, 1.0, or 1.5 area percent HPLC. In some embodiments, the amount of compound I-2, or a pharmaceutically acceptable salt thereof, is no more than about 2.0 area percent HPLC. In some embodiments, the amount of compound I-2, or a pharmaceutically acceptable salt thereof, is about 0.5-1.0 or 1.0-1.5 area percent HPLC. In some embodiments, the amount of compound I-2, or a pharmaceutically acceptable salt thereof, is no more than about 0.5 area percent HPLC. In some embodiments, compound I-2 is absent (as determined by HPLC) from the composition. In some embodiments, a HPLC method is as described in the examples.

In some embodiments, the amount of compound I-4, or a pharmaceutically acceptable salt thereof, is about 0.05-0.7, 0.1-0.7, or 0.2-0.7 wt % of the total weight of the composition. In some embodiments, the amount of compound I-4, or a pharmaceutically acceptable salt thereof, is about 0.01, 0.05, 0.1, or 0.5 wt % of the total weight of the composition. In some embodiments, the amount of compound I-4, or a pharmaceutically acceptable salt thereof, is no more than about 0.7 wt % of the total weight of the composition. In some embodiments, the amount of compound I-4, or a pharmaceutically acceptable salt thereof, is about 0.01-0.1 or 0.05-0.5 wt % of the total weight of the composition. In some embodiments, the amount of compound I-4, or a pharmaceutically acceptable salt thereof, is no more than about 0.5 wt % of the total weight of the composition. In some embodiments, the amount of compound I 4, or a pharmaceutically acceptable salt thereof, is about 0.05-0.7, 0.1-0.7, or 0.2-0.7 area percent HPLC. In some embodiments, the amount of compound I-4, or a pharmaceutically acceptable salt thereof, is 0.01, 0.05, 0.1, or 0.5 area percent HPLC. In some embodiments, the amount of compound I-4, or a pharmaceutically acceptable salt thereof, is no more than about 0.7 area percent HPLC. In some embodiments, the amount of compound I-4, or a pharmaceutically acceptable salt thereof, is about 0.01-0.1 or 0.05-0.5 area percent HPLC. In some embodiments, the amount of compound I-4, or a pharmaceutically acceptable salt thereof, is no more than about 0.5 area percent HPLC. In some embodiments, compound I 4 is absent (as determined by HPLC) from the composition. In some embodiments, a HPLC method is as described in the examples.

In some embodiments, the amount of compound I-6, or a pharmaceutically acceptable salt thereof, is about 0.05-0.7, 0.1-0.7, or 0.2-0.7 wt % of the total weight of the composition. In some embodiments, the amount of compound I-6, or a pharmaceutically acceptable salt thereof, is about 0.01, 0.05, 0.1, or 0.5 wt % of the total weight of the composition. In some embodiments, the amount of compound I-6, or a pharmaceutically acceptable salt thereof, is no more than about 0.7 wt % of the total weight of the composition. In some embodiments, the amount of compound I-6, or a pharmaceutically acceptable salt thereof, is about 0.01-0.1 or 0.05-0.5 wt % of the total weight of the composition. In some embodiments, the amount of compound I-6, or a pharmaceutically acceptable salt thereof, is no more than about 0.5 wt % of the total weight of the composition. In some embodiments, the amount of compound I 6, or a pharmaceutically acceptable salt thereof, is about 0.05-0.7, 0.1-0.7, or 0.2-0.7 area percent HPLC. In some embodiments, the amount of compound I-6, or a pharmaceutically acceptable salt thereof, is 0.01, 0.05, 0.1, or 0.5 area percent HPLC. In some embodiments, the amount of compound I-6, or a pharmaceutically acceptable salt thereof, is no more than about 0.7 area percent HPLC. In some embodiments, the amount of compound I-6, or a pharmaceutically acceptable salt thereof, is about 0.01-0.1 or 0.05-0.5 area percent HPLC. In some embodiments, the amount of compound I-6, or a pharmaceutically acceptable salt thereof, is no more than about 0.5 area percent HPLC. In some embodiments, compound I 6 is absent (as determined by HPLC) from the composition. In some embodiments, a HPLC method is as described in the examples.

In some embodiments, the amount of compound I-7, or a pharmaceutically acceptable salt thereof, is about 0.05-0.7, 0.1-0.7, or 0.2-0.7 wt % of the total weight of the composition. In some embodiments, the amount of compound I-7, or a pharmaceutically acceptable salt thereof, is about 0.01, 0.05, 0.1, or 0.5 wt % of the total weight of the composition. In some embodiments, the amount of compound I-7, or a pharmaceutically acceptable salt thereof, is no more than about 0.7 wt % of the total weight of the composition. In some embodiments, the amount of compound I-7, or a pharmaceutically acceptable salt thereof, is about 0.01-0.1 or 0.05-0.5 wt % of the total weight of the composition. In some embodiments, the amount of compound I-7, or a pharmaceutically acceptable salt thereof, is no more than about 0.5 wt % of the total weight of the composition. In some embodiments, the amount of compound I-7, or a pharmaceutically acceptable salt thereof, is about 0.05-0.7, 0.1-0.7, or 0.2-0.7 area percent HPLC. In some embodiments, the amount of compound I-7, or a pharmaceutically acceptable salt thereof, is 0.01, 0.05, 0.1, or 0.5 area percent HPLC. In some embodiments, the amount of compound I-7, or a pharmaceutically acceptable salt thereof, is no more than about 0.7 area percent HPLC. In some embodiments, the amount of compound I-7, or a pharmaceutically acceptable salt thereof, is about 0.01-0.1 or 0.05-0.5 area percent HPLC. In some embodiments, the amount of compound I-7, or a pharmaceutically acceptable salt thereof, is no more than about 0.5 area percent HPLC. In some embodiments, compound I-7 is absent (as determined by HPLC) from the composition. In some embodiments, a HPLC method is as described in the examples.

In some embodiments, the amount of compound I-8, or a pharmaceutically acceptable salt thereof, is about 0.05-0.7, 0.1-0.7, or 0.2-0.7 wt % of the total weight of the composition. In some embodiments, the amount of compound I-8, or a pharmaceutically acceptable salt thereof, is about 0.01, 0.05, 0.1, or 0.5 wt % of the total weight of the composition. In some embodiments, the amount of compound I-8, or a pharmaceutically acceptable salt thereof, is no more than about 0.7 wt % of the total weight of the composition. In some embodiments, the amount of compound I-8, or a pharmaceutically acceptable salt thereof, is about 0.01-0.1 or 0.05-0.5 wt % of the total weight of the composition. In some embodiments, the amount of compound I-8, or a pharmaceutically acceptable salt thereof, is no more than about 0.5 wt % of the total weight of the composition. In some embodiments, the amount of compound I-8, or a pharmaceutically acceptable salt thereof, is about 0.05-0.7, 0.1-0.7, or 0.2-0.7 area percent HPLC. In some embodiments, the amount of compound I-8, or a pharmaceutically acceptable salt thereof, is 0.01, 0.05, 0.1, or 0.5 area percent HPLC. In some embodiments, the amount of compound I-8, or a pharmaceutically acceptable salt thereof, is no more than about 0.7 area percent HPLC. In some embodiments, the amount of compound I-8, or a pharmaceutically acceptable salt thereof, is about 0.01-0.1 or 0.05-0.5 area percent HPLC. In some embodiments, the amount of compound I-8, or a pharmaceutically acceptable salt thereof, is no more than about 0.5 area percent HPLC. In some embodiments, compound I-8 is absent (as determined by HPLC) from the composition. In some embodiments, a HPLC method is as described in the examples.

In some embodiments, the amount of compound I-9, or a pharmaceutically acceptable salt thereof, is about 0.05-0.7, 0.1-0.7, or 0.2-0.7 wt % of the total weight of the composition. In some embodiments, the amount of compound I-9, or a pharmaceutically acceptable salt thereof, is about 0.01, 0.05, 0.1, or 0.5 wt % of the total weight of the composition. In some embodiments, the amount of compound I-9, or a pharmaceutically acceptable salt thereof, is no more than about 0.7 wt % of the total weight of the composition. In some embodiments, the amount of compound I-9, or a pharmaceutically acceptable salt thereof, is about 0.01-0.1 or 0.05-0.5 wt % of the total weight of the composition. In some embodiments, the amount of compound I-9, or a pharmaceutically acceptable salt thereof, is no more than about 0.5 wt % of the total weight of the composition. In some embodiments, the amount of compound I 9, or a pharmaceutically acceptable salt thereof, is about 0.05-0.7, 0.1-0.7, or 0.2-0.7 area percent HPLC. In some embodiments, the amount of compound I-9, or a pharmaceutically acceptable salt thereof, is 0.01, 0.05, 0.1, or 0.5 area percent HPLC. In some embodiments, the amount of compound I-9, or a pharmaceutically acceptable salt thereof, is no more than about 0.7 area percent HPLC. In some embodiments, the amount of compound I-9, or a pharmaceutically acceptable salt thereof, is about 0.01-0.1 or 0.05-0.5 area percent HPLC. In some embodiments, the amount of compound I-9, or a pharmaceutically acceptable salt thereof, is no more than about 0.5 area percent HPLC. In some embodiments, compound I 9 is absent (as determined by HPLC) from the composition. In some embodiments, a HPLC method is as described in the examples.

In some embodiments, a composition comprising compound I-1, or a pharmaceutically acceptable salt thereof, contains one or more genotoxic impurity. In some embodiments, the potential genotoxicity of selected impurities are evaluated in silico by means of DEREK 6.0.0 *Nexus* 2.2.0 (mutagenicity only) and LSMA Version 2.4.5-7 (mutagenicity suite), e.g., as shown in the Examples section below. In some embodiments, each of the genotoxic impurities in a composition is, independently, no more than about 30 ppm. In some embodiments, each of genotoxic impurities in a composition is, independently, no more than about 20 ppm. In some embodiments, each of genotoxic impurities in a composition is, independently, about 29, 28, 27, 26, 25, 24, 23, 22, 21, 20, 19, 18, 17, 16, 15, 14, 13, 12, 11, 10, 9, 8, 7, 6, 5, 4, 3, 2, or 1 ppm, or less than 1 ppm. In some embodiments, a composition comprises no more than about 15 ppm total genotoxic impurities. In some embodiments, a composition comprises no more than about 10 ppm total genotoxic impurities. In some embodiments, a composition comprises about 15, 14, 13, 12, 11, 10, 9, 8, 7, 6, 5, 4, 3, 2, or 1 ppm, or less than about 1 ppm, total genotoxic impurities. In some embodiments, a genotoxic impurity is compound I-3 and compound I-5. In some embodiments, a genotoxic impurity is compound I-3. In some embodiments, a genotoxic impurity is compound I-5.

In some embodiments, the composition comprises compound I-1 HCl and impurity compound I-2, wherein compound I-1 HCl is at an amount of at least about 97 area percent HPLC, and impurity compound I-2 is at an amount of no more than about 2 area percent HPLC. In some embodiments, the composition comprises compound I-1 HCl, impurity compound I-2, and impurity compound I-3 or I-5, wherein compound I-1 HCl is at an amount of at least about 97 area percent HPLC, impurity compound I 2 is at an amount of no more than about 2 area percent HPLC, and impurity compound I-3 or I-5 is at an amount of no more than about 30 ppm. In some embodiments, the composition comprises compound I-1 HCl, impurity compounds I-2, I-3, and I-5, wherein compound I-1 HCl is at an amount of at least about 97 area percent HPLC, impurity compound I-2 is at an amount of no more than about 2 area percent HPLC, and each of impurity compounds I-3 and I-5 is at an amount of no more than about 30 ppm. In some embodiments, the HPLC method is as described in the example.

In some embodiments, a composition comprises a residual solvent in an amount of no more than about 9000, 8000, 7000, 6000, 5000, 4000, 3000, 2000, 1000, or 500 ppm. In some embodiments, a residual solvent is about 100, 200, 300, 400, 500, 600, 700, 800, 900, or 1000 ppm. In some embodiments, a residual solvent is no more than about 500 ppm. In some embodiments, residual solvent content is measured by capillary GC.

In some embodiments, a composition comprises residual solvent dichloromethane in an amount of no more than about 600 ppm. In some embodiments, residual solvent dichloromethane is no more than about 600, 500, 400, 300, or 200 ppm. In some embodiments, residual solvent dichloromethane is no more than about 100 ppm. In some embodiments, residual solvent dichloromethane is about 10-100, 50-200, 100-300, 150-400, 200-500, 250-600, or 300-700 ppm. In some embodiments, residual solvent dichloromethane is absent (as determined by GC) from the composition.

In some embodiments, a composition comprises residual solvent N,N-dimethylacetamide in an amount of no more than about 1090 ppm. In some embodiments, residual solvent N,N-dimethylacetamide is no more than about 1000, 900, 800, 700, 600, 500, 400, 300, or 200 ppm. In some embodiments, residual solvent N,N-dimethylacetamide is no more than about 100 ppm. In some embodiments, residual solvent N,N-dimethylacetamide is about 10-100, 50-200, 100-300, 150-400, 200-500, 250-600, 300-700, 400-800, 500-900, or 600-1000 ppm. In some embodiments, residual solvent N,N-dimethylacetamide is absent (as determined by GC) from the composition.

In some embodiments, a composition comprises residual solvent tetrahydrofuran in an amount of no more than about 720 ppm. In some embodiments, residual solvent tetrahydrofuran is no more than about 700, 600, 500, 400, 300, or 200 ppm. In some embodiments, residual solvent tetrahydrofuran is no more than about 100 ppm. In some embodiments, residual solvent tetrahydrofuran is about 10-100, 50-200, 100-300, 150-400, 200-500, 250-600, or 300-700 ppm. In some embodiments, residual solvent tetrahydrofuran is absent (as determined by GC) from the composition.

In some embodiments, a composition comprises residual solvent 2-propanol in an amount of no more than about 5000 ppm. In some embodiments, residual solvent 2-propanol is no more than about 4000, 3000, 2000, 1000, or 500 ppm. In some embodiments, residual solvent 2-propanol is no more than about 100 ppm. In some embodiments, residual solvent 2-propanol is about 100-1000, 500-2000, 1000-3000, 1500-4000, or 2000-5000 ppm. In some embodiments, residual solvent 2-propanol is absent (as determined by GC) from the composition.

In some embodiments, a composition comprises residual solvent 2-methyltetrahydrofivan in an amount of no more than about 5000 ppm. In some embodiments, residual solvent 2-methyltetrahydrofuran is no more than about 4000, 3000, 2000, 1000, or 500 ppm. In some embodiments, residual solvent 2-methyltetrahydrofuran is no more than about 100 ppm. In some embodiments, residual solvent 2-methyltetrahydrofuran is about 100-1000, 500-2000, 1000-3000, 1500-4000, or 2000-5000 ppm.

In some embodiments, residual solvent 2-methyltetrahydrofuran is absent (as determined by GC) from the composition.

In some embodiments, the present invention provides a composition comprising I-1 HCl, and one or more additional component of the acceptance criteria as described in Table 2 in Example 2. In some embodiments, the present invention provides a composition comprising I-1 HCl, and all components of the acceptance criteria as described in Table 2 in Example 2.

In some embodiments, the present invention provides any compound described above and disclosed herein in isolated form. As used herein, the term "isolated" means that a compound is provided in a form that is separated from other components that might be present in that compound's usual environment. In certain embodiments, an isolated compound is in solid form. In some embodiments, an isolated compound is at least about 50% pure as determined by a suitable HPLC method. In certain embodiments, an isolated compound is at least about 60%, 70%, 80%, 90%, 95%, 98%, 99%, 99.5%, 99.6%, 99.7%, 99.8%, 99.9%, 99.95%, 99.99%, or 99.999% pure as determined by a suitable HPLC method. Percent purity may be measured by weight percent of the desired compound (% w/w), by area % relative to the total area of the HPLC chromatogram, or by other methods known in the art.

In some embodiments, a composition is a tablet. In some embodiments, compound I-1, or a pharmaceutically acceptable salt thereof, in a tablet is in an amount of at least about 97 area percent of the HPLC relative to the total area of the compound I-1 and impurity compounds peaks in the HPLC chromatogram. In some embodiments, the amount of an organic impurity, as described above, in a tablet is no more than about 0.7% area percent of the HPLC relative to the total area of the compound I-1 and impurity compounds peaks in the HPLC chromatogram. In some embodiments, a HPLC method is as described in the examples.

Disclosed compounds may be purified by any means known in the art. Such means include, e.g. silica gel column chromatography; medium pressure liquid chromatography (MPLC); high pressure liquid chromatography (HPLC); preparative HPLC (prep-HPLC); flash chromatography (FC); liquid chromatography (LC); supercritical fluid chromatography (SFC); thin layer chromatography (TLC); preparative TLC (prep-TLC); liquid chromatography-mass spectrometry (LC-MS, LCMS or LC/MS); recrystallization; precipitation; trituration; distillation; derivatization; acid-base extraction; and the like.

The term "purified", "in purified form" or "in isolated and purified form" for a compound refers to the physical state of said compound after being isolated from a synthetic process (e.g., from a reaction mixture), or natural source or combination thereof. Thus, the term "purified", "in purified form" or "in isolated and purified form" for a compound refers to the physical state of said compound (or a tautomer or stereoisomer thereof, or pharmaceutically acceptable salt or solvate of said compound, said stereoisomer, or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

5. Description of Synthesis of Compound Formula I and Relevant Intermediates

In some embodiments, compound of formula I, or a pharmaceutically acceptable salt thereof, is synthesized according to Scheme 1:

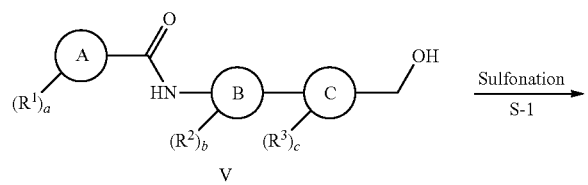

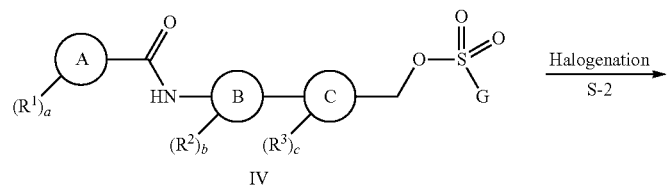

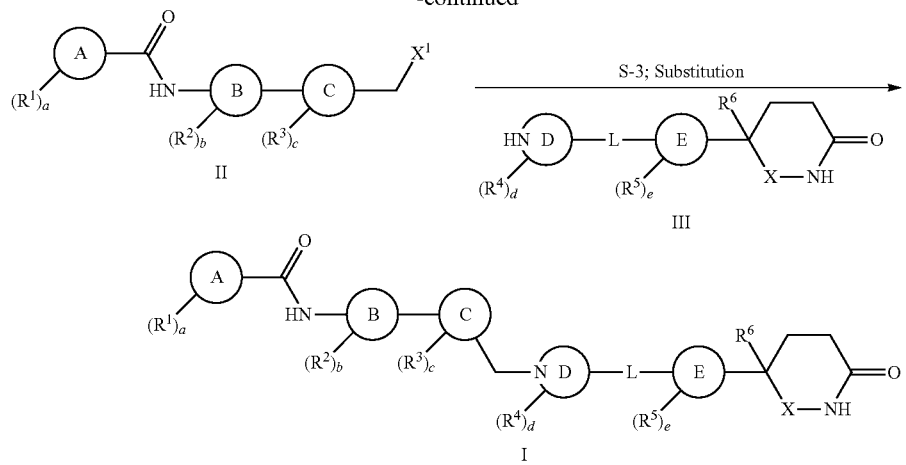

At step S-1, the primary hydroxyl of compound of formula V, or a salt thereof, is sulfonated using an appropriate sulfonation reagent to provide a sulfonate ester compound of formula IV. Suitable sulfonation reagents and reaction conditions are well known to one of ordinary skill in the art, see for example, Greene's Protective Groups in Organic Synthesis, P. G. M. Wuts and T. W. Greene, 4$^{th}$ Edition, John Wiley & Sons, 2007. In some embodiments, step S-1 comprises a reaction between compound of formula V and methanesulfonyl chloride (MsCl) or methanesulfonic anhydride (Ms$_2$O). In some embodiments, step S-1 comprises a solvent tetrahydrofuran (THF). In some embodiments, step S-1 comprises a tertiary base (e.g., triethylamine, diisopropylethylamine, etc.).

At step S-2, the sulfonate ester of the compound of formula IV, or a salt thereof, is halogenated using an appropriate halogenation reagent to provide a primary halogen compound of formula II. Suitable halogenation reagents and reaction conditions are well known to one of ordinary skill in the art, see for example, Greene's Protective Groups in Organic Synthesis, P. G. M. Wuts and T. W. Greene, 4$^{th}$ Edition, John Wiley & Sons, 2007. In some embodiments, step S-2 comprises a reaction between compound of formula IV and lithium iodide. In some embodiments, step S-2 comprises a solvent 2-methyltetrahydrofuran (2-MeTHF).

At step S-3, the primary halogen of the compound of formula II, or a salt thereof, is reacted with a compound of formula III under appropriate substitution conditions to provide the compound of formula I. Suitable reaction conditions for substitution reactions are well known to one of ordinary skill in the art, see for example, Greene's Protective Groups in Organic Synthesis, P. G. M. Wuts and T. W. Greene, 4$^{th}$ Edition, John Wiley & Sons, 2007. In some embodiments, step S-3 comprises a solvent N—N-dimetylacetamide (DMAc). In some embodiments, step S-3 comprises a tertiary base (e.g., triethylamine, diisopropylethylamine, etc.).

One of ordinary skill in the art will appreciate that compound formula I, or a salt thereof, may be prepared in a crystal polymorph form through one or more acidifying, basifying, slurrying, warming, cooling, filtering, precipitating, and seeding steps.

In some embodiment, the present invention provides a process for preparing a compound of formula I:

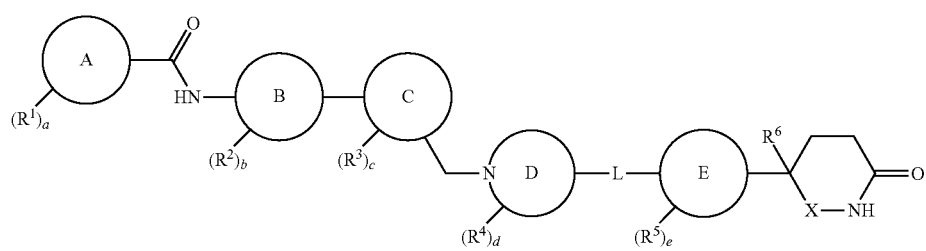

I or a pharmaceutically acceptable salt thereof, wherein:

X is a bivalent moiety selected from a covalent bond, —CH$_2$—, —C(O)—, —C(S)—, or

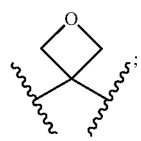 [SMILES: *C1(*)COC1]

R$^1$, R$^2$, R$^3$, R$^4$, and R$^5$, independently, are selected from hydrogen, deuterium, RA, halogen, —CN, —NO$_2$, —OR, —SR, —NR$_2$, —SO$_2$R, —SO$_2$NR$_2$, —S(O)R, —CFR$_2$, —CF$_2$R, —CF$_3$, —CR$_2$OR, —CR$_2$(NR$_2$), —C(O)R, —C(O)OR, —C(O)NR$_2$, —C(S)NR$_2$, —C(O)NROR, —OC(O)R, —OC(O)NR$_2$, —NRC(O)

OR, —NRC(O)R, —NRC(O)NR$_2$, —NRSO$_2$R, —N$^-$(O$^-$)R$_2$, —OP(O)R$_2$, —OP(OXOR)$_2$, —OP(OXOR)NR$_2$, —OP(O)(NR$_2$)$_2$, —P(O)R$_2$, —SiR$_3$, —Si(OR)R$_2$, or

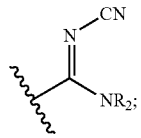

each R, independently, is hydrogen, or an optionally substituted group selected from C$_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
  two R groups on the same carbon or nitrogen are optionally taken together with their intervening atoms to form a 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur, or a 5-9 membered heteroaryl ring having 1-4 heteroatoms independently selected from nitrogen, oxygen, and sulfur;
each R$^A$, independently, is an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
a, b, c, d, and e, independently, are selected from 0, 1, 2, 3, or 4;
R$^6$ is hydrogen or C$_{1-4}$ aliphatic;
Ring A, Ring B, and Ring E, independently, are selected from phenyl, naphthyl, a 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur, or a 5-10 membered monocyclic or bicyclic heteroaryl ring having 1-4 heteroatoms independently selected from nitrogen, oxygen, and sulfur;
Ring C is a 4-6 membered saturated or partially unsaturated carbocyclic or heterocyclic ring having 1-2 heteroatoms selected from nitrogen, oxygen, and sulfur;
Ring D is a 4-6 membered saturated or partially unsaturated heterocyclic ring having, in addition to the nitrogen present, 0-2 heteroatoms selected from nitrogen, oxygen, and sulfur;
L is a covalent bond or a bivalent, saturated or unsaturated, straight or branched C$_{1-10}$ hydrocarbon chain, wherein 0-6 methylene units of L are independently replaced by —CDH—, —CD$_2$—, —CRF—, —CF$_2$—, —Cy-, —O—, —NR—, —SiR$_2$—, —Si(OH)R—, —Si(OH)$_2$—, —P(O)OR—, —P(O)R—, —P(O)NR$_2$—, —S—, —OC(O)—, —C(O)O—, —C(O)—, —S(O)—, —SO$_2$—, —NRSO$_2$—, —SO$_2$NR—, —NRC(O)—, —C(O)NR—, —OC(O)NR—, —NRC(O)O—,

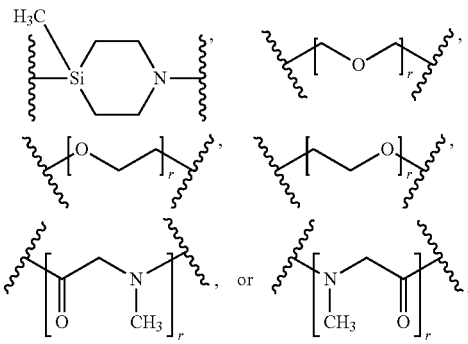

each -Cy-, independently, is an optionally substituted bivalent ring selected from phenylenyl, an 8-10 membered bicyclic arylenyl, a 4-7 membered saturated or partially unsaturated carbocyclylenyl, a 4-12 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-12 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur; and
r is 0, 1, 2, 3, 4, 5, 6, 7, 8, 9, or 10,
comprising treating a compound of formula II:

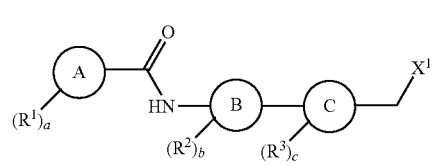

or pharmaceutically acceptable salt thereof, wherein:
X$^1$ is a suitable leaving group,
with a compound of formula III:

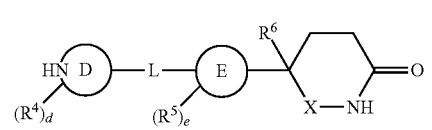

under suitable conditions to form the compound of formula I or a pharmaceutically acceptable salt thereof.
In some embodiments, a compound of formula I is compound I-1. In some embodiments, a compound of formula II is compound I-3. In some embodiments, a compound of formula III is compound I-4.

In some embodiments, the present invention provides a process for preparing a compound of formula II, wherein $X^1$ is a halogen, the process comprising halogenating a compound of formula IV:

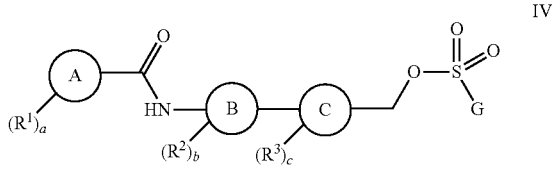

IV or a pharmaceutically acceptable salt thereof, wherein:
each of variables $R^1$, $R^2$, $R^3$, a, b, c, Ring A, Ring B, and Ring C is independently as defined and described in embodiments herein; and
G is an optionally substituted group selected from a $C_{1-6}$ aliphatic, phenyl, naphthyl, a 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur, or a 5-10 membered monocyclic or bicyclic heteroaryl ring having 1-4 heteroatoms independently selected from nitrogen, oxygen, and sulfur;
under suitable conditions to form the compound of formula II or a pharmaceutically acceptable salt thereof.

In some embodiments, the present invention provides a process to prepare a compound of formula I, the process comprising treating a compound of formula IV with a compound of formula III under suitable conditions to form the compound of formula I or a pharmaceutically acceptable salt thereof.

In some embodiments, a compound of formula IV is compound I-5.

In some embodiments, the present invention provides a process for preparing a compound of formula IV, the process comprising sulfonating a compound of formula V:

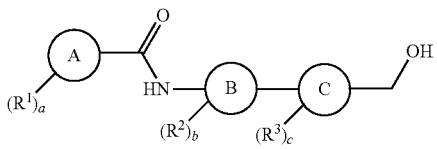

V or a pharmaceutically acceptable salt thereof, under suitable conditions to form the compound of formula IV or a pharmaceutically acceptable salt thereof, wherein each variable is independently as defined and described in embodiments herein.

In some embodiments, the present invention provides a process to prepare a compound of formula I, the process comprising treating a compound of formula V with a compound of formula III under suitable conditions to form the compound of formula I or a pharmaceutically acceptable salt thereof.

In some embodiments, a compound of formula V is compound I-6.

How about incorporate by reference the definitions of the variables of formula I, followed by the simplified version below?

As described above, X is a bivalent moiety selected from a covalent bond, —CH$_2$—, —C(O)—, —C(S)—, or

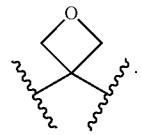 [SMILES: *C1(*)COC1]

In some embodiments, X is a covalent bond. In some embodiments, X is —CH$_2$—. In some embodiments, X is —C(O)—. In some embodiments, X is —C(S)—. In some embodiments, X is

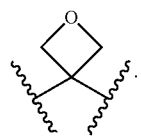 [SMILES: *C1(*)COC1]

As described above, $R^1$, $R^2$, $R^3$, $R^4$, and $R^5$, independently, are selected from hydrogen, deuterium, RA, halogen, —CN, —NO$_2$, —OR, —SR, —NR$_2$, —SO$_2$R, —SO$_2$NR$_2$, —S(O)R, —CFR$_2$, —CF$_2$R, —CF$_3$, —CR$_2$OR, —CR$_2$(NR$_2$), —C(O)R, —C(O)OR, —C(O)NR$_2$, —C(S)NR$_2$, —C(O)NROR, —OC(O)R, —OC(O)NR$_2$, —NRC(O)OR, —NRC(O)R, —NRC(O)NR$_2$, —NRSO$_2$R, —N$^+$(O$^-$)R$_2$, —OP(O)R$_2$, —OP(OXOR)$_2$, —OP(OXOR)NR$_2$, —OP(OXNR$_2$)$_2$, —P(O)R$_2$, —SiR$_3$, —Si(OR)R$_2$, or LLNR$_2$, or

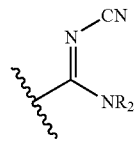

In some embodiments, one or more of $R^1$, $R^2$, $R^3$, $R^4$, and $R^5$, is hydrogen. In some embodiments, one or more of $R^1$, $R^2$, $R^3$, $R^4$, and $R^5$, is deuterium. In some embodiments, one or more of $R^1$, $R^2$, $R^3$, $R^4$, and $R^5$, is $R^A$. In some embodiments, one or more of $R^1$, $R^2$, $R^3$, $R^4$, and $R^5$, is halogen. In some embodiments, one or more of $R^1$, $R^2$, $R^3$, $R^4$, and $R^5$, is —CN. In some embodiments, one or more of $R^1$, $R^2$, $R^3$, $R^4$, and $R^5$, is —NO$_2$. In some embodiments, one or more of $R^1$, $R^2$, $R^3$, $R^4$, and $R^5$, is —OR. In some embodiments, one or more of $R^1$, $R^2$, $R^3$, $R^4$, and $R^5$, is —SR. In some embodiments, one or more of $R^1$, $R^2$, $R^3$, $R^4$, and $R^5$, is —NR$_2$. In some embodiments, one or more of $R^1$, $R^2$, $R^3$, $R^4$, and $R^5$, is —SO$_2$R. In some embodiments, one or more of $R^1$, $R^2$, $R^3$, $R^4$, and $R^5$, is —SO$_2$NR$_2$. In some embodiments, one or more of $R^1$, $R^2$, $R^3$, $R^4$, and $R^5$, is —S(O)R. In some embodiments, one or more of $R^1$, $R^2$, $R^3$, $R^4$, and $R^5$, is —CFR$_2$. In some embodiments, one or more of $R^1$, $R^2$, $R^3$, $R^4$, and $R^5$, is —CF$_2$R. In some embodiments, one or more of $R^1$, $R^2$, $R^3$, $R^4$, and $R^5$, is —CF$_3$. In some embodiments, one or more of $R^1$, $R^2$, $R^3$, $R^4$, and $R^5$, is —CR$_2$OR. In some embodiments, one or more of $R^1$, $R^2$, $R^3$, $R^4$, and $R^5$, is —CR$_2$(NR$_2$). In some embodiments, one or more of $R^1$, $R^2$, $R^3$, $R^4$, and $R^5$, is —C(O)R. In some embodiments, one or more of $R^1$, $R^2$, $R^3$, $R^4$, and $R^5$, is —C(O)OK In some embodiments, one or more of $R^1$, $R^2$, $R^3$, $R^4$, and $R^5$, is —C(O)NR$_2$. In some embodiments, one or more of $R^1$, $R^2$, $R^3$, $R^4$, and $R^5$, is —C(S)$NR_2$. In some embodiments, one or more of $R^1$, $R^2$, $R^3$, $R^4$, and $R^5$, is —C(O)NROR. In some embodiments, one or more of $R^1$, $R^2$, $R^3$, $R^4$, and $R^5$, is —OC(O)R. In some embodiments, one or more of $R^1$, $R^2$, $R^3$, $R^4$, and $R^5$, is —OC(O)$NR_2$. In some embodiments, one or more of $R^1$, $R^2$, $R^3$, $R^4$, and $R^5$, is —NRC(O)OR. In some embodiments, one or more of $R^1$, $R^2$, $R^3$, $R^4$, and $R^5$, is —NRC(O)R In some embodiments, one or more of $R^1$, $R^2$, $R^3$, $R^4$, and $R^5$, is —NRC(O)$NR_2$. In some embodiments, one or more of $R^1$, $R^2$, $R^3$, $R^4$, and $R^5$, is —$NRSO_2R$, —$N^-(O)R_2$. In some embodiments, one or more of $R^1$, $R^2$, $R^3$, $R^4$, and $R^5$, is —OP(0)$R_2$. In some embodiments, one or more of $R^1$, $R^2$, $R^3$, $R^4$, and $R^5$, is —OP(O)(OR)$_2$. In some embodiments, one or more of $R^1$, $R^2$, $R^3$, $R^4$, and $R^5$, is —OP(O)(OR)$NR_2$. In some embodiments, one or more of $R^1$, $R^2$, $R^3$, $R^4$, and $R^5$, is —OP(OXNR$_2$)$_2$. In some embodiments, one or more of $R^1$, $R^2$, $R^3$, $R^4$, and $R^5$, is —P(O)$R_2$. In some embodiments, one or more of $R^1$, $R^2$, $R^3$, $R^4$, and $R^5$, is —$SiR_3$. In some embodiments, one or more of $R^1$, $R^2$, $R^3$, $R^4$, and $R^5$, is —Si(OR)$R_2$. In some embodiments, one or more of $R^1$, $R^2$, $R^3$, $R^4$, and $R^5$, is

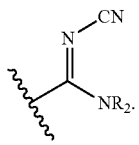

In some embodiments, $R^1$ is

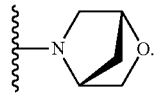 [SMILES: *N1C[C@H]2C[C@@H]1CO2]

In some embodiments, $R^2$ is —$CHF_2$. In some embodiments, $R^5$ is methyl.

As described above, each R, independently, is hydrogen, or an optionally substituted group selected from $C_{1-6}$ aliphatic, phenyl, a 3-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same carbon or nitrogen are optionally taken together with their intervening atoms to form a 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur, or a 5-9 membered heteroaryl ring having 1-4 heteroatoms independently selected from nitrogen, oxygen, and sulfur.

In some embodiments, R is hydrogen. In some embodiments, R is an optionally substituted $C_{1-6}$ aliphatic. In some embodiments, R is an optionally substituted phenyl. In some embodiments, R is an optionally substituted 3-7 membered saturated or partially unsaturated heterocyclic having 1-2 heteroatoms independently selected from nitrogen, oxygen, and sulfur. In some embodiments, R is an optionally substituted 5-6 membered heteroaryl ring having 1-4 heteroatoms independently selected from nitrogen, oxygen, and sulfur. In some embodiments, two R groups on the same carbon or nitrogen aze optionally taken together with their intervening atoms to form a 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur, or a 5-9 membered heteroaryl ring having 1-4 heteroatoms independently selected from nitrogen, oxygen, and sulfur.

As described above, each $R^A$, independently, is an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^A$ is an optionally substituted $C_{1-6}$ aliphatic. In some embodiments, $R^A$ is an optionally substituted phenyl. In some embodiments, $R^A$ is an optionally substituted 4-7 membered saturated or partially unsaturated heterocyclic ring having 1-2 heteroatoms independently selected from nitrogen, oxygen, and sulfur. In some embodiments, $R^A$ is an optionally substituted 5-6 membered heteroaryl ring having 1-4 heteroatoms independently selected from nitrogen, oxygen, and sulfur.

As described above, a, b, c, d, and e, independently, are selected from 0, 1, 2, 3, or 4.

In some embodiments, one or more of a, b, c, d, and e, is 0. In some embodiments, one or more of a, b, c, d, and e, is 1. In some embodiments, one or more of a, b, c, d, and e, is 2. In some embodiments, one or more of a, b, c, d, and e, is 3. In some embodiments, one or more of a, b, c, d, and e, is 4.

As described above, $R^6$ is hydrogen or $C_{1-6}$ aliphatic.

In some embodiments, $R^6$ is hydrogen. In some embodiments, $R^6$ is $C_{1-6}$aliphatic.

As described above, Ring A, Ring B, and Ring E, independently, are selected from phenyl, naphthyl, a 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur, or a 5-10 membered monocyclic or bicyclic heteroaryl ring having 1-4 heteroatoms independently selected from nitrogen, oxygen, and sulfur.

In some embodiments, one or more of Ring A, Ring B, and Ring E is phenyl. In some embodiments, one or more of Ring A, Ring B, and Ring E is naphthyl. In some embodiments, one or more of Ring A, Ring B, and Ring E is a 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur. In some embodiments, one or more of Ring A, Ring B, and Ring E is a 5-10 membered monocyclic or bicyclic heteroaryl ring having 1-4 heteroatoms independently selected from nitrogen, oxygen, and sulfur.

In some embodiments, Ring A is pyridinyl. In some embodiments, Ring B is pyrazolyl. In some embodiments, Ring E is 1,3-dihydro-2H-benzo[d]imidazol-2-onyl.

As described above, Ring C is a 4-6 membered saturated or partially unsaturated carbocyclic or heterocyclic ring having 1-2 heteroatoms selected from nitrogen, oxygen, and sulfur.

In some embodiments, Ring C is a 4-6 membered saturated or partially unsaturated carbocyclic or heterocyclic ring having 1-2 heteroatoms selected from nitrogen, oxygen, and sulfur.

In some embodiments, Ring C is cyclohexyl.

As described above, Ring D is a 4-6 membered saturated or partially unsaturated heterocyclic ring having, in addition to the nitrogen present, 0-2 heteroatoms selected from nitrogen, oxygen, and sulfur.

In some embodiments, Ring D is a 4-6 membered saturated or partially unsaturated heterocyclic ring having, in addition to the nitrogen present, 0-2 heteroatoms selected from nitrogen, oxygen, and sulfur.

In some embodiments, Ring D is piperidinyl.

As described above, L is a covalent bond or a bivalent, saturated or unsaturated, straight or branched $C_{1-10}$ hydrocarbon chain, wherein 0-6 methylene units of L are independently replaced by —CDH—, —CD$_2$—, —CRF—, —CF$_2$—, -Cy-, —O—, —NR—, —SiR$_2$—, —Si(OH)R—, —Si(OH)$_2$—, —P(O)OR—, —P(O)R—, —P(O)NR$_2$—, —S—, —OC(O)—, —C(O)O—, —C(O)—, —S(O)—, —SO$_2$—, —NRSO$_2$—, —SO$_2$NR—, —NRC(O)—, —C(O)NR—, —OC(O)NR—, —NRC(O)O—,

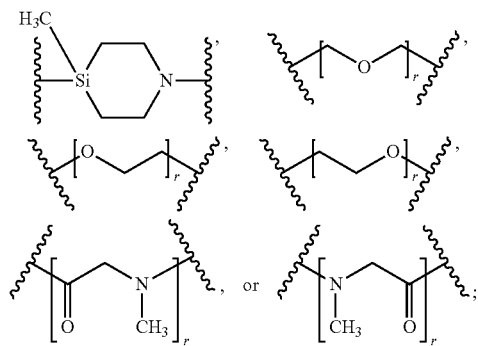

In some embodiments, L is a covalent bond. In some embodiments, L is a bivalent, saturated or unsaturated, straight or branched $C_{1-10}$ hydrocarbon chain, wherein 0-6 methylene units of L are independently replaced by —CDH—, —CD$_2$—, —CRF—, —CF$_2$—, -Cy-, —O—, —NR—, —SiR$_2$—, —Si(OH)R—, —Si(OH)$_2$—, —P(O)OR—, —P(O)R—, —P(O)NR$_2$—, —S—, —OC(O)—, —C(O)O—, —C(O)—, —S(O)—, —SO$_2$—, —NRSO$_2$—, —SO$_2$NR—, —NRC(O)—, —C(O)NR—, —OC(O)NR—, —NRC(O)O—,

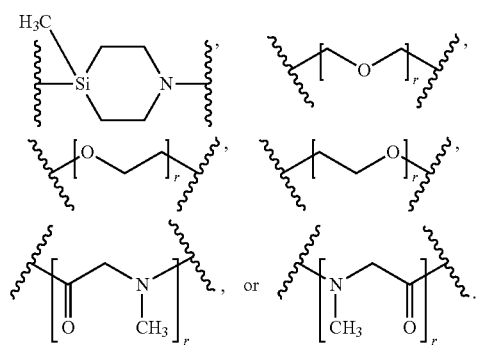

In some embodiments, L is —O(CH$_2$)$_{1-4}$—. In some embodiments, L is —(CH$_2$)$_{1-5}$—

In some embodiments, L is

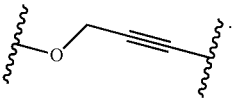 [SMILES: *C#CCO*]

As described above, each -Cy-, independently, is an optionally substituted bivalent ring selected from phenylenyl, an 8-10 membered bicyclic arylenyl, a 4-7 membered saturated or partially unsaturated carbocyclylenyl, a 4-12 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-12 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, and sulfur.

In some embodiments, -Cy- is an optionally substituted phenylenyl. In some embodiments, -Cy- an optionally substituted 8-10 membered bicyclic arylenyl. In some embodiments, -Cy- is an optionally substituted 4-7 membered saturated or partially unsaturated carbocyclylenyl. In some embodiments, -Cy- is an optionally substituted 4-12 membered saturated or partially unsaturated spiro carbocyclylenyl. In some embodiments, -Cy- is an optionally substituted 8-10 membered bicyclic saturated or partially unsaturated carbocyclylenyl. In some embodiments, -Cy- is an optionally substituted 4-7 membered saturated or partially unsaturated heterocyclylenyl having 1-2 heteroatoms independently selected from nitrogen, oxygen, and sulfur. In some embodiments, -Cy- is an optionally substituted 4-12 membered saturated or partially unsaturated spiro heterocyclylenyl having 1-2 heteroatoms independently selected from nitrogen, oxygen, and sulfur. In some embodiments, -Cy- is an optionally substituted 8-10 membered bicyclic saturated or partially unsaturated heterocyclylenyl having 1-2 heteroatoms independently selected from nitrogen, oxygen, and sulfur. In some embodiments, -Cy- is an optionally substituted 5-6 membered heteroarylenyl having 1-4 heteroatoms independently selected from nitrogen, oxygen, and sulfur. In some embodiments, -Cy- is an optionally substituted 8-10 membered bicyclic heteroarylenyl having 1-5 heteroatoms independently selected from nitrogen, oxygen, and sulfur.

As described above, r is 0, 1, 2, 3, 4, 5, 6, 7, 8, 9, or 10,

In some embodiments, r is 0. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

As described above, $X^1$ is a suitable leaving group.

In some embodiments, $X^1$ is a suitable leaving group. In some embodiments, the leaving group is halogen. In some embodiments, the leaving group is iodide.

As described above, G is an optionally substituted group selected from a $C_{1-6}$ aliphatic, phenyl, naphthyl, a 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur, or a 5-10 membered monocyclic or bicyclic heteroaryl ring having 1-4 heteroatoms independently selected from nitrogen, oxygen, and sulfur.

In some embodiments, G is an optionally substituted $C_{1-6}$ aliphatic. In some embodiments, G is an optionally substituted phenyl. In some embodiments, G is an optionally substituted naphthyl. In some embodiments, G is an optionally substituted 4-11 membered saturated or partially unsaturated monocyclic, bicyclic, bridged bicyclic, or spirocyclic carbocyclic or heterocyclic ring having 1-3 heteroatoms independently selected from nitrogen, oxygen, and sulfur. In some embodiments, G is an optionally substituted 5-10 membered monocyclic or bicyclic heteroaryl ring having 1-4 heteroatoms independently selected from nitrogen, oxygen, and sulfur.

In some embodiments, G is methyl.

In some embodiments, the present invention provides a compound of formula II, or a salt thereof, wherein each variable is independently as defined and described in embodiments herein.

In some embodiments, the present invention provides a compound of formula III, or a salt thereof, wherein each variable is independently as defined and described in embodiments herein.

In some embodiments, the present invention provides a compound of formula IV, or a salt thereof, wherein each variable is independently as defined and described in embodiments herein.

In some embodiments, the present invention provides a compound of formula V. or a salt thereof, wherein each variable is independently as defined and described in embodiments herein.

6. Analysis, Formulation, and Administration 6.1. Analysis

It has been discovered that certain impurities arise during the synthesis of compound I-1, such as the compounds shown in Table 1, above, or a stereoisomer or pharmaceutically acceptable salt thereof. Isolation and characterization of each impurity is useful for a number of purposes. Generally, pharmaceutical compositions require a high level of purity to meet regulated standards for drug quality and purity. For example, in the synthesis of compound I-1, impurities are often formed, including degradants or by-products of manufacture, which may hinder the therapeutic effects of compound I-1 and/or may be toxic if present in high enough quantities. As such, it is desirable to have the ability to determine the presence and amounts of such impurities and to monitor the chemical purity, including stereochemical purity, of compound M. To do this, it is important to identify, isolate, and chemically characterize impurities, which can be used in chromatographic procedures as standards to confirm the purity of compound M.

Accordingly, in one aspect the present invention provides a method of preparing a disclosed compound, or a pharmaceutically acceptable salt thereof, comprising contacting an appropriate starting material or materials under conditions shown, e.g., in the Examples below, to prepare the compound or pharmaceutically acceptable salt thereof. In some embodiments, the compound or a pharmaceutically acceptable salt thereof is useful as a reference standard and/or in methods of determining the presence of an impurity in a sample, such as a sample of compound I-1, or a pharmaceutically acceptable salt thereof.

The present invention also provides methods for determining an impurity, comprising injecting a reference compound (e.g., compound I-2, I-3, I-4, I-5, I-6, I-7, I-8, or I-9) or a pharmaceutically acceptable salt thereof, into an HPLC column under a set of conditions to obtain a first HPLC chromatogram, wherein the amount and/or chemical identity of the compound present in the reference solution is known; injecting a sample solution comprising compound I-1, or a pharmaceutically acceptable salt thereof, into the HPLC column under said set of conditions to obtain a second HPLC chromatogram; and determining the presence and/or the amount of the compound in the sample solution. In some embodiments, the reference solution is injected multiple times. In some embodiments, the determining comprises comparing retention times of peaks in the first HPLC chromatogram and peaks in the second HPLC chromatogram to determine the presence of the compound in the sample solution. In other embodiments, the determining comprises quantifying peak areas of the sample solution and peak areas of the reference solution on the HPLC chromatograms and estimating from these the amount of the compound in the sample solution. In some embodiments, the HPLC column is a reverse phase column and the column is eluted using a mobile phase (e.g., water, acetonitrile, and a mineral or organic acid).

The present invention also provides methods for determining an impurity in a material consisting essentially of compound I-1, or a pharmaceutically acceptable salt thereof, comprising injecting into an HPLC column, in a single or series of injections, a sample solution containing the material and spiked with a reference compound having a known chemical structure (e.g., compound I-2, I-3, I-4, I-5, I 6, I-7, I-8, or I-9) or a pharmaceutically acceptable salt thereof; obtaining an HPLC chromatogram; and determining the presence and/or the amount of the compound in the material. In some embodiments, the HPLC column is a reverse phase column and the column is eluted using a mobile phase (e.g., water, acetonitrile, and a mineral or organic acid). The method may further comprise documenting in a written form the chemical identity of the compound and the amount of the compound as an impurity.

The present invention also provides methods for determining an impurity in a material consisting essentially of compound I-1, or a pharmaceutically acceptable salt thereof, comprising injecting, in a single or series of injections, a solution in which the material is dissolved into an HPLC column and obtaining an HPLC chromatogram; determining the amount in the material of a compound having a known structure (e.g., compound I-2, I-3, I-4, I-5, I-6, I-7, I-8, or I-9) or a pharmaceutically acceptable salt thereof; and documenting in a written form the chemical identity of the compound and the amount of the compound as an impurity in the material. In some cases, the amount in the material of the compound is determined by (i) identifying a peak on the chromatogram that corresponds to a peak on a control chromatogram of a compound having the known structure, (ii) identifying a peak on the chromatogram that corresponds to a relative retention time of a compound having the known structure, and/or (iii) identifying a peak on the chromatogram that corresponds to a known amount of a spike of the compound having the known structure. In some embodiments, the HPLC column is a reverse phase column and the column is eluted using a mobile phase (e.g., water, acetonitrile, and a mineral or organic acid).

In some embodiments, the present invention provides compound I-2, I-3, I-4, I-5, I-6, I-7, I 8, or I-9, or a pharmaceutically acceptable salt thereof, in sufficient purity to enable its use as a reference or standard compound in various analytical methods (e.g., HPLC, HPTLC, GC, SFC, LCMS), as described more fully below. In some embodiments, the compound or pharmaceutically acceptable salt thereof may be isolated with at least 50% purity, at least 75% purity, at least 95% purity, or with at least 97% purity. In some embodiments, the compound or pharmaceutically acceptable salt thereof is isolated and/or packaged as a solid.

In another aspect, the present invention provides methods for determining the presence and/or amount of compound I-2, I-3, I-4, I-5, I-6, I-7, I-8, or I-9, or a pharmaceutically acceptable salt thereof.

For example, compound I-2, I-3, I-4, I-5, I-6, I-7, I-8, or I-9, or a pharmaceutically acceptable salt thereof, may be formed as an impurity during the synthesis of compound I-1. As used herein, the term "impurity" may refer to degradants which arise during storage of compound I-1 and/or by-products formed during the chemical manufacturing of compound I-1. In one embodiment, the method comprises injecting a reference solution comprising compound I-2, I-3, I-4, I-5, I-6, I-7, I-8, or I-9, or a pharmaceutically acceptable salt thereof, into an HPLC column under a set of conditions to obtain a first HPLC chromatogram wherein the amount and/or chemical identity of compound I-2, I-3, I-4, I-5, I-6, I-7, I-8, or I-9, or a pharmaceutically acceptable salt thereof, present in the reference solution is known, injecting a sample solution comprising compound I-1 into the HPLC column under the same set of conditions to obtain a second HPLC chromatogram, and comparing the first HPLC chromatogram with the second HPLC chromatogram to determine the presence and/or amount of the impurity (compound I-2, I-3, I-4, I-5, I-6, I-7, I-8, or I-9, or a pharmaceutically acceptable salt thereof). The reference solution may be formed by dissolving a sample (e.g., solid sample) of a compound of Formula I-1, or a pharmaceutically acceptable salt thereof, in a first solvent, and the sample solution may be formed by dissolving a solid sample in a second solvent. In some embodiments, the reference solution may contain an additional compound(s), wherein the amount and/or identity of the additional compound(s) is also known. In one embodiment, the sample (e.g., sample solution) may comprise compound I-1. It should be understood that the invention may encompass other samples suspected of containing compound I-2, I-3, I-4, I-5, I-6, I-7, I-8, or I-9, or a pharmaceutically acceptable salt thereof.

In some embodiments, the presence of compound I-2, I-3, I-4, I-5, I-6, I-7, I-8, or I-9, or a pharmaceutically acceptable salt thereof, in the sample solution may be determined by comparing retention times of peaks in the first HPLC chromatogram with the retention times of peaks in the second HPLC chromatogram. For example, the standard solution comprising compound I-2, I-3, I-4,1-5, I-6, I-7, I-8, or I-9, or a pharmaceutically acceptable salt thereof, may produce a chromatogram with a peak corresponding to compound I-2, I-3, I-4, I-5, I-6, I-7, I-8, or I-9, or a pharmaceutically acceptable salt thereof, and having a particular retention time. A sample solution may then be injected into the HPLC column under the same conditions as the standard solution, and the resulting chromatogram may be studied to determine if a peak exists at the same retention time as the peak corresponding to compound I-2, I-3, I-4, I-5, I-6, I-7, I-8, or I-9, or a pharmaceutically acceptable salt thereof, in the HPLC chromatogram of the standard solution. The existence of such a peak can indicate that compound I-2, I-3, I-4, I-5, I-6, I-7, I-8, or I-9, or a pharmaceutically acceptable salt thereof, is present in the sample. In another embodiment, the amount of a compound I-2, I-3, I-4, I-5, I-6, I-7, I-8, or I-9, or a pharmaceutically acceptable salt thereof, in the sample solution may be determined by comparing the area of peaks in the first HPLC chromatogram with the area of peaks in the second HPLC chromatogram, and calculating from these the content of compound I-2, I-3, I-4, I-5, I-6, I-7, I-8, or I-9, or a pharmaceutically acceptable salt thereof, in the sample solution.

In some embodiments, the present invention provides methods for determining an impurity in a material consisting essentially of compound I-1, wherein a sample solution containing the material and spiked with a reference compound having a known chemical structure of compound I-2, I-3, I-4, I-5, I-6, I-7, I-8, or I-9, or a pharmaceutically acceptable salt thereof, as described herein, is injected into an HPLC column and an HPLC chromatogram is obtained to determine the presence and/or the amount of the compound in the material.

Methods of the invention may further comprise documenting in a written form the chemical identity of the compound and the amount of the compound as an impurity in the material.

In some embodiments, the present invention provides methods for determining an impurity in a material consisting essentially of compound I-1, wherein a solution in which the material is dissolved is injected into an HPLC column and an HPLC chromatogram is obtained to determine the amount in the material of a compound known to have the structure of compound I-2, I-3, I-4, I-5, I-6, I-7, I-8, or I-9, or a pharmaceutically acceptable salt thereof, as described herein. The chemical identity of the compound and the amount of the compound as an impurity in the material may then be documented. The amount in the material of the compound may be determined by (i) identifying a peak on the chromatogram that corresponds to a peak on a control chromatogram, (ii) identifying a peak on the chromatogram that corresponds to a relative retention time of a compound known to have the structure of compound I-2, I-3, I-4, I-5, I-6, I-7, I-8, or I-9, or pharmaceutically acceptable salt thereof, and/or (iii) identifying a peak on the chromatogram that corresponds to a known amount of a spike of the compound known to have the structure of compound I-2, I-3, I-4, I-5, I-6, I-7, I-8, or I-9, or a pharmaceutically acceptable salt thereof.

Some embodiments of the invention may be useful in determining the amount and/or presence of compound I-2, I-3, I-4, I-5, I-6, I-7, I-8, or I-9, or a pharmaceutically acceptable salt thereof, in a sample comprising compound I-1. The sample may be a sample of freshly manufactured material or the sample may be one stored for a given period of time. In one embodiment, a sample of compound I-1 may be stored and periodically analyzed using methods described herein to determine the presence and/or amount of compound I-2, I-3, I-4, I-5, I-6, I-7, I-8, or I-9, or a pharmaceutically acceptable salt thereof, in the sample which may have been formed by, for example, degradation of compound I-1. In some cases, the sample may be placed under stressed conditions, i.e. conditions to intentionally promote degradation of compound I-1 such as elevated temperatures and/or elevated humidity, wherein the sample is periodically analyzed using methods described herein to determine the presence and/or amount of compound I-2, I-3, I-4, I-5, I 6, I-7, I-8, or I-9, or a pharmaceutically acceptable salt thereof, in the sample.

6.2. Pharmaceutically Acceptable Compositions

In some embodiments, the invention provides a pharmaceutical composition comprising a provided composition as described in detail herein, infra, and a pharmaceutically acceptable carrier, adjuvant, or vehicle.

In some embodiments, the composition comprises compound I-1, or a pharmaceutically acceptable salt thereof, and one impurity compound selected from the group consisting of I-2, I-3, I-4, I-5, I-6, I-7, I-8, and I-9, or a pharmaceutically acceptable salt thereof, and a pharmaceutically acceptable carrier, adjuvant, or vehicle.

In some embodiments, the composition comprises compound I-1, or a pharmaceutically acceptable salt thereof, and two impurity compounds selected from the group consisting of I-2, I-3, I-4, I 5, I-6, I-7, I-8, and I-9, or a pharmaceutically acceptable salt thereof, and a pharmaceutically acceptable carrier, adjuvant, or vehicle.

In some embodiments, the composition comprises compound I-1, or a pharmaceutically acceptable salt thereof, and three impurity compounds selected from the group consisting of I-2, I-3, I-4, I-5, I-6, I-7, I-8, and I-9, or a pharmaceutically acceptable salt thereof, and a pharmaceutically acceptable carrier, adjuvant, or vehicle.

In some embodiments, the composition comprises compound I-1, or a pharmaceutically acceptable salt thereof, and four impurity compounds selected from the group consisting of I-2, I-3, I-4, I-5, I-6, I-7, I-8, and I-9, or a pharmaceutically acceptable salt thereof, and a pharmaceutically acceptable carrier, adjuvant, or vehicle.

In some embodiments, the composition comprises compound I-1, or a pharmaceutically acceptable salt thereof, and five impurity compounds selected from the group consisting of I-2, I-3, I-4, I 5, I-6, I-7, I-8, and I-9, or a pharmaceutically acceptable salt thereof, and a pharmaceutically acceptable carrier, adjuvant, or vehicle.

In some embodiments, the composition comprises compound I-1, or a pharmaceutically acceptable salt thereof, and six impurity compounds selected from the group consisting of I-2, I-3, I-4, I 5, I-6, I-7, I-8, and I-9, or a pharmaceutically acceptable salt thereof, and a pharmaceutically acceptable carrier, adjuvant, or vehicle.

In some embodiments, the composition comprises compound I-1, or a pharmaceutically acceptable salt thereof, and seven impurity compounds selected from the group consisting of I-2, I-3, I-4, I-5, I-6, I-7, I-8, and I-9, or a pharmaceutically acceptable salt thereof, and a pharmaceutically acceptable carrier, adjuvant, or vehicle.

In some embodiments, the composition comprises compound I-1, or a pharmaceutically acceptable salt thereof, and each of impurity compounds I-2, I-3, I-4, I-5, I-6, I-7, I-8, and I-9, or a pharmaceutically acceptable salt thereof, and a pharmaceutically acceptable carrier, adjuvant, or vehicle.

In some embodiments, the composition comprises compound I-1, or a pharmaceutically acceptable salt thereof, and one or more impurity compounds selected from the group consisting of I-2, I-3, I-4, I-5, and I-6, or a pharmaceutically acceptable salt thereof, and a pharmaceutically acceptable carrier, adjuvant, or vehicle.

In some embodiments, the composition comprises compound I-1, or a pharmaceutically acceptable salt thereof, and one impurity compound selected from the group consisting of I-2, I-3, I-4, I-5, and I-6, or a pharmaceutically acceptable salt thereof, and a pharmaceutically acceptable carrier, adjuvant, or vehicle.

In some embodiments, the composition comprises compound I-1, or a pharmaceutically acceptable salt thereof, and two impurity compounds selected from the group consisting of I-2, I-3, I-4, I 5, and I-6, or a pharmaceutically acceptable salt thereof, and a pharmaceutically acceptable carrier, adjuvant, or vehicle.

In some embodiments, the composition comprises compound I-1, or a pharmaceutically acceptable salt thereof, and three impurity compounds selected from the group consisting of I-2, I-3, I-4, I-5, and I-6, or a pharmaceutically acceptable salt thereof, and a pharmaceutically acceptable carrier, adjuvant, or vehicle.

In some embodiments, the composition comprises compound I-1, or a pharmaceutically acceptable salt thereof, and four impurity compounds selected from the group consisting of I-2, I-3, I-4, I 5, and I-6, or a pharmaceutically acceptable salt thereof, and a pharmaceutically acceptable carrier, adjuvant, or vehicle.

In some embodiments, the composition comprises compound I-1, or a pharmaceutically acceptable salt thereof, and each of impurity compounds I-2, I-3, I-4, I-5, and I-6, or a pharmaceutically acceptable salt thereof, and a pharmaceutically acceptable carrier, adjuvant, or vehicle.

In some embodiments, the composition comprises compound I-1, or a pharmaceutically acceptable salt thereof, and one or more impurity compounds selected from the group consisting of I-2, I 3, or I-5, or a pharmaceutically acceptable salt thereof, and a pharmaceutically acceptable carrier, adjuvant, or vehicle.

In some embodiments, the composition comprises compound I-1, or a pharmaceutically acceptable salt thereof, and one impurity compound selected from the group consisting of I-2, I-3, or I-5, or a pharmaceutically acceptable salt thereof, and a pharmaceutically acceptable carrier, adjuvant, or vehicle.

In some embodiments, the composition comprises compound I-1, or a pharmaceutically acceptable salt thereof, and two impurity compounds selected from the group consisting of I-2, I-3, or I-5, or a pharmaceutically acceptable salt thereof, and a pharmaceutically acceptable carrier, adjuvant, or vehicle.

In some embodiments, the composition comprises compound I-1, or a pharmaceutically acceptable salt thereof, and each of impurity compounds I-2, I-3, or I-5, or a pharmaceutically acceptable salt thereof, and a pharmaceutically acceptable carrier, adjuvant, or vehicle.

In some embodiments, the composition comprises compound I-1, or a pharmaceutically acceptable salt thereof, and compound I-2, or a pharmaceutically acceptable salt thereof, and a pharmaceutically acceptable carrier, adjuvant, or vehicle.

In some embodiments, the composition comprises compound I-1, or a pharmaceutically acceptable salt thereof, and compound I-3, or a pharmaceutically acceptable salt thereof, and a pharmaceutically acceptable carrier, adjuvant, or vehicle.

In some embodiments, the composition comprises compound I-1, or a pharmaceutically acceptable salt thereof, and compound I-4, or a pharmaceutically acceptable salt thereof, and a pharmaceutically acceptable carrier, adjuvant, or vehicle.

In some embodiments, the composition comprises compound I-1, or a pharmaceutically acceptable salt thereof, and compound I-5, or a pharmaceutically acceptable salt thereof, and a pharmaceutically acceptable carrier, adjuvant, or vehicle.

In some embodiments, the composition comprises compound I-1, or a pharmaceutically acceptable salt thereof, and compound I-6, or a pharmaceutically acceptable salt thereof, and a pharmaceutically acceptable carrier, adjuvant, or vehicle.

In some embodiments, the composition comprises compound I-1, or a pharmaceutically acceptable salt thereof, and compound I-7, or a pharmaceutically acceptable salt thereof, and a pharmaceutically acceptable carrier, adjuvant, or vehicle.

In some embodiments, the composition comprises compound I-1, or a pharmaceutically acceptable salt thereof, and compound I-8, or a pharmaceutically acceptable salt thereof, and a pharmaceutically acceptable carrier, adjuvant, or vehicle.

In some embodiments, the composition comprises compound I-1, or a pharmaceutically acceptable salt thereof, and compound I-9, or a pharmaceutically acceptable salt thereof, and a pharmaceutically acceptable carrier, adjuvant, or vehicle.

In some embodiments, the composition of the present invention comprising compound I-1, or a pharmaceutically acceptable salt thereof, and one or more of impurity compounds selected from I-2, I-3, I-4, I-5, I-6, I-7, I-8, and I-9, or a pharmaceutically acceptable salt thereof, is present in the pharmaceutically acceptable carrier, adjuvant, or vehicle from 1-90 wt % of the total weight of the pharmaceutical composition. In some embodiments, the composition of the present invention is present in about 5, about 10, about 15, about 20, about 25, about 30, about 35, about 40, about 45, about 50, about 55, about 60, about 65, about 70, about 75, about 80, about 85, or about 90 wt % of the total weight of the pharmaceutical composition. In some embodiments, the composition of the present invention is present in 20-40, 30-50, 40-60, or 50-70 wt % of the total weight of the pharmaceutical composition.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

6.3. Administration

In some embodiments, a pharmaceutical composition herein is administered in a single composition as a single dosage form. As described herein, a pharmaceutical composition herein may comprise compound I-1, or a pharmaceutically acceptable salt thereof, and one or more of impurity compounds selected from I-2, I-3, I-4, I-5, I-6, I-7, I-8, and I-9, or a pharmaceutically acceptable salt thereof. In some embodiments, the amounts of one or more impurity compounds I-2, I-3, I-4, I-5, I-6, I 7, I-8, and I-9, or a pharmaceutically acceptable salt thereof is as described herein. In some embodiments, a pharmaceutical composition comprising compound I-1, or a pharmaceutically acceptable salt thereof, further comprises one or more of compounds selected from I-2, I-3, I-4, I-5, I-6, I-7, I-8, and I-9, or a pharmaceutically acceptable salt thereof. In some embodiments, a pharmaceutical composition herein further comprises water, and/or one or more residual solvent. As also described herein, in some embodiments, the present invention provides a pharmaceutical composition comprising compound I-1 as the active ingredient, or a pharmaceutically acceptable salt thereof.

Compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrastemal, intrathecal, intrahepatic, intralesional and intracranial injection or infusion techniques. Preferably, the compositions are administered orally, intraperitoneally or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this disclosure may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this disclosure include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In certain embodiments, pharmaceutically acceptable compositions of this disclosure are formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, compound I-1 or a pharmaceutically acceptable salt thereof, may be administered orally at a dose of about 10 mg/kg to about 200 mg/kg, particularly at a dose of selected from about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, and about 90 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of compound I-1 or a pharmaceutically acceptable salt thereof, it may be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this disclosure with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

Compound I-1, or a pharmaceutically acceptable salt thereof, can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

7. Methods and Uses for Treating Disease

In some embodiments, the present disclosure provides a method of administering compound I 1, or a pharmaceutically acceptable salt thereof (in a composition comprising one or more impurity compound selected from the group consisting of I-2, I-3, I-4, I-5, I-6, I-7, I-8, and I-9, or a pharmaceutically acceptable salt thereof), to a patient in need thereof, wherein the patient suffers from an autoimmune/autoinflammatory disease or a hematological malignancy. In some embodiments, the autoimmune/autoinflammatory disease is a cutaneous autoimmune/autoinflammatory disease. In some embodiments, the present disclosure provides a method of treating an autoimmune/autoinflammatory disease and/or a hematological malignancy, comprising administering to a patient in need thereof a therapeutically effective amount of Compound I-1, or a pharmaceutically acceptable salt thereof (in a composition comprising one or more impurity compound selected from the group consisting of I-2, I-3, I 4, I-5, I-6, I-7, I-8, and I-9, or a pharmaceutically acceptable salt thereof). In some embodiments, an autoimmune/autoinflammatory disease is selected from atopic dermatitis (AD), rheumatoid arthritis (RA), and hidradenitis suppurative (HS).

In some embodiments, the autoimmune/autoinflammatory disease includes inflammatory or allergic conditions of the skin, for example psoriasis, generalized pustular psoriasis (GPP), psoriasis vulgaris, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus *foliaceus*, paraneoplastic pemphigus, epidermolysis bullosa acquisita, acne vulgaris, hidradenitis suppurativa, Sweet Syndrome, pyoderma gangrenosum, and other inflammatory or allergic conditions of the skin. In some embodiments, the inflammatory disease of the skin is selected from contact dermatitits, atopic dermatitis, alopecia areata, erythema multiforma, dermatitis herpetiformis, scleroderma, vitiligo, hypersensitivity angiitis, urticaria, bullous pemphigoid, pemphigus vulgaris, pemphigus *foliaceus*, paraneoplastic pemphigus, epidermolysis bullosa acquisita, or hidradenitis suppurativa.

In some embodiments, a composition comprising compound I-1, or a pharmaceutically acceptable salt thereof, and one or more impurity compound selected from the group consisting of I-2, I-3, I-4, I-5, I-6, I-7, I-8, and I-9, or a pharmaceutically acceptable salt thereof may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodemia, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this disclosure is selected from acute and chronic gout, chronic gouty arthritis, psoriasis, psoriatic arthritis, rheumatoid arthritis, juvenile rheumatoid arthritis, systemic juvenile idiopathic arthritis (SJIA), cryopyrin associated periodic syndrome (CAPS), adult onset Still's disease, macrophage activation syndrome (MAS), primary and secondary hemophagocytic lymphohistiocytosis (HLH), familial Mediterranean fever, NLRP 12 autoinflammatory syndrome, and osteoarthritis.

In some embodiments the inflammatory disease which can be treated is a TH17 mediated disease. In some embodiments the TH17 mediated disease is selected from systemic lupus erythematosus, multiple sclerosis, psoriasis vulgaris, hidradenitis suppurativa, and inflammatory bowel disease (including Crohn's disease or ulcerative colitis).

In some embodiments the inflammatory disease which can be treated according to the methods of this disclosure is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis or chronic rhinosinusitis with nasal polyps (CRSwNP).

In some embodiments, the present disclosure provides a method for treating a cutaneous autoimmune/autoinflammatory disease in a patient, such as atopic dermatitis (AD) and hidradenitis suppurativa (HS), comprising administering to the patient a therapeutically effective amount of a composition comprising compound I-1, or a pharmaceutically acceptable salt thereof, and one or more impurity compound selected from the group consisting of I-2, I-3, I-4, I-5, I-6, I-7, I-8, and I-9, or a pharmaceutically acceptable salt thereof.

In some embodiments, the present disclosure provides a method for treating AD in a patient, comprising administering to the patient a therapeutically effective amount of a composition comprising compound I-1, or a pharmaceutically acceptable salt thereof, and one or more impurity compound selected from the group consisting of I-2, I-3, I-4, I-5, I-6, I-7, I-8, and I-9, or a pharmaceutically acceptable salt thereof.

In some embodiments, the present disclosure provides a method for treating AD in a patient, comprising administering to the patient a therapeutically effective amount of a composition comprising compound I-1 HCl, and one or more impurity compound selected from the group consisting of I-2, I-3, I 4, I-5, I-6, I-7, I-8, and I-9, or a pharmaceutically acceptable salt thereof.

In some embodiments, the present disclosure provides a method for treating HS in a patient, comprising administering to the patient a therapeutically effective amount of a composition comprising compound I-1, or a pharmaceutically acceptable salt thereof, and one or more impurity compound selected from the group consisting of I-2, I-3, I-4, I-5, I-6, I-7, I-8, and I-9, or a pharmaceutically acceptable salt thereof.

In some embodiments, the present disclosure provides a method for treating HS in a patient, comprising administering to the patient a therapeutically effective amount of a composition comprising compound I-1 HCl, and one or more impurity compound selected from the group consisting of I-2, I-3, I 4, I-5, I-6, I-7, I-8, and I-9, or a pharmaceutically acceptable salt thereof.

In some embodiments, the present disclosure provides a method for treating RA in a patient, comprising administering to the patient a therapeutically effective amount of a composition comprising compound I-1, or a pharmaceutically acceptable salt thereof, and one or more impurity compound selected from the group consisting of I-2, I-3, I-4, I-5, I-6, I-7, I-8, and I-9, or a pharmaceutically acceptable salt thereof.

In some embodiments, the present disclosure provides a method for treating RA in a patient, comprising administering to the patient a therapeutically effective amount of a composition comprising compound I-1 HCl, and one or more impurity compound selected from the group consisting of I-2, I-3, I 4, I-5, I-6, I-7, I-8, and I-9, or a pharmaceutically acceptable salt thereof.

In some embodiments, the present disclosure provides a method for treating hematological malignancy in a patient, comprising administering to the patient a therapeutically effective amount of a composition comprising compound I-1, or a pharmaceutically acceptable salt thereof, and one or more impurity compound selected from the group consisting of I-2, I-3, I-4, I-5, I-6, I-7, I-8, and I-9, or a pharmaceutically acceptable salt thereof. In some embodiments, the present disclosure provides a method for treating hematological malignancy in a patient, comprising administering to the patient a therapeutically effective amount of a composition comprising compound I-1 HCl, and one or more impurity compound selected from the group consisting of I-2, I-3, I-4, I-5, I-6, I-7, I-8, and I-9, or a pharmaceutically acceptable salt thereof. In some embodiments, the hematological malignancy is leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, intravascular large B-cell lymphoma, AML, or MDS.

The following examples are merely illustrative of the present invention and should not be construed as limiting the scope of the invention in any way as many variations and equivalents that are encompassed by the present invention will become apparent to those skilled in the art upon reading the present disclosure. For example, some reactions described below may be carried out under a range of conditions, such as at a different temperature (4° C., 10° C., 25° C., etc.), substitution with other reagents and different amounts or concentration of reagents.

EXEMPLIFICATION

As depicted in the Examples below, in certain exemplary embodiments, I-1 HCl is prepared and characterized according to the following procedures. Synthesis of starting materials can be found, for example, in WO 2019/133531 and WO 2020/010227, the contents of which are incorporated herein by reference in their entireties.

EXAMPLE 1. Synthesis of I-1 HCl

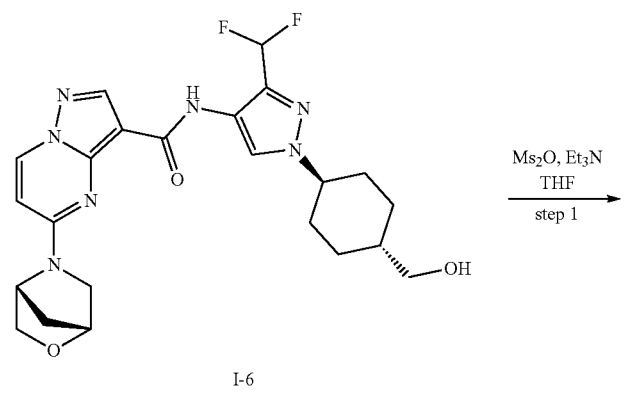

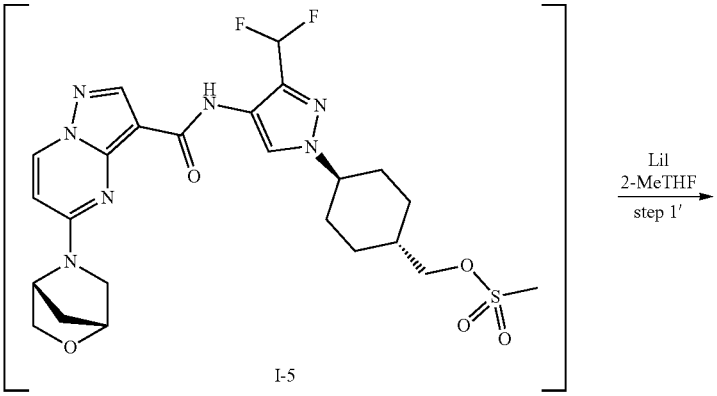

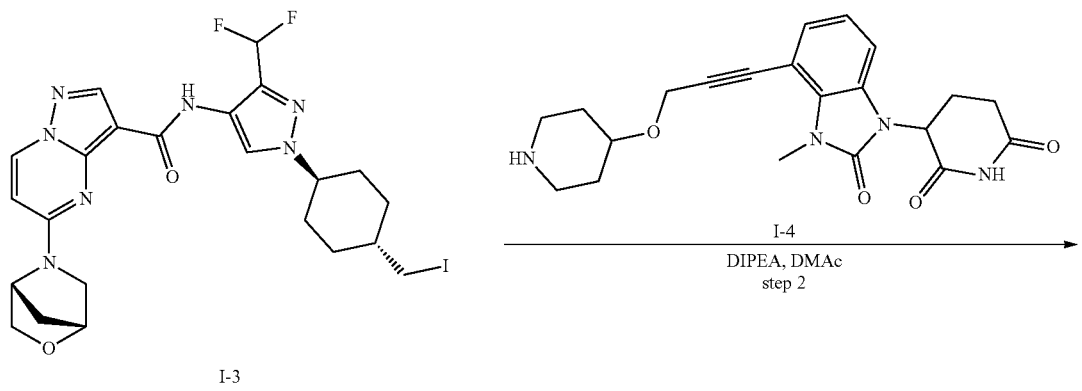

-continued

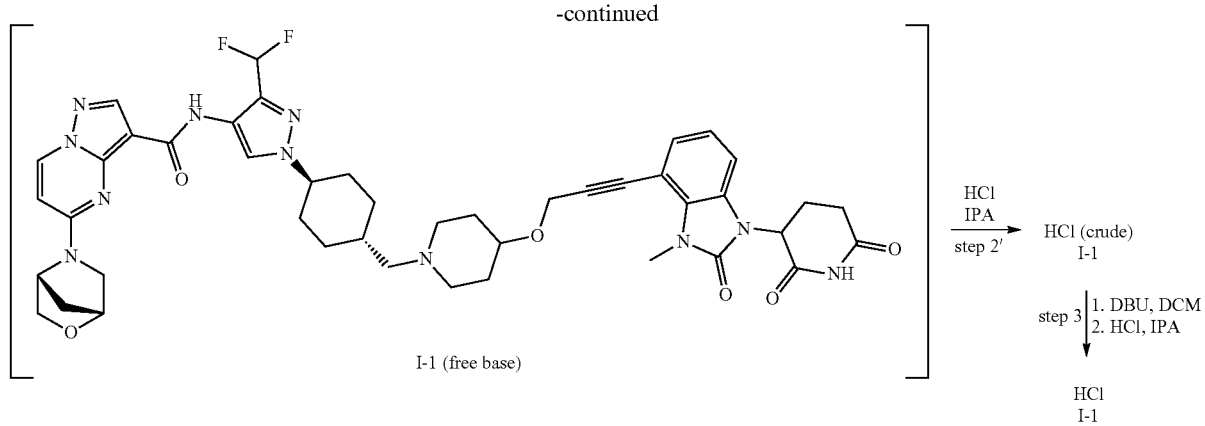

I-1 (free base)

→ HCl, IPA, step 2' → HCl (crude) I-1 step 3 { 1. DBU, DCM; 2. HCl, IPA }

↓

HCl
I-1

Step 1: Synthesis of I-3. A solution of the starting alcohol (I-6) and methanesulfonic anhydride (Ms$_2$O) in tetrahydrofuran (THF) was prepared in a reaction vessel and cooled to −15° C. Triethylamine (Et$_3$N) was then charged to the vessel, and the reaction mixture was aged until complete conversion of I-6 to I-5 was achieved (IPC, reaction monitoring by HPLC). The reaction mixture was warmed to room temperature, and an excess of lithium iodide (LiI) was added with stirring at 50° C. until complete conversion of I-5 to I-3 was observed (IPC, reaction monitoring by HPLC). The reaction mixture was then cooled and quenched with sodium bisulfite (NaHSO$_3$) solution. The batch was extracted with 2-methyltetrahydrofuran (2-McTHF), and the 2-MeTHF stream was azeotropically dried by atmospheric distillation to an acceptable level (IPC, moisture by Karl Fischer) prior to a solvent switch to N,N-dimethylacetamide (DMAc). The crude solution of I-3 was discharged from the reaction vessel through an in-line filter and assayed (IPC, weight % by HPLC) before being introduced directly into Step 2 of the process.

Step 2: Synthesis of I-1 HCl (crude). The DMAc solution of I-3 (from Step 1) and I-4 were charged to a reaction vessel and reacted at 75° C. with N,N-diisopropylethylamine (DIPEA) to form I-1 free base. Upon reaction completion (IPC, reaction monitoring by HPLC), the mixture was cooled to 50° C. before addition of hydrochloric acid (HCl) in 2-propanol (IPA). Seed crystals of I-1 HCl were then added, and the reaction mixture was aged at 50° C. Additional 2-propanol (IPA) was charged to the vessel. The crystallization slurry was further aged at 50° C. before cooling to room temperature to precipitate I-1 HCl from solution. The material was isolated by filtration, and the cake was washed with 2-propanol (IPA) and dried. The solid I-1 HCl (crude) was assayed (IPC, weight % by HPLC) and introduced directly into Step 3 of the process. It was noted that the Step 2 reaction mixture and crude API were determined to maintain 50:50 ratio of diastereomers.

Step 3: Preparation of I-1 HCl. The I-1 HCl (crude) material from Step 2 was suspended in dichloromethane (DCM) in a reaction vessel, and 1,8-diazabicyclo[5.4.0]undec-7-ene (DBU) was added while maintaining the contents of the vessel below 25° C. The mixture was agitated to form a solution, and then an aqueous solution of potassium phosphate monobasic (KH2PO4) was added. The organic phase was discharged, and the vessel was cleaned with rinses of N,N-dimethylacetamide (DMAc), water, 2-propanol (IPA), and dichloromethane (DCM) before charging the organic phase back into the vessel via an in-line filter. Dichloromethane (DCM) was added, washing the in-line filter, followed by addition of 2-propanol (IPA) and heating to 35° C. Sequentially, hydrochloric acid (HCl) in IPA and I-1 HCl seed crystals are charged to the vessel, and I-1 HCl precipitates as the mixture ages and cools to 20° C. The batch is filtered, and the cake was washed with dichloromethane (DCM) and 2-propanol (IPA) before drying in a vacuum oven at 60° C. In-process measurements of crystallinity (XRPD) and residual solvent levels (GC) of the dried I-1 HCl are completed prior to packaging.

EXAMPLE 2. Characterization of I-1 HCl Drug Substance

Justification of Specification

The release specification for I-1 HCl drug substance and the justification of the limit for each drug substance attribute shown in Table 2 and is discussed in the sections below.

TABLE 2

I-1 HCl Drug Substance Specification

| Test | Acceptance Criteria | Analytic Method |
|---|---|---|
| Description | White to off-white to beige powder | Visual |
| Identification (FTIR) | Conforms to reference spectrum | USP <197A> |
| Identification (HPLC) | Conforms to reference spectrum | HPLC |
| Assay (on anhydrous solvent-free basis, % wt/wt) as HCl salt | 95-105% | HPLC |
| HPLC Purity (area percent) | ≥97.0% | HPLC |
| Impurities (Area %) | Report ≥0.05% | HPLC |
| Specified Impurity, I-2 | ≤2.0% | |
| Individual Unspecified Impurities | ≤0.7% | |
| Total Impurities | ≤3.0% | |
| Diastereomeric Ratio | Report Results | HPLC |
| Residual Solvents | | GC |
| Dichloromethane | ≤600 ppm | |
| N,N-Dimethylacetamide | ≤1090 ppm | |
| Tetrahydrofuran | ≤720 ppm | |
| Isopropanol | ≤5000 ppm | |
| 2-Methyltetrahydrofuran | ≤5000 ppm | |
| Elemental Impurities | | USP <233> |
| Cadmium | ≤5 ppm | |
| Lead | ≤5 ppm | |
| Arsenic | ≤15 ppm | |
| Mercury | ≤30 ppm | |
| Cobalt | ≤50 ppm | |

TABLE 2-continued

I-1 HCl Drug Substance Specification

| Test | Acceptance Criteria | Analytic Method |
|---|---|---|
| Vanadium | ≤100 ppm | |
| Nickel | ≤200 ppm | |
| Palladium | ≤100 ppm | |
| Lithium | ≤550 ppm | |
| Copper | ≤3000 ppm | |
| Water Content (% wt/wt) | Report Results | USP <921> |
| Counterion Analysis (% wt/wt) | 3.3-4.5% | Titration |
| Chloride | | |
| Residue of Ignition | ≤0.5% | USP<281> |
| Crystallinity | Conforms to reference pattern | USP<941> |
| Particle Size Distribution (μm) | Report D10, D50, D90 and MV | USP<429> |
| Isopropyl Chloride Content | ≤3000 ppm | GC |
| Specified Impurities | | HPLC-MS |
| I-3 | ≤30 ppm | |
| I-5 | ≤30 ppm | |
| Microbial Enumeration Tests | | USP<61> |
| Total Aerobic Microbial Count (TAMC) | ≤$10^3$ cfu/g | USP<62> |
| Total Combined Yeasts and Molds Count (TYMC) | ≤$10^2$ cfu/g | |
| *E. coli* | Absence in 1 g | |

DESCRIPTION

Batches of I-1 HCl are visually inspected for color and physical characteristics. The description of the drug substance is "white to off-white to beige powder" based on observations from I-1 HCl produced in development batches.

Identification by FTIR

Infrared (IR) spectroscopy was used to verify the identity of the drug substance. Identification was based on comparison of the sample IR spectrum to the spectrum of I-1 HCl reference standard. Identification by HPLC High Performance Liquid Chromatography (HPLC) was used to verify the identity of the drug substance. Identification was based on comparison of the sample retention time to the retention time of the I-1 HCl reference standard, using method parameters are listed in Table 3.

TABLE 3

Assay and Impurities Method Parameters

| | |
|---|---|
| Technique | Reversed-phase HPLC |
| Column | Zorbax Eclipse Plus C18, 150 × 3.0 mm, 3.5 μm |
| Mobile phases | A: 0.04% TFA in water<br>B: 0.02% TFA in acetonitrile |
| Detection | UV detection at 225 nm |
| Column temperature | 40° C. |
| Pump program | Gradient |
| Flow rate | 0.9 mL/min |
| Sample Preparation | 0.4 mg/mL<br>Diluent = 50:50:0:2 acetonitrile:water: TFA |

Purity and Assay by HPLC

The HPLC Purity limit (≥97.0% area) of I-1 HCl was based on results obtained from development lots and conforms to limits normally established for early-phase development. The Table 3 method was used to identify impurities of I-1 HCl. The gradient method resolves all known related impurity peaks and was shown to be stability indicating in forced degradation studies. The limit for assay (on anhydrous solvent-free basis) as HCl salt by HPLC is established as 95-105% (w/w). The limit is based on results obtained from development lots and conforms to limits normally established for early-phase development.

Stereochemical Control

I-1 HCl was manufactured as an approximately 50:50 mixture of diastereomers, (S)-I-1 and (R)-I-1. The molecular structure of I-1 HCl contains three chiral centers, including two fixed/stable centers around the morpholine ring (RR) and one epimerizable chiral center (R/S). Additionally, the trans configuration at the cyclohexyl ring is desired. All of the stereogenic features are introduced through the starting materials. Table 4 lists the compound identifiers of the potential isomers which may be present in I-1 HCl.

TABLE 4

Stereochemical Isomers

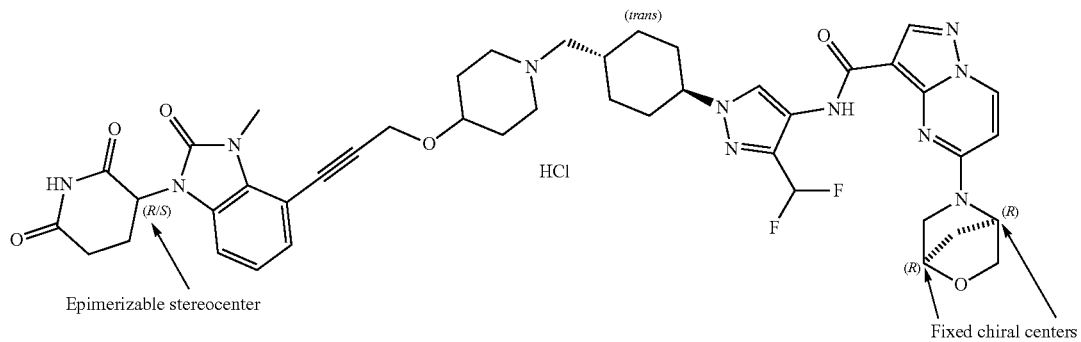

| | Configuration | | |
|---|---|---|---|
| I-# | Epimerization Center | Cyclohexyl Ring | Morpholine Ring |
| (S)-I-1 | S | trans | R,R |
| (R)-I-1 | R | trans | R,R |
| I-2 | S/R | cis | R,R |

TABLE 4-continued

| S,S-morph-I-1 | S/R | trans | S,S |
| S,S-morph-I-2 | S/R | cis | S,S |

Diastereomeric Ratio

The diastereomeric ratio of (S)-I-1:(R)-I-1 is determined by chiral HPLC. The method parameters are listed in Table 5.

TABLE 5

| Diastereomeric Ratio Method Parameters | |
| --- | --- |
| Technique | Reversed-phase HPLC |
| Column | Agilent Poroshell 120 Chiral-V, 100 × 4.6 mm, 2.7 μm |
| Mobile phases | A: 20 mM Ammonium acetate, pH 4.0<br>B: Acetonitrile |
| Detection | UV detection at 225 nm |
| Column temperature | 40° C. |
| Pump program | Gradient |
| Flow rate | 0.7 mL/min |
| Sample Preparation | 1.0 mg/mL<br>Diluent = 50:50:0:2 acetonitrile:water: TFA |

Unspecified Impurities by HPLC

Impurities above the reporting threshold will be reported (≥0.05% area). The limit for individual unspecified impurities in I-1 HCl drug substance is derived from literature guidance, e.g., Harvey, et al., "Management of organic impurities in small molecule medicinal products: Deriving safe limits for use in early development", Regul. Toxicol. Pharmacol. 2017, 84:116-23, to justify an acceptable limit of 5 mg/day or 0.7% (whichever is lower) for non-mutagenic impurities in early clinical studies (<6 months). The planned Multiple Ascending Dose clinical study has an estimated maximum daily dose (MDD) of 500 mg (as freebase). The upper impurity limit corresponding to this MDD is calculated to be 1.0%, according to Eqn 1. However, this is superseded by the upper limit of 0.7%, as required by Harvey, et al.

$$\frac{\text{daily impurity limit}}{\text{daily dose}} \times 100 = \frac{5 \text{ mg/day}}{500 \text{ mg/day}} \times 100 = 1.0\% \qquad \text{Eqn 1}$$

Specified Impurities by HPLC-MS

Several impurities may be found in I-1 HCl using the synthesis depicted in Example 1. Specified impurities are listed in Table 6.

TABLE 6

| | | | | |
| --- | --- | --- | --- | --- |
| I-# | Structure | MW (Da) | Origin of Impurity | Analytical Method |
| I-2 | | 865.94 | Process Impurity | HPLC (RRT 1.03) |
| I-3 | | 565.60 | Process Intermediate | LCMS |

Specified Impurities

TABLE 6-continued

Specified Impurities

| I-# | Structure | MW (Da) | Origin of Impurity | Analytical Method |
|---|---|---|---|---|
| I-5 | 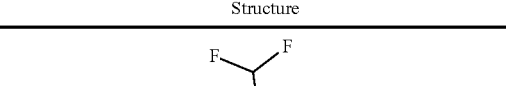 | 597.41 | Process Intermediate | LCMS |

The trans configuration at the cyclohexyl ring of I-1 is a result of the synthesis. Additionally, the crystallization process steps upgrade the trans purity. The cis configuration (I-2) in the I-1 HCl was detected using the HPLC method in Table 3. The limit for specified impurity I-2 is ≤2%. I-3 and I-5 are measured by the reversed-phase HPLC method with mass spectrometry detection (MS) in Table 7 and are potential genotoxic impurities discussed below.

TABLE 7

Specified Impurities Method Parameters

| | |
|---|---|
| Technique | Reversed-phase HPLC |
| Column | Agilent Zorbax SB-C18, 50 × 2.1 mm, 1.8 μm |
| Mobile phases | A: Water<br>B: 0.1% Formic acid in acetonitrile |
| Column temperature | 40° C. |
| Pump program | Gradient |
| Flow rate | 0.4 mL/min |

TABLE 7-continued

Specified Impurities Method Parameters

| | |
|---|---|
| Sample Preparation | 1.0 mg/mL<br>Diluent = 4:1 acetonitrile:water |
| Detection System | Single Quadrupole Mass Spectrometer |
| Ionization | Electrospray Positive |
| Mode | SIM (m/z 566, 598) |

Potential Genotoxic Impurities

An assessment of the possible formation of potential genotoxic impurities (PGIs) during the manufacture of I-1 HCl was conducted according to ICH M7(R1)—Assessment and Control of DNA Reactive (Mutagenic) Impurities in Pharmaceuticals to Limit Potential Carcinogenic Risk (published 31 Mar. 2017). The potential mutagenicity of the starting materials, intermediates, and potential impurities and degradation products was evaluated in silico by means of DEREK 6.0.0 Nexus 2.2.0 (mutagenicity only) and LSMA Version 2.4.5-7 (mutagenicity suite). The results are summarized in Table 8.

TABLE 8

Summary of In Silico Mutagenicity Findings

| I-# | Structure | Origin of Impurity | DEREK Results[a] | LSMA Results[b] (Bacterial Mut.) | M7 Class |
|---|---|---|---|---|---|
| I-3 | 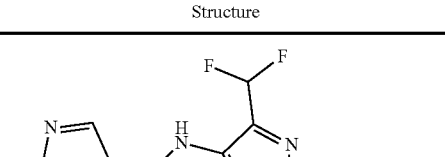 | Process Intermediate | Plausible | Positive Pp = 0.866 | 3 |

TABLE 8-continued

Summary of In Silico Mutagenicity Findings

| I-# | Structure | Origin of Impurity | DEREK Results[a] | LSMA Results[b] (Bacterial Mut.) | M7 Class |
|---|---|---|---|---|---|
| I-4 | 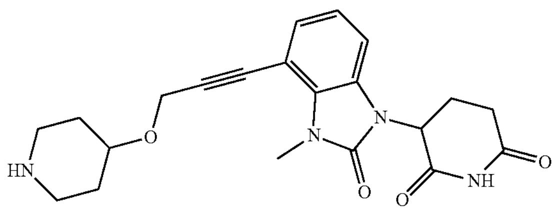 [SMILES: Cn1c(=O)n(C2CCC(=O)NC2=O)c2cccc(C#CCOC3CCNCC3)c21] | Starting Material | Inactive | Not in Domain Pp = 0.165 | 5 |
| I-5 | 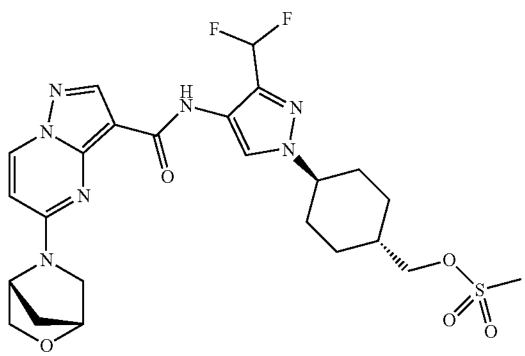 [SMILES: CS(=O)(=O)OC[C@H]1CC[C@H](n2cc(NC(=O)c3cnn4ccc(N5C[C@H]6C[C@@H]5CO6)nc34)c(C(F)F)n2)CC1] | Process Intermediate | Plausible | Positive Pp = 0.988 | 3 |
| I-6 | 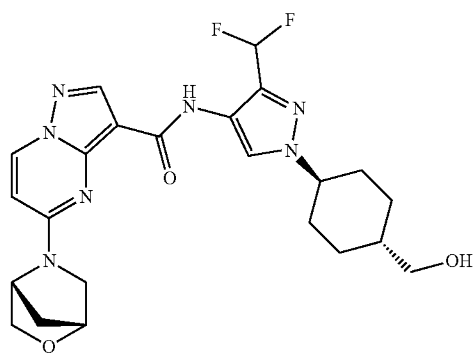 [SMILES: O=C(Nc1cn([C@H]2CC[C@H](CO)CC2)nc1C(F)F)c1cnn2ccc(N3C[C@H]4C[C@@H]3CO4)nc12] | Starting Material | Inactive | Starting Material | 5 |
| I-7 | 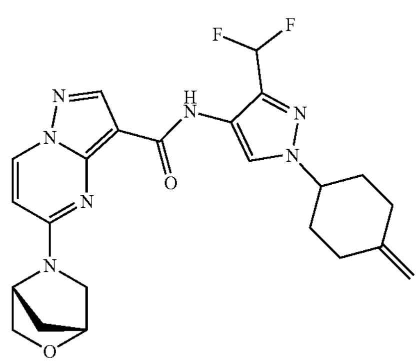 [SMILES: C=C1CCC(n2cc(NC(=O)c3cnn4ccc(N5C[C@H]6C[C@@H]5CO6)nc34)c(C(F)F)n2)CC1] | Potential Degradation Product | Inactive | Negative Pp = 0.238 | 5 |

TABLE 8-continued

Summary of In Silico Mutagenicity Findings

| I-# | Structure | Origin of Impurity | DEREK Results[a] | LSMA Results[b] (Bacterial Mut.) | M7 Class |
|---|---|---|---|---|---|
| I-8 | 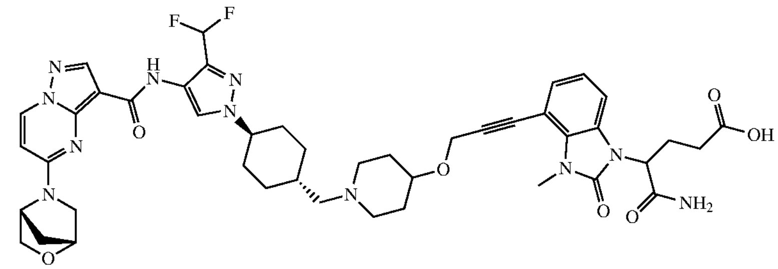 [SMILES: Cn1c(=O)n(C(CCC(=O)O)C(N)=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21] | Potential Degradation Product | Inactive | Not in Domain Pp = 0.0151 | 5 |
| I-9 | 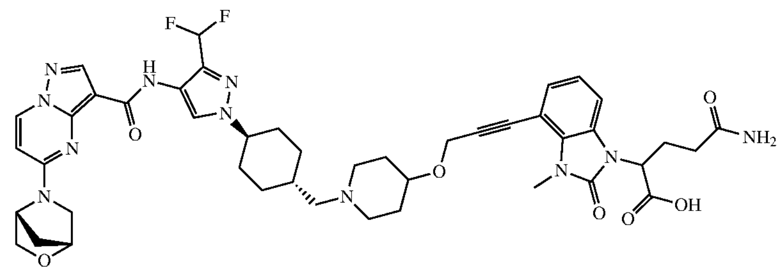 [SMILES: Cn1c(=O)n(C(CCC(N)=O)C(=O)O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21] | Potential Degradation Product | Inactive | Not in Domain Pp = 0.0151 | 5 |

[a]Mutagenicity in vitro in: bacterium; *E. coli*; and *S. typhimurium*.
[b]LSMA Positive Mutagenicity Prediction Probability (Pp) < 0.4 is negative; > is positive; and 0.4-0-6 is indeterminate.

I-3 was predicted to be plausible for in vitro mutagenicity in DEREK and positive in LSMA, due to the presence of an alkyl iodide feature. This feature is known to be an alkylating agent with several examples showing positive results in the Ames test. Methyl iodide has also shown positive results in rodent carcinogenicity assays. Therefore, I-3 is considered potentially mutagenic and classified as Class 3, per ICH M7.

I-5 was predicted to be plausible for in vitro mutagenicity in DEREK and positive in LSMA due to the presence of an alkyl sulfonate ester feature. This feature is known to be an alkylating agent with several examples showing positive results in the Ames test. There are also compounds that have shown positive results in rodent carcinogenicity assays. Therefore, I-5 is considered potentially mutagenic and classified as Class 3, per ICH M7.

Since I-3 and I-5 were considered potentially mutagenic (Class 3), the content of these impurities was tested by HPLC-MS. The limit of each impurity was derived from ICH M7($R_1$). For a planned Multiple Ascending Dose clinical study that has an estimated maximum daily dose of 500 mg (520 mg as HCl salt) and duration of treatment for not more than 12 months, the M7 (R1) guidance indicates a daily intake of 20 µg/day for treatment duration of up to 12 months. From these values, the calculated limit for I-3 and I-5 each is ≤38 ppm, as shown in Eqn 2. The specified limit for each compound was rounded down to ≤30 ppm.

$$\frac{\text{daily impurity limit}}{\text{daily dose}} \times 100 = \frac{20 \text{ ug/day}}{8.520 \text{ g/day}} \times 100 = 38 \text{ ppm} \quad \text{Eqn 2}$$

I-4 was predicted to be inactive for in vitro mutagenicity in DEREK, with no misclassified or unclassified features, and not in domain in LSMA, due to a lack of analogues. None of the features present in the impurity are significantly associated with positive mutagenicity results. All of the features present in the impurity are accounted for in the API, which was negative in the preliminary Ames test. Therefore, I-4 was considered non-mutagenic and classified as Class 5, per ICH M7.

I-6 was predicted to be inactive for in vitro mutagenicity in DEREK, with no misclassified or unclassified features, and negative in LSMA. None of the features present in the impurity are significantly associated with positive mutagenicity results. All of the relevant features are present on the API, which was negative in a preliminary Ames test. Therefore, I-6 was considered non-mutagenic and classified as Class 5, per ICH M7.

Elimination impurity I-7 was predicted to be inactive for in vitro mutagenicity in DEREK, with no misclassified or unclassified features, and negative in LSMA. None of the features present in the impurity are significantly associated with positive mutagenicity results. Additionally, most of the features in this compound are present on the I-1 in a similar chemical space. The only differing feature between the impurity and I-1 is the methylenecyclohexane, which is not expected to contribute toward positive mutagenicity. Therefore, elimination impurity I-7 was considered nonmutagenic and classified as Class 5, per ICH M7.

Ring open impurity isomer 1-8 and isomer 1-9 were predicted to be inactive for in vitro mutagenicity in DEREK, with no misclassified or unclassified features, and not in domain in LSMA, due to a lack of analogues. None of the features present in the impurities are significantly associated with positive mutagenicity results. These impurities are very similar in structure to 1-1. None of the differing features are associated with positive mutagenicity results. Therefore, ring open impurity isomer I-8 and isomer I-9 are considered non-mutagenic and classified as Class 5, per ICH M7.

Residual Solvents

Residual solvents used in the process to prepare I-1 HCl are listed in Table 9, with the Option 1 limits established by ICH Q3C(R$_6$)—Impurities: Guideline for Residual Solvents, adopted 20 Oct. 2016. Additionally, the limit for 2-methyltetrahydrofuran is based on the Class 3 designation suggested by ICH draft guidance Q3C(R$_8$)—Impurities: Guideline for Residual Solvents, PDE for 2-Methyltetrahydrofuran, Cyclopentyl methyl ether, and tertiary-Butyl alcohol, endorsed on 25 Mar. 2020.

TABLE 9

Residual Solvents

| Solvent | Process Step | ICH Limit (ppm) |
|---|---|---|
| Dichloromethane | 3 | ≤600 ppm |
| N,N-Dimethylacetamide | 1, 2, 3 | ≤1090 ppm |
| Tetrahydrofuran | 2, 3 | ≤720 ppm |
| Isopropanol | 2, 3 | ≤5000 ppm |
| 2-Methyltetrahydrofuran |  | ≤5000 ppm[a] |

[a]Based on the Class 3 designation suggested by ICH draft guidance Q3C(R8) - Impurities: Guideline for Residual Solvents, PDE for 2-Methyltetrahydrofuran, Cyclopentyl methyl ether, and tertiary-Butyl alcohol, endorsed 25 Mar. 2020.

Residual solvent content is determined by gas chromatography (GC) with a flame ionization detector (FID). The method parameters are listed in Table 10.

TABLE 10

Residual Solvents Method Parameters

| Technique | Gas Chromatography |
|---|---|
| Column | DB-624, 30 m × 0.32 mm × 1.8 μm |
| Carrier gas | Hydrogen at 1.0 mL/min, constant flow |
| Detection | FID at 240° C. |
| Sample introduction | Liquid injection |
| Oven program | Thermal gradient |
| Sample Preparation | 100 mg/mL |
|  | Diluent = 1-methyl-2-pyrrolidinone |

Isopropyl chloride is a potential byproduct of the manufacturing process. Isopropyl chloride is a Class 2 compound per ICH M7(R$_1$)—Assessment and Control of DNA Reactive (Mutagenic) Impurities in Pharmaceuticals to Limit Potential Carcinogenic Risk, dated 31 Mar. 2017. The default Threshold of Toxicological Concern (TTC) for monofunctional alkyl chlorides can be raised ten times the default TTC listed in the M7(R$_1$) guidance. Therefore, based on the duration of treatment of not more than 12 months, the TTC limit for isopropyl chloride is 200 μg/day. A planned Multiple Ascending Dose clinical study that has an estimated maximum daily dose of 500 mg (520 mg as HCl salt), the calculated limit for isopropyl chloride is ≤385 ppm. The specified limit was rounded down to ≤300 ppm. The content of isopropyl chloride was determined by the method of Table 10.

Inorganic Impurities

I-1 HCl was tested using inductively coupled plasma mass spectrometry (ICP-MS) according to USP <233> to detect all Class 1 and Class 2A elements. The elements used in the process (palladium, copper, and lithium) are controlled at oral limits (up to 1 g/day dosing of I-1 HCl) established by ICH Q3D(R$_1$)—Guideline for Elemental Impurities, adopted 22 Mar. 2019. Table 11 lists the elemental impurities.

TABLE 11

Elemental Impurities

| Element | Class | Limit (ppm) |
|---|---|---|
| Cd | 1 | ≤5 ppm |
| Pb | 1 | ≤5 ppm |
| As | 1 | ≤15 ppm |
| Hg | 1 | ≤30 ppm |
| Co | 2A | ≤50 ppm |
| V | 2A | ≤100 ppm |
| Ni | 2A | ≤200 ppm |
| Pd | 2B | ≤100 ppm |
| Li | 3 | ≤550 ppm |
| Cu | 3 | ≤3000 ppm |

Counterion Analysis

The counterion is chloride. The chloride ion content limit is set to 3.9±0.6%. The counterion content was determined by titration. The measurement is performed using a silver electrode against silver nitrate titrant. The limit is based on the results obtained for development batches and is consistent with a mono-HCl salt.

Residue on Ignition

Residue on Ignition was tested according to USP <281>. The limit for Residue on Ignition (ROI) was <0.5%. The limit is based on results obtained from development lots and conforms to limits normally established for early-phase development.

Crystallinity

The polymorphic form of the drug substance was determined by X-Ray Powder Diffraction (XRPD) according to USP <941>. Confirmation of form was based on comparison of the sample XRPD diffraction pattern to the diffraction pattern of I-1 HCl reference standard.

Water Content

Water content are measured by coulometric Karl Fischer titration according to USP <921>.

Microbial Enumeration Tests

Total Aerobic Microbial Count (TAMC), Total Combined Yeasts and Molds Count (TYMC), and *E. coli* are tested according to USP <61> and USP <62>.

* * * * *

While we have described a number of embodiments of this invention, it is apparent that our basic examples may be altered to provide other embodiments that utilize the compounds and methods of this invention. Therefore, it will be appreciated that the scope of this invention is to be defined by the application and claims rather than by the specific embodiments that have been represented by way of example.

The invention claimed is:

1. A composition comprising compound I-1:

I-1

[Chemical structure of compound I-1]

or a pharmaceutically acceptable salt thereof, and three or more impurity compounds selected from the group consisting of:

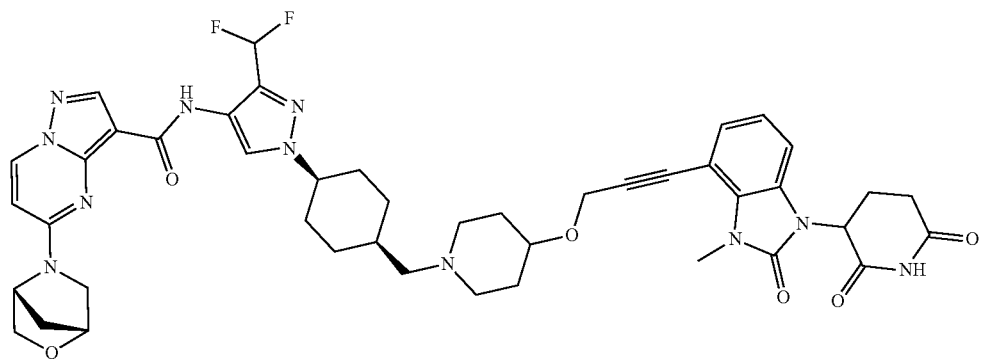
I-2
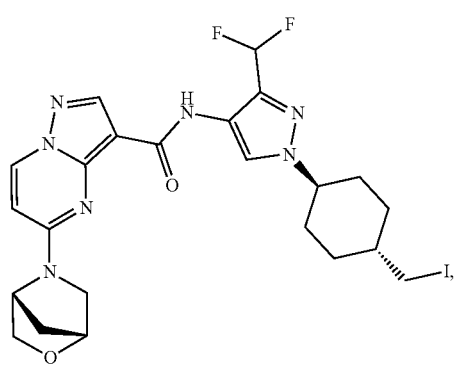
I-3
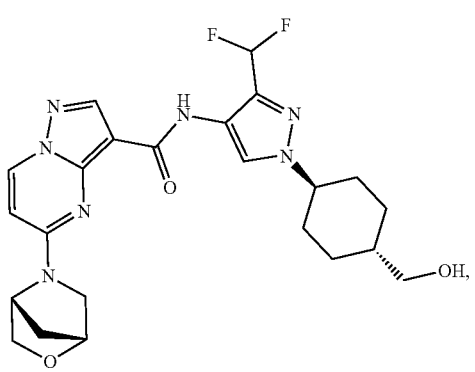
I-4
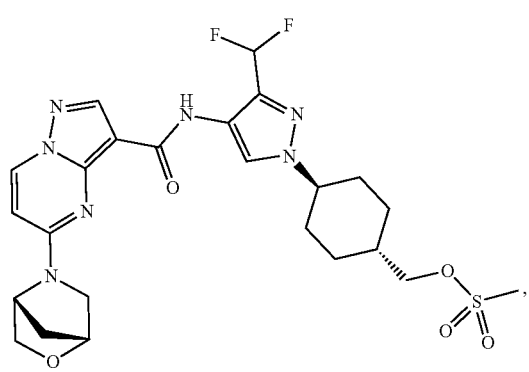
I-5
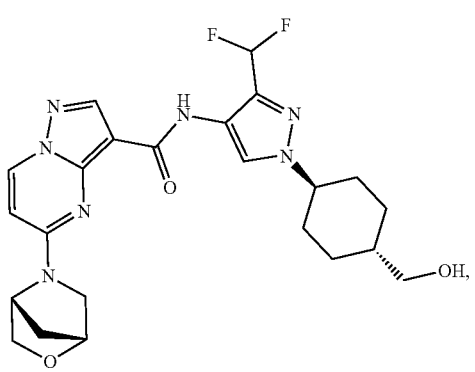
I-6
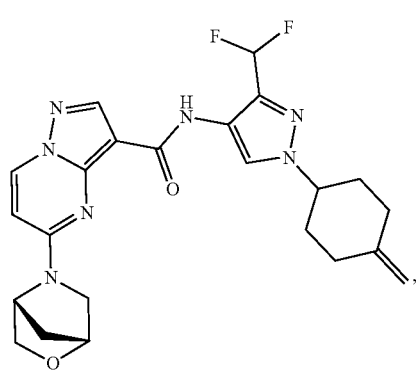
I-7

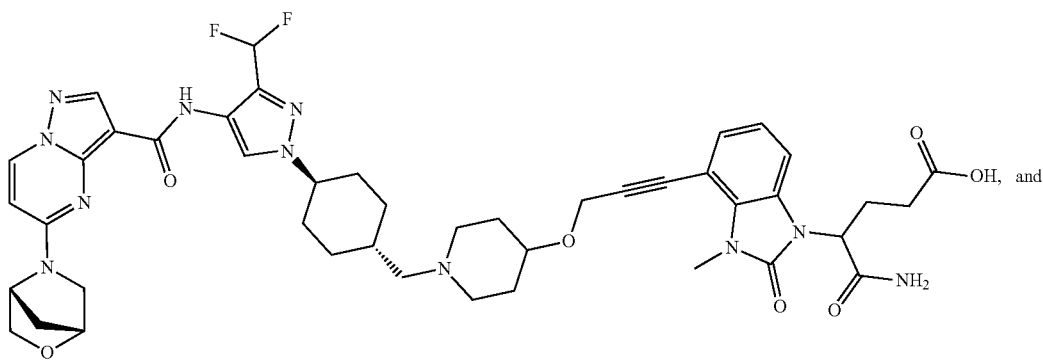

I-8

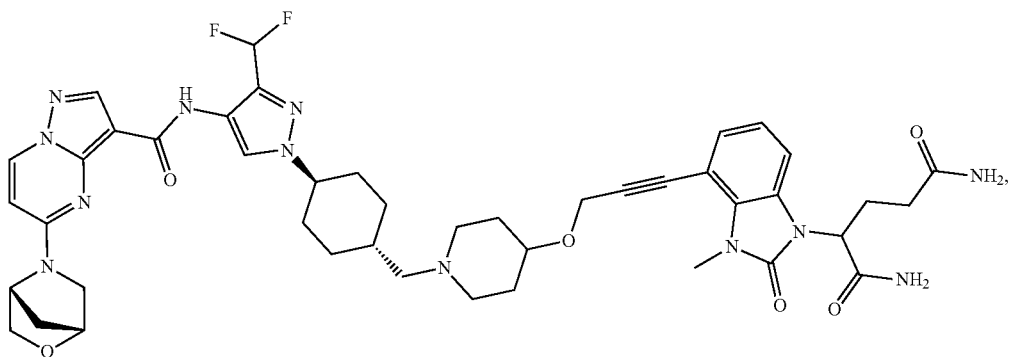

I-9 or a pharmaceutically acceptable salt thereof.

2. The composition of claim 1, wherein the composition comprises three impurity compounds selected from the group consisting of I-2, I-3, I-4, I-5, I-6, I-7, I-8, and I-9, or a pharmaceutically acceptable salt thereof.

3. The composition of claim 1, wherein the composition comprises four impurity compounds selected from the group consisting of I-2, I-3, I-4, I-5, I-6, I-7, I-8, and I-9, or a pharmaceutically acceptable salt thereof.

4. The composition of claim 1, wherein the composition comprises five impurity compounds selected from the group consisting of I-2, I-3, I-4, I-5, I-6, I-7, I-8, and I-9, or a pharmaceutically acceptable salt thereof.

5. The composition of claim 1, wherein the composition comprises six impurity compounds selected from the group consisting of I-2, I-3, I-4, I-5, I-6, I-7, I-8, and I-9, or a pharmaceutically acceptable salt thereof.

6. The composition of claim 1, wherein the composition comprises seven impurity compounds selected from the group consisting of I-2, I-3, I-4, I-5, I-6, I-7, I-8, and I-9, or a pharmaceutically acceptable salt thereof.

7. The composition of claim 1, wherein the composition comprises each of impurity compounds I-2, I-3, I-4, I-5, I-6, I-7, I-8, and I-9, or a pharmaceutically acceptable salt thereof.

8. The composition of claim 1, wherein each of impurity compounds I-4, I-6, I-7, I-8, and I-9, or a pharmaceutically acceptable salt thereof, is, independently, no more than about 0.7 area percent HPLC of the total weight of the composition.

9. The composition of claim 1, wherein impurity compound I-2 or a pharmaceutically acceptable salt thereof is no more than about 2.0 area percent HPLC of the total weight of the composition.

10. The composition Qf claim 1, wherein each of impurity compounds I-3 and I-5, or a pharmaceutically acceptable salt thereof, is, independently, no more than about 30 ppm.

11. The composition of claim 1, wherein the total impurity compounds of I-2, I-3, I-4, I-5, I-6, I-7, I-8, and I-9, or a pharmaceutically acceptable salt thereof, present in the composition is no more than about 3.0 area percent HPLC.

12. The composition of claim 1, wherein the purity of compound I-1, or a pharmaceutically acceptable salt thereof, in the composition is at least about 97.0 area percent HPLC.

13. A pharmaceutical composition comprising a composition of claim 1, and a pharmaceutically acceptable adjuvant, carrier, or vehicle.

14. The composition of claim 1, wherein the composition comprises at least one or more impurity compound selected from the group consisting of I-2, I-3, and I-5, or a pharmaceutically acceptable salt thereof.

15. The composition of claim 1, wherein the composition comprises at least one or more impurity compound selected from the group consisting of I-3 and I-5, or a pharmaceutically acceptable salt thereof.

16. The composition of claim 1, further comprising dichloromethane in the composition in an amount of no more than about 600 ppm or further comprising N,N-dimethylacetamide in the composition in an amount of no more than about 1090 ppm.

17. The composition of claim 1, further comprising tetrahydrofuran in the composition in an amount of no more than about 720 ppm or further comprising isopropanol in the composition in an amount of no more than about 5000 ppm.

18. The composition of claim 1, further comprising 2-methyltetrahydrofuran in the composition in an amount of no more than about 5000 ppm or further comprising isopropyl chloride in the composition in an amount of no more than about 300 ppm.

* * * * *